(12) United States Patent
Min et al.

(10) Patent No.: US 11,639,390 B2
(45) Date of Patent: May 2, 2023

(54) ANTI-ALPHA-4-BETA-7 ANTIBODIES

(71) Applicant: AbbVie Inc., North Chicago, IL (US)

(72) Inventors: Jing Min, Shrewsbury, MA (US); Teresa (Iok-Chan) Ng, Arlington Heighls, IL (US); Lorenzo Benatuil, Northborough, MA (US); Jacqueline Bixby, Auburn, MA (US); Tatyana Dekhtyar, Libertyville, IL (US); Feng Dong, Lansdale, PA (US); Axel Hernandez, Jr., Charlton, MA (US); Preethi Krishnan, Gurnee, IL (US); Liangjun Lu, Kildeer, IL (US); Federico Mensa, Glencoe, IL (US); Renee Miller, N. Grosvenordale, CT (US); Gautam Sahu, Mansfield, MA (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 17/378,565

(22) Filed: Jul. 16, 2021

(65) Prior Publication Data

US 2022/0017624 A1    Jan. 20, 2022

Related U.S. Application Data

(60) Provisional application No. 63/052,933, filed on Jul. 16, 2020.

(51) Int. Cl.

| | | |
|---|---|---|
| *C12N 5/02* | (2006.01) | |
| *C12N 5/20* | (2006.01) | |
| *C12N 1/20* | (2006.01) | |
| *C12N 15/00* | (2006.01) | |
| *C07K 16/46* | (2006.01) | |
| *C07K 16/00* | (2006.01) | |
| *C07H 21/04* | (2006.01) | |
| *C07K 16/28* | (2006.01) | |
| *A61P 31/18* | (2006.01) | |
| *C12N 15/63* | (2006.01) | |
| *A61K 39/00* | (2006.01) | |

(52) U.S. Cl.
CPC .......... *C07K 16/2839* (2013.01); *A61P 31/18* (2018.01); *C12N 15/63* (2013.01); *A61K 2039/505* (2013.01); *C07K 2317/52* (2013.01); *C07K 2317/565* (2013.01)

(58) Field of Classification Search
None
See application file for complete search history.

(56) References Cited

U.S. PATENT DOCUMENTS 9,610,264 B2    4/2017 Vinnik et al.

FOREIGN PATENT DOCUMENTS

| CA | 3028209 C | 1/2021 |
|---|---|---|
| WO | 2018104893 A1 | 6/2018 |

OTHER PUBLICATIONS

Gunst et al. HIV-1 acquisition in a man with ulcerative colitis on anti-α4β7 mAb vedolizumab treatment. AIDS: Sep. 1, 2020—vol. 34—Issue 11—p. 1689-1692 (Year: 2020).*
Sneller et al. An open-label phase 1 clinical trial ofthe anti-α4β7 monoclonal antibody vedolizumab in HIV-infected individuals. Sci. Transl. Med. 11, eaax3447 (2019), pp. 1-8. (Year: 2019).*
Mahomed et al. Clinical Trials of Broadly Neutralizing Monoclonal Antibodies for Human Immunodeficiency Virus Prevention: A Review. The Journal of Infectious Diseases, 2021;223:370-380. (Year: 2021).*
Polockand Kaul. How integral is the α4β7 integrin to HIV transmission? EBioMedicine 63(2021)103148, pp. 1-2. (Year: 2021).*
Arthos et al., 2008 "HIV-1 envelope protein binds to and signals through integrin alpha4beta7, the gut mucosal homing receptor for peripheral T cells," Nat Immunol 9(3):301-9.
Brenchley and Douek, 2008 "HIV infection and the gastrointestinal immune system," Mucosal Immunol 1(1):23-30.
Byrareddy et al., 2014 "Targeting [alpha]4[beta]7 integrin reduces mucosal transmission of simian immunodeficiency virus and protects gut-associated lymphoid tissue from infection," Nat Med 20(12):1397-1400.
Calenda et al., 2019 "Delayed vaginal SHIV infection in VRC01 and anti-[alpha]4[beta]7 treated rhesus macaques," PLOS Pathog https://doi.org/10.1371/journal.ppat.1007776 (22 pages).
Cicala et al., 2009 "The integrin α4β7 forms a complex with cell-surface CD4 and defines a T-cell subset that is highly susceptible to infection by HIV-1," PNAS 106(49):20877-82.
Goes et al., 2020 The V2 loop of HIV gp120 delivers costimulatory signals to CD4+ T cells through Integrin α4β7 and promotes cellular activation and infection, PNAS 117(51):32566-73.
Guzzo et al., 2017 "Virion incorporation of integrin a4l37 facilitates HIV-1 infection and intestinal homing," Sci Immunol 2(11) doi:10.1126/sciimmunol.aam7341 (30 pages).
Lertjuthaporn et al., 2018 "Select gp120 V2 domain specific antibodies derived from HIV and SIV infection and vaccination inhibit gp120 binding to a407," PLoS Pathog doi.org/10.1371/journal.ppat.1007278 (32 pages).
Li et al., 2014 "Binding of HIV-1 virions to α4β7 expressing cells and impact of antagonizing α4β7 on HIV-1 infection of primary CD4+ T cells," Virol Sin 29(6):381-92.
Naranjo-Gomez and Pelegrin, 2019 "Vaccinal effect of HIV-1 antibody therapy," Current Opinion in HIV and MDS, Lippincott, Williams & Wilkins 14(4):325-33 (23 pages).
Nawaz et al., 2018 "MAdCAM costimulation through Integrin-a437 promotes HIV replication," Mucosal Immunol 11, 1342-51.
Parsons et al., 2018 "Importance of Fc-mediated functions of anti-HIV-1 broadly neutralizing antibodies," Retrovirology 15:58 (12 pages).

(Continued)

*Primary Examiner* — Maher M Haddad
(74) *Attorney, Agent, or Firm* — Fox Rothschild LLP

(57) ABSTRACT

The present disclosure provides anti-α4β7 antibodies that bind human α4β7, their methods of making, and their uses to treat patients with HIV infection.

9 Claims, 29 Drawing Sheets

Specification includes a Sequence Listing.

(56) References Cited

OTHER PUBLICATIONS

Peachman et al., 2015 "Identification of New Regions in HIV-1 gp120 Variable 2 and 3 Loops that Bind to α4β7 Integrin Receptor," PloS One DOI: 10.1371/journal.pone.0143895 (25 pages).

Sivro et al., 2018 "Integrin [alpha]4[beta]7 expression on peripheral blood CD4 + T cells predicts HIV acquisition and disease progression outcomes," Sci Transl Med 10(425):doi:10.1126/scitranslmed. aam6354 (23 pages).

Uzzan et al., 2018 "Anti-[alpha]4[beta]7 therapy targets lymphoid aggregates in the gastrointestinal tract of HIV-1-infected individuals," Sci Transl Med 10(461):4711 (32 pages).

Ye et al., 2012 "Human regulatory T cells induce T-lymphocyte senescence," Blood 120(10):2021-31.

International Search Report dated Dec. 8, 2021 corresponding to related International Patent Application No. PCT/US2021/070898 (6 pages).

Written Opinion dated Dec. 8, 2021 corresponding to related International Patent Application No. PCT/US2021/070898 (7 pages).

\* cited by examiner

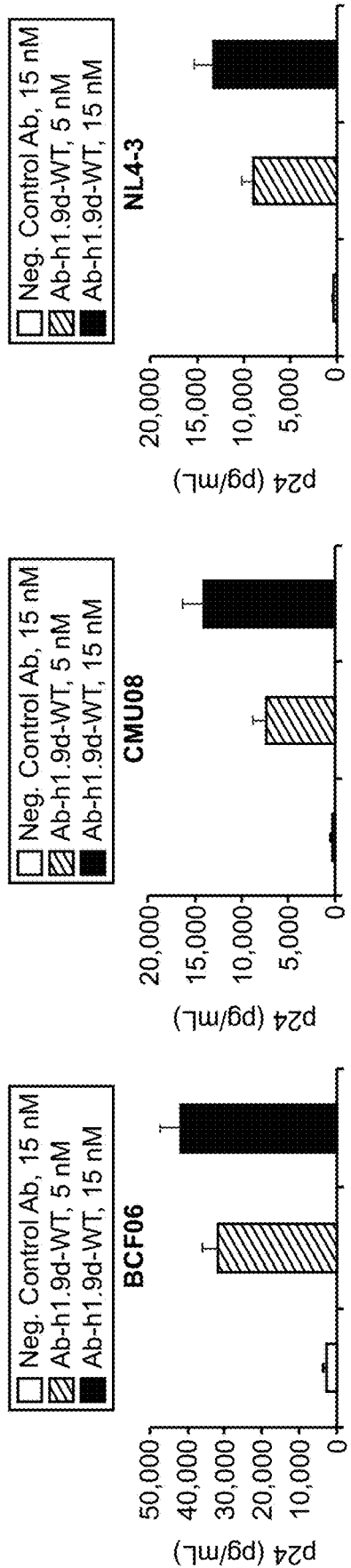
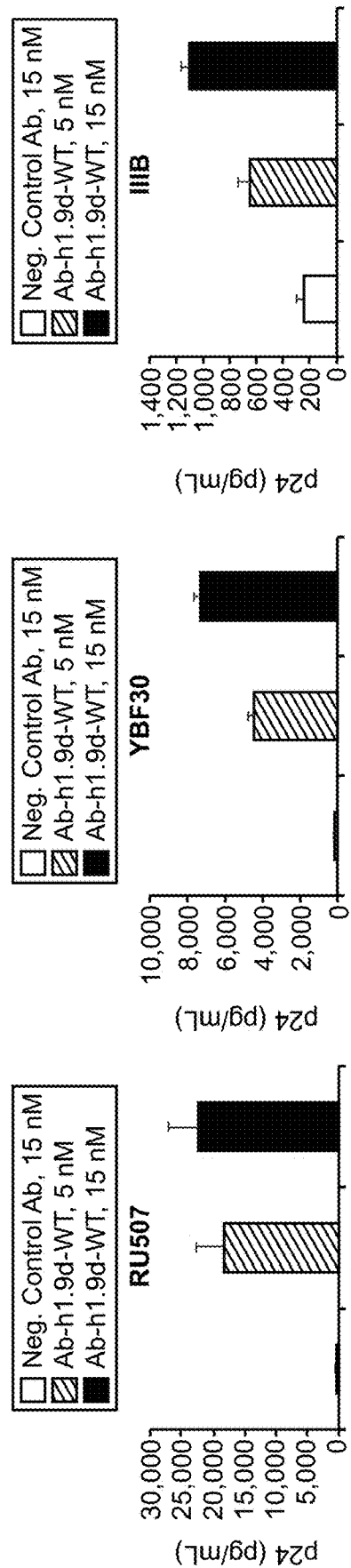
FIG. 7A, FIG. 7B, FIG. 7C, FIG. 7D, FIG. 7E, FIG. 7F

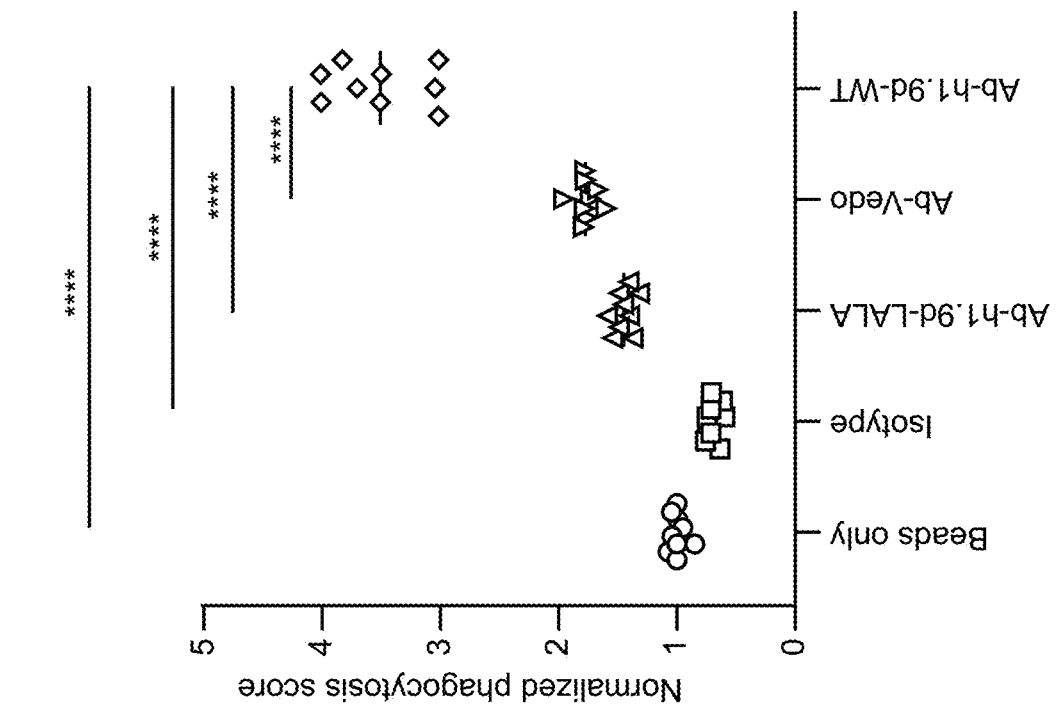
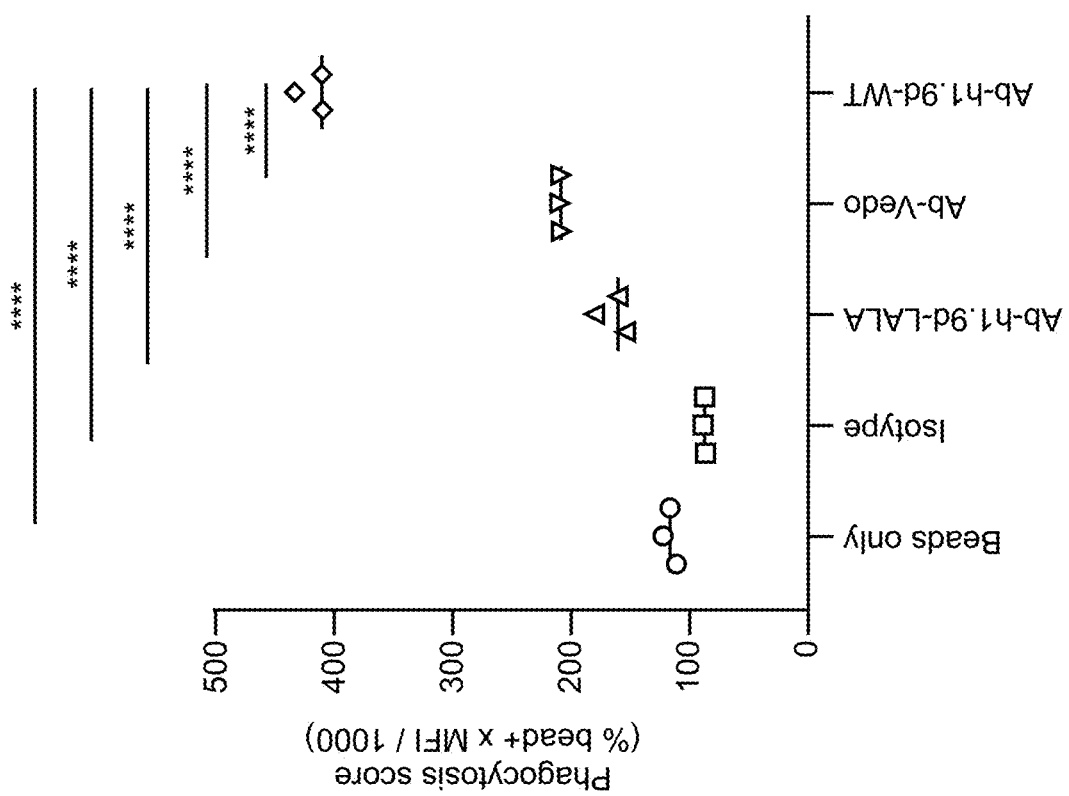

SEQUENCE LISTING

<160> NUMBER OF SEQ ID NOS: 100

<210> SEQ ID NO 1
<211> LENGTH: 1032
<212> TYPE: PRT
<213> ORGANISM: Homo sapiens

<400> SEQUENCE: 1

```
Met Ala Trp Glu Ala Arg Arg Glu Pro Gly Pro Arg Arg Ala Val
1               5                   10                  15

Arg Glu Thr Val Met Leu Leu Leu Cys Leu Gly Val Pro Thr Gly Arg
            20                  25                  30

Pro Tyr Asn Val Asp Thr Glu Ser Ala Leu Leu Tyr Gln Gly Pro His
            35                  40                  45

Asn Thr Leu Phe Gly Tyr Ser Val Val Leu His Ser His Gly Ala Asn
            50                  55                  60

Arg Trp Leu Leu Val Gly Ala Pro Thr Ala Asn Trp Leu Ala Asn Ala
65                  70                  75                  80

Ser Val Ile Asn Pro Gly Ala Ile Tyr Arg Cys Arg Ile Gly Lys Asn
                    85                  90                  95

Pro Gly Gln Thr Cys Glu Gln Leu Gln Leu Gly Ser Pro Asn Gly Glu
                100                 105                 110

Pro Cys Gly Lys Thr Cys Leu Glu Arg Asp Asn Gln Trp Leu Gly
                115                 120                 125

Val Thr Leu Ser Arg Gln Pro Gly Glu Asn Gly Ser Ile Val Thr Cys
            130                 135                 140

Gly His Arg Trp Lys Asn Ile Phe Tyr Ile Lys Asn Glu Asn Lys Leu
145                 150                 155                 160

Pro Thr Gly Gly Cys Tyr Gly Val Pro Pro Asp Leu Arg Thr Glu Leu
                    165                 170                 175

Ser Lys Arg Ile Ala Pro Cys Tyr Gln Asp Tyr Val Lys Lys Phe Gly
                180                 185                 190

Glu Asn Phe Ala Ser Cys Gln Ala Gly Ile Ser Ser Phe Tyr Thr Lys
            195                 200                 205

Asp Leu Ile Val Met Gly Ala Pro Gly Ser Ser Tyr Trp Thr Gly Ser
    210                 215                 220

Leu Phe Val Tyr Asn Ile Thr Thr Asn Lys Tyr Lys Ala Phe Leu Asp
225                 230                 235                 240

Lys Gln Asn Gln Val Lys Phe Gly Ser Tyr Leu Gly Tyr Ser Val Gly
                    245                 250                 255

Ala Gly His Phe Arg Ser Gln His Thr Thr Glu Val Val Gly Gly Ala
            260                 265                 270

Pro Gln His Glu Gln Ile Gly Lys Ala Tyr Ile Phe Ser Ile Asp Glu
        275                 280                 285

Lys Glu Leu Asn Ile Leu His Glu Met Lys Gly Lys Lys Leu Gly Ser
    290                 295                 300

Tyr Phe Gly Ala Ser Val Cys Ala Val Asp Leu Asn Ala Asp Gly Phe
305                 310                 315                 320

Ser Asp Leu Leu Val Gly Ala Pro Met Gln Ser Thr Ile Arg Glu Glu
                325                 330                 335

Gly Arg Val Phe Val Tyr Ile Asn Ser Gly Ser Gly Ala Val Met Asn
            340                 345                 350

Ala Met Glu Thr Asn Leu Val Gly Ser Asp Lys Tyr Ala Ala Arg Phe
        355                 360                 365
```

-continued

Gly Glu Ser Ile Val Asn Leu Gly Asp Ile Asp Asn Asp Gly Phe Glu
370                 375                 380

Asp Val Ala Ile Gly Ala Pro Gln Glu Asp Leu Gln Gly Ala Ile
385                 390                 395                 400

Tyr Ile Tyr Asn Gly Arg Ala Asp Gly Ile Ser Ser Thr Phe Ser Gln
            405                 410                 415

Arg Ile Glu Gly Leu Gln Ile Ser Lys Ser Leu Ser Met Phe Gly Gln
        420                 425                 430

Ser Ile Ser Gly Gln Ile Asp Ala Asp Asn Asn Gly Tyr Val Asp Val
        435                 440                 445

Ala Val Gly Ala Phe Arg Ser Asp Ser Ala Val Leu Leu Arg Thr Arg
450                 455                 460

Pro Val Val Ile Val Asp Ala Ser Leu Ser His Pro Glu Ser Val Asn
465                 470                 475                 480

Arg Thr Lys Phe Asp Cys Val Glu Asn Gly Trp Pro Ser Val Cys Ile
            485                 490                 495

Asp Leu Thr Leu Cys Phe Ser Tyr Lys Gly Lys Glu Val Pro Gly Tyr
            500                 505                 510

Ile Val Leu Phe Tyr Asn Met Ser Leu Asp Val Asn Arg Lys Ala Glu
        515                 520                 525

Ser Pro Pro Arg Phe Tyr Phe Ser Ser Asn Gly Thr Ser Asp Val Ile
        530                 535                 540

Thr Gly Ser Ile Gln Val Ser Ser Arg Glu Ala Asn Cys Arg Thr His
545                 550                 555                 560

Gln Ala Phe Met Arg Lys Asp Val Arg Asp Ile Leu Thr Pro Ile Gln
            565                 570                 575

Ile Glu Ala Ala Tyr His Leu Gly Pro His Val Ile Ser Lys Arg Ser
            580                 585                 590

Thr Glu Glu Phe Pro Pro Leu Gln Pro Ile Leu Gln Gln Lys Lys Glu
        595                 600                 605

Lys Asp Ile Met Lys Lys Thr Ile Asn Phe Ala Arg Phe Cys Ala His
610                 615                 620

Glu Asn Cys Ser Ala Asp Leu Gln Val Ser Ala Lys Ile Gly Phe Leu
625                 630                 635                 640

Lys Pro His Glu Asn Lys Thr Tyr Leu Ala Val Gly Ser Met Lys Thr
            645                 650                 655

Leu Met Leu Asn Val Ser Leu Phe Asn Ala Gly Asp Asp Ala Tyr Glu
            660                 665                 670

Thr Thr Leu His Val Lys Leu Pro Val Gly Leu Tyr Phe Ile Lys Ile
        675                 680                 685

Leu Glu Leu Glu Glu Lys Gln Ile Asn Cys Glu Val Thr Asp Asn Ser
690                 695                 700

Gly Val Val Gln Leu Asp Cys Ser Ile Gly Tyr Ile Tyr Val Asp His
705                 710                 715                 720

Leu Ser Arg Ile Asp Ile Ser Phe Leu Leu Asp Val Ser Ser Leu Ser
            725                 730                 735

Arg Ala Glu Glu Asp Leu Ser Ile Thr Val His Ala Thr Cys Glu Asn
            740                 745                 750

Glu Glu Glu Met Asp Asn Leu Lys His Ser Arg Val Thr Val Ala Ile
        755                 760                 765

Pro Leu Lys Tyr Glu Val Lys Leu Thr Val His Gly Phe Val Asn Pro
770                 775                 780

Thr Ser Phe Val Tyr Gly Ser Asn Asp Glu Asn Glu Pro Glu Thr Cys

```
                785                 790                 795                 800
Met Val Glu Lys Met Asn Leu Thr Phe His Val Ile Asn Thr Gly Asn
                    805                 810                 815

Ser Met Ala Pro Asn Val Ser Val Glu Ile Met Val Pro Asn Ser Phe
                820                 825                 830

Ser Pro Gln Thr Asp Lys Leu Phe Asn Ile Leu Asp Val Gln Thr Thr
                835                 840                 845

Thr Gly Glu Cys His Phe Glu Asn Tyr Gln Arg Val Cys Ala Leu Glu
            850                 855                 860

Gln Gln Lys Ser Ala Met Gln Thr Leu Lys Gly Ile Val Arg Phe Leu
865                 870                 875                 880

Ser Lys Thr Asp Lys Arg Leu Leu Tyr Cys Ile Lys Ala Asp Pro His
                885                 890                 895

Cys Leu Asn Phe Leu Cys Asn Phe Gly Lys Met Glu Ser Gly Lys Glu
                900                 905                 910

Ala Ser Val His Ile Gln Leu Glu Gly Arg Pro Ser Ile Leu Glu Met
            915                 920                 925

Asp Glu Thr Ser Ala Leu Lys Phe Glu Ile Arg Ala Thr Gly Phe Pro
        930                 935                 940

Glu Pro Asn Pro Arg Val Ile Glu Leu Asn Lys Asp Glu Asn Val Ala
945                 950                 955                 960

His Val Leu Leu Glu Gly Leu His His Gln Arg Pro Lys Arg Tyr Phe
                965                 970                 975

Thr Ile Val Ile Ile Ser Ser Leu Leu Leu Gly Leu Ile Val Leu
            980                 985                 990

Leu Leu Ile Ser Tyr Val Met Trp  Lys Ala Gly Phe Phe  Lys Arg Gln
        995                 1000                1005

Tyr Lys  Ser Ile Leu Gln Glu  Glu Asn Arg Arg Asp  Ser Trp Ser
    1010                1015                1020

Tyr Ile  Asn Ser Lys Ser Asn  Asp Asp
    1025                1030

<210> SEQ ID NO 2
<211> LENGTH: 195
<212> TYPE: PRT
<213> ORGANISM: Homo sapiens

<400> SEQUENCE: 2

Met Ala Trp Glu Ala Arg Arg Glu Pro Gly Pro Arg Arg Ala Ala Val
1               5                   10                  15

Arg Glu Thr Val Met Leu Leu Leu Cys Leu Gly Val Pro Thr Gly Arg
                20                  25                  30

Pro Tyr Asn Val Asp Thr Glu Ser Ala Leu Leu Tyr Gln Gly Pro His
            35                  40                  45

Asn Thr Leu Phe Gly Tyr Ser Val Val Leu His Ser His Gly Ala Asn
        50                  55                  60

Arg Trp Leu Leu Val Gly Ala Pro Thr Ala Asn Trp Leu Ala Asn Ala
65                  70                  75                  80

Ser Val Ile Asn Pro Gly Ala Ile Tyr Arg Cys Arg Ile Gly Lys Asn
                85                  90                  95

Pro Gly Gln Thr Cys Glu Gln Leu Gln Leu Gly Ser Pro Asn Gly Glu
            100                 105                 110

Pro Cys Gly Lys Thr Cys Leu Glu Glu Arg Asp Asn Gln Trp Leu Gly
        115                 120                 125
```

Val Thr Leu Ser Arg Gln Pro Gly Glu Asn Gly Ser Ile Val Thr Cys
130                 135                 140

Gly His Arg Trp Lys Asn Ile Phe Tyr Ile Lys Asn Glu Asn Lys Leu
145                 150                 155                 160

Pro Thr Gly Gly Cys Tyr Gly Val Pro Pro Asp Leu Arg Thr Glu Leu
                165                 170                 175

Ser Lys Arg Ile Ala Pro Cys Tyr Gln Gly Ser Ile Ser Lys Tyr Arg
                180                 185                 190

Ala Arg Thr
        195

<210> SEQ ID NO 3
<211> LENGTH: 798
<212> TYPE: PRT
<213> ORGANISM: Homo sapiens

<400> SEQUENCE: 3

Met Val Ala Leu Pro Met Val Leu Val Leu Leu Leu Val Leu Ser Arg
1               5                   10                  15

Gly Glu Ser Glu Leu Asp Ala Lys Ile Pro Ser Thr Gly Asp Ala Thr
                20                  25                  30

Glu Trp Arg Asn Pro His Leu Ser Met Leu Gly Ser Cys Gln Pro Ala
            35                  40                  45

Pro Ser Cys Gln Lys Cys Ile Leu Ser His Pro Ser Cys Ala Trp Cys
50                  55                  60

Lys Gln Leu Asn Phe Thr Ala Ser Gly Glu Ala Glu Ala Arg Arg Cys
65                  70                  75                  80

Ala Arg Arg Glu Glu Leu Leu Ala Arg Gly Cys Pro Leu Glu Glu Leu
                85                  90                  95

Glu Glu Pro Arg Gly Gln Gln Glu Val Leu Gln Asp Gln Pro Leu Ser
            100                 105                 110

Gln Gly Ala Arg Gly Glu Gly Ala Thr Gln Leu Ala Pro Gln Arg Val
        115                 120                 125

Arg Val Thr Leu Arg Pro Gly Glu Pro Gln Gln Leu Gln Val Arg Phe
130                 135                 140

Leu Arg Ala Glu Gly Tyr Pro Val Asp Leu Tyr Tyr Leu Met Asp Leu
145                 150                 155                 160

Ser Tyr Ser Met Lys Asp Asp Leu Glu Arg Val Arg Gln Leu Gly His
                165                 170                 175

Ala Leu Leu Val Arg Leu Gln Glu Val Thr His Ser Val Arg Ile Gly
            180                 185                 190

Phe Gly Ser Phe Val Asp Lys Thr Val Leu Pro Phe Val Ser Thr Val
        195                 200                 205

Pro Ser Lys Leu Arg His Pro Cys Pro Thr Arg Leu Glu Arg Cys Gln
210                 215                 220

Ser Pro Phe Ser Phe His His Val Leu Ser Leu Thr Gly Asp Ala Gln
225                 230                 235                 240

Ala Phe Glu Arg Glu Val Gly Arg Gln Ser Val Ser Gly Asn Leu Asp
                245                 250                 255

Ser Pro Glu Gly Gly Phe Asp Ala Ile Leu Gln Ala Ala Leu Cys Gln
            260                 265                 270

Glu Gln Ile Gly Trp Arg Asn Val Ser Arg Leu Leu Val Phe Thr Ser
        275                 280                 285

Asp Asp Thr Phe His Thr Ala Gly Asp Gly Lys Leu Gly Gly Ile Phe
290                 295                 300

```
Met Pro Ser Asp Gly His Cys His Leu Asp Ser Asn Gly Leu Tyr Ser
305                 310                 315                 320

Arg Ser Thr Glu Phe Asp Tyr Pro Ser Val Gly Gln Val Ala Gln Ala
            325                 330                 335

Leu Ser Ala Ala Asn Ile Gln Pro Ile Phe Ala Val Thr Ser Ala Ala
        340                 345                 350

Leu Pro Val Tyr Gln Glu Leu Ser Lys Leu Ile Pro Lys Ser Ala Val
    355                 360                 365

Gly Glu Leu Ser Glu Asp Ser Ser Asn Val Val Gln Leu Ile Met Asp
370                 375                 380

Ala Tyr Asn Ser Leu Ser Ser Thr Val Thr Leu Glu His Ser Ser Leu
385                 390                 395                 400

Pro Pro Gly Val His Ile Ser Tyr Glu Ser Gln Cys Glu Gly Pro Glu
                405                 410                 415

Lys Arg Glu Gly Lys Ala Glu Asp Arg Gly Gln Cys Asn His Val Arg
            420                 425                 430

Ile Asn Gln Thr Val Thr Phe Trp Val Ser Leu Gln Ala Thr His Cys
        435                 440                 445

Leu Pro Glu Pro His Leu Leu Arg Leu Arg Ala Leu Gly Phe Ser Glu
    450                 455                 460

Glu Leu Ile Val Glu Leu His Thr Leu Cys Asp Cys Asn Cys Ser Asp
465                 470                 475                 480

Thr Gln Pro Gln Ala Pro His Cys Ser Asp Gly Gln Gly His Leu Gln
                485                 490                 495

Cys Gly Val Cys Ser Cys Ala Pro Gly Arg Leu Gly Arg Leu Cys Glu
            500                 505                 510

Cys Ser Val Ala Glu Leu Ser Ser Pro Asp Leu Glu Ser Gly Cys Arg
        515                 520                 525

Ala Pro Asn Gly Thr Gly Pro Leu Cys Ser Gly Lys Gly His Cys Gln
    530                 535                 540

Cys Gly Arg Cys Ser Cys Ser Gly Gln Ser Ser Gly His Leu Cys Glu
545                 550                 555                 560

Cys Asp Asp Ala Ser Cys Glu Arg His Glu Gly Ile Leu Cys Gly Gly
                565                 570                 575

Phe Gly Arg Cys Gln Cys Gly Val Cys His Cys His Ala Asn Arg Thr
            580                 585                 590

Gly Arg Ala Cys Glu Cys Ser Gly Asp Met Asp Ser Cys Ile Ser Pro
        595                 600                 605

Glu Gly Gly Leu Cys Ser Gly His Gly Arg Cys Lys Cys Asn Arg Cys
    610                 615                 620

Gln Cys Leu Asp Gly Tyr Tyr Gly Ala Leu Cys Asp Gln Cys Pro Gly
625                 630                 635                 640

Cys Lys Thr Pro Cys Glu Arg His Arg Asp Cys Ala Glu Cys Gly Ala
                645                 650                 655

Phe Arg Thr Gly Pro Leu Ala Thr Asn Cys Ser Thr Ala Cys Ala His
            660                 665                 670

Thr Asn Val Thr Leu Ala Leu Ala Pro Ile Leu Asp Asp Gly Trp Cys
        675                 680                 685

Lys Glu Arg Thr Leu Asp Asn Gln Leu Phe Phe Phe Leu Val Glu Asp
    690                 695                 700

Asp Ala Arg Gly Thr Val Val Leu Arg Val Arg Pro Gln Glu Lys Gly
705                 710                 715                 720
```

-continued

Ala Asp His Thr Gln Ala Ile Val Leu Gly Cys Val Gly Gly Ile Val
            725                 730                 735

Ala Val Gly Leu Gly Leu Val Leu Ala Tyr Arg Leu Ser Val Glu Ile
            740                 745                 750

Tyr Asp Arg Arg Glu Tyr Ser Arg Phe Glu Lys Glu Gln Gln Gln Leu
            755                 760                 765

Asn Trp Lys Gln Asp Ser Asn Pro Leu Tyr Lys Ser Ala Ile Thr Thr
            770                 775                 780

Thr Ile Asn Pro Arg Phe Gln Glu Ala Asp Ser Pro Thr Leu
785                 790                 795

<210> SEQ ID NO 4
<211> LENGTH: 650
<212> TYPE: PRT
<213> ORGANISM: Homo sapiens

<400> SEQUENCE: 4

Met Val Ala Leu Pro Met Val Leu Val Leu Leu Leu Val Leu Ser Arg
1               5                   10                  15

Gly Glu Ser Glu Leu Asp Ala Lys Ile Pro Ser Thr Gly Asp Ala Thr
            20                  25                  30

Glu Trp Arg Asn Pro His Leu Ser Met Leu Gly Ser Cys Gln Pro Ala
            35                  40                  45

Pro Ser Cys Gln Lys Cys Ile Leu Ser His Pro Ser Cys Ala Trp Cys
            50                  55                  60

Lys Gln Leu Asn Phe Thr Ala Ser Gly Glu Ala Glu Ala Arg Arg Cys
65                  70                  75                  80

Ala Arg Arg Glu Glu Leu Leu Ala Arg Gly Cys Pro Leu Glu Glu Leu
            85                  90                  95

Glu Glu Pro Arg Gly Gln Gln Glu Val Leu Gln Asp Gln Pro Leu Ser
            100                 105                 110

Gln Gly Ala Arg Gly Glu Gly Ala Thr Gln Leu Ala Pro Gln Arg Val
            115                 120                 125

Arg Val Thr Leu Arg Pro Gly Glu Pro Gln Gln Leu Gln Val Arg Phe
            130                 135                 140

Leu Arg Ala Glu Gly Tyr Pro Val Asp Leu Tyr Tyr Leu Met Asp Leu
145                 150                 155                 160

Ser Tyr Ser Met Lys Asp Asp Leu Glu Arg Val Arg Gln Leu Gly His
            165                 170                 175

Ala Leu Leu Val Arg Leu Gln Glu Val Thr His Ser Val Arg Ile Gly
            180                 185                 190

Phe Gly Ser Phe Val Asp Lys Thr Val Leu Pro Phe Val Ser Thr Val
            195                 200                 205

Pro Ser Lys Leu Arg His Pro Cys Pro Thr Arg Leu Glu Arg Cys Gln
            210                 215                 220

Ser Pro Phe Ser Phe His His Val Leu Ser Leu Thr Gly Asp Ala Gln
225                 230                 235                 240

Ala Phe Glu Arg Glu Val Gly Arg Gln Ser Val Ser Gly Asn Leu Asp
            245                 250                 255

Ser Pro Glu Gly Gly Phe Asp Ala Ile Leu Gln Ala Ala Leu Cys Gln
            260                 265                 270

Glu Gln Ile Gly Trp Arg Asn Val Ser Arg Leu Leu Val Phe Thr Ser
            275                 280                 285

Asp Asp Thr Phe His Thr Ala Gly Asp Gly Lys Leu Gly Gly Ile Phe
            290                 295                 300

Met Pro Ser Asp Gly His Cys His Leu Asp Ser Asn Gly Leu Tyr Ser
305                 310                 315                 320

Arg Ser Thr Glu Phe Asp Tyr Pro Ser Val Gly Gln Val Ala Gln Ala
            325                 330                 335

Leu Ser Ala Ala Asn Ile Gln Pro Ile Phe Ala Val Thr Ser Ala Ala
                340                 345                 350

Leu Pro Val Tyr Gln Glu Leu Ser Lys Leu Ile Pro Lys Ser Ala Val
        355                 360                 365

Gly Glu Leu Ser Glu Asp Ser Ser Asn Val Val Gln Leu Ile Met Asp
    370                 375                 380

Ala Tyr Asn Ser Leu Ser Ser Thr Val Thr Leu Glu His Ser Ser Leu
385                 390                 395                 400

Pro Pro Gly Val His Ile Ser Tyr Glu Ser Gln Cys Glu Gly Pro Glu
                405                 410                 415

Lys Arg Glu Gly Lys Ala Glu Asp Arg Gly Gln Cys Asn His Val Arg
            420                 425                 430

Ile Asn Gln Thr Val Thr Phe Trp Val Ser Leu Gln Ala Thr His Cys
        435                 440                 445

Leu Pro Glu Pro His Leu Leu Arg Leu Arg Ala Leu Gly Phe Ser Glu
    450                 455                 460

Glu Leu Ile Val Glu Leu His Thr Leu Cys Asp Cys Asn Cys Ser Asp
465                 470                 475                 480

Thr Gln Pro Gln Ala Pro His Cys Ser Asp Gly Gln Gly His Leu Gln
                485                 490                 495

Cys Gly Val Cys Arg Asp Cys Ala Glu Cys Gly Ala Phe Arg Thr Gly
            500                 505                 510

Pro Leu Ala Thr Asn Cys Ser Thr Ala Cys Ala His Thr Asn Val Thr
        515                 520                 525

Leu Ala Leu Ala Pro Ile Leu Asp Asp Gly Trp Cys Lys Glu Arg Thr
    530                 535                 540

Leu Asp Asn Gln Leu Phe Phe Phe Leu Val Glu Asp Ala Arg Gly
545                 550                 555                 560

Thr Val Val Leu Arg Val Arg Pro Gln Glu Lys Gly Ala Asp His Thr
                565                 570                 575

Gln Ala Ile Val Leu Gly Cys Val Gly Gly Ile Val Ala Val Gly Leu
            580                 585                 590

Gly Leu Val Leu Ala Tyr Arg Leu Ser Val Glu Ile Tyr Asp Arg Arg
        595                 600                 605

Glu Tyr Ser Arg Phe Glu Lys Glu Gln Gln Gln Leu Asn Trp Lys Gln
    610                 615                 620

Asp Ser Asn Pro Leu Tyr Lys Ser Ala Ile Thr Thr Thr Ile Asn Pro
625                 630                 635                 640

Arg Phe Gln Glu Ala Asp Ser Pro Thr Leu
                645                 650

<210> SEQ ID NO 5
<211> LENGTH: 382
<212> TYPE: PRT
<213> ORGANISM: Homo sapiens

<400> SEQUENCE: 5

Met Asp Phe Gly Leu Ala Leu Leu Leu Ala Gly Leu Leu Gly Leu Leu
1               5                   10                  15

Leu Gly Gln Ser Leu Gln Val Lys Pro Leu Gln Val Glu Pro Pro Glu

```
            20                  25                  30
Pro Val Ala Val Ala Leu Gly Ala Ser Arg Gln Leu Thr Cys Arg
        35                  40                  45

Leu Ala Cys Ala Asp Arg Gly Ala Ser Val Gln Trp Arg Gly Leu Asp
    50                  55                  60

Thr Ser Leu Gly Ala Val Gln Ser Asp Thr Gly Arg Ser Val Leu Thr
65                  70                  75                  80

Val Arg Asn Ala Ser Leu Ser Ala Gly Thr Arg Val Cys Val Gly
                85                  90                  95

Ser Cys Gly Gly Arg Thr Phe Gln His Thr Val Gln Leu Leu Val Tyr
            100                 105                 110

Ala Phe Pro Asp Gln Leu Thr Val Ser Pro Ala Ala Leu Val Pro Gly
            115                 120                 125

Asp Pro Glu Val Ala Cys Thr Ala His Lys Val Thr Pro Val Asp Pro
            130                 135                 140

Asn Ala Leu Ser Phe Ser Leu Leu Val Gly Gly Gln Glu Leu Glu Gly
145                 150                 155                 160

Ala Gln Ala Leu Gly Pro Glu Val Gln Glu Glu Glu Glu Pro Gln
                165                 170                 175

Gly Asp Glu Asp Val Leu Phe Arg Val Thr Glu Arg Trp Arg Leu Pro
            180                 185                 190

Pro Leu Gly Thr Pro Val Pro Pro Ala Leu Tyr Cys Gln Ala Thr Met
        195                 200                 205

Arg Leu Pro Gly Leu Glu Leu Ser His Arg Gln Ala Ile Pro Val Leu
    210                 215                 220

His Ser Pro Thr Ser Pro Glu Pro Pro Asp Thr Thr Ser Pro Glu Ser
225                 230                 235                 240

Pro Asp Thr Thr Ser Pro Glu Ser Pro Asp Thr Thr Ser Gln Glu Pro
                245                 250                 255

Pro Asp Thr Thr Ser Pro Glu Pro Pro Asp Lys Thr Ser Pro Glu Pro
            260                 265                 270

Ala Pro Gln Gln Gly Ser Thr His Thr Pro Arg Ser Pro Gly Ser Thr
            275                 280                 285

Arg Thr Arg Arg Pro Glu Ile Ser Gln Ala Gly Pro Thr Gln Gly Glu
    290                 295                 300

Val Ile Pro Thr Gly Ser Ser Lys Pro Ala Gly Asp Gln Leu Pro Ala
305                 310                 315                 320

Ala Leu Trp Thr Ser Ser Ala Val Leu Gly Leu Leu Leu Ala Leu
                325                 330                 335

Pro Thr Tyr His Leu Trp Lys Arg Cys Arg His Leu Ala Glu Asp Asp
            340                 345                 350

Thr His Pro Pro Ala Ser Leu Arg Leu Leu Pro Gln Val Ser Ala Trp
            355                 360                 365

Ala Gly Leu Arg Gly Thr Gly Gln Val Gly Ile Ser Pro Ser
370                 375                 380

<210> SEQ ID NO 6
<211> LENGTH: 739
<212> TYPE: PRT
<213> ORGANISM: Homo sapiens

<400> SEQUENCE: 6

Met Pro Gly Lys Met Val Val Ile Leu Gly Ala Ser Asn Ile Leu Trp
1               5                   10                  15
```

```
Ile Met Phe Ala Ala Ser Gln Ala Phe Lys Ile Glu Thr Thr Pro Glu
             20                  25                  30

Ser Arg Tyr Leu Ala Gln Ile Gly Asp Ser Val Ser Leu Thr Cys Ser
         35                  40                  45

Thr Thr Gly Cys Glu Ser Pro Phe Phe Ser Trp Arg Thr Gln Ile Asp
     50                  55                  60

Ser Pro Leu Asn Gly Lys Val Thr Asn Glu Gly Thr Thr Ser Thr Leu
65                   70                  75                  80

Thr Met Asn Pro Val Ser Phe Gly Asn Glu His Ser Tyr Leu Cys Thr
                 85                  90                  95

Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
        115                 120                 125

Ala Gly Lys Pro Ile Thr Val Lys Cys Ser Val Ala Asp Val Tyr Pro
        130                 135                 140

Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
        195                 200                 205

Thr Val Arg Gln Ala Val Lys Glu Leu Gln Val Tyr Ile Ser Pro Lys
        210                 215                 220

Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255

Phe Trp Ser Lys Lys Leu Asp Asn Gly Asn Leu Gln His Leu Ser Gly
            260                 265                 270

Asn Ala Thr Leu Thr Leu Ile Ala Met Arg Met Glu Asp Ser Gly Ile
        275                 280                 285

Tyr Val Cys Glu Gly Val Asn Leu Ile Gly Lys Asn Arg Lys Glu Val
        290                 295                 300

Glu Leu Ile Val Gln Glu Lys Pro Phe Thr Val Glu Ile Ser Pro Gly
305                 310                 315                 320

Pro Arg Ile Ala Ala Gln Ile Gly Asp Ser Val Met Leu Thr Cys Ser
                325                 330                 335

Val Met Gly Cys Glu Ser Pro Ser Phe Ser Trp Arg Thr Gln Ile Asp
            340                 345                 350

Ser Pro Leu Ser Gly Lys Val Arg Ser Glu Gly Thr Asn Ser Thr Leu
        355                 360                 365

Thr Leu Ser Pro Val Ser Phe Glu Asn Glu His Ser Tyr Leu Cys Thr
        370                 375                 380

Val Thr Cys Gly His Lys Lys Leu Glu Lys Gly Ile Gln Val Glu Leu
385                 390                 395                 400

Tyr Ser Phe Pro Arg Asp Pro Glu Ile Glu Met Ser Gly Gly Leu Val
                405                 410                 415

Asn Gly Ser Ser Val Thr Val Ser Cys Lys Val Pro Ser Val Tyr Pro
            420                 425                 430

Leu Asp Arg Leu Glu Ile Glu Leu Leu Lys Gly Glu Thr Ile Leu Glu
```

```
                    435                 440                 445
Asn Ile Glu Phe Leu Glu Asp Thr Asp Met Lys Ser Leu Glu Asn Lys
450                 455                 460

Ser Leu Glu Met Thr Phe Ile Pro Thr Ile Glu Asp Thr Gly Lys Ala
465                 470                 475                 480

Leu Val Cys Gln Ala Lys Leu His Ile Asp Asp Met Glu Phe Glu Pro
                    485                 490                 495

Lys Gln Arg Gln Ser Thr Gln Thr Leu Tyr Val Asn Val Ala Pro Arg
                500                 505                 510

Asp Thr Thr Val Leu Val Ser Pro Ser Ser Ile Leu Glu Glu Gly Ser
                515                 520                 525

Ser Val Asn Met Thr Cys Leu Ser Gln Gly Phe Pro Ala Pro Lys Ile
530                 535                 540

Leu Trp Ser Arg Gln Leu Pro Asn Gly Glu Leu Gln Pro Leu Ser Glu
545                 550                 555                 560

Asn Ala Thr Leu Thr Leu Ile Ser Thr Lys Met Glu Asp Ser Gly Val
                565                 570                 575

Tyr Leu Cys Glu Gly Ile Asn Gln Ala Gly Arg Ser Arg Lys Glu Val
                580                 585                 590

Glu Leu Ile Ile Gln Val Thr Pro Lys Asp Ile Lys Leu Thr Ala Phe
                595                 600                 605

Pro Ser Glu Ser Val Lys Glu Gly Asp Thr Val Ile Ile Ser Cys Thr
610                 615                 620

Cys Gly Asn Val Pro Glu Thr Trp Ile Ile Leu Lys Lys Lys Ala Glu
625                 630                 635                 640

Thr Gly Asp Thr Val Leu Lys Ser Ile Asp Gly Ala Tyr Thr Ile Arg
                645                 650                 655

Lys Ala Gln Leu Lys Asp Ala Gly Val Tyr Glu Cys Glu Ser Lys Asn
                660                 665                 670

Lys Val Gly Ser Gln Leu Arg Ser Leu Thr Leu Asp Val Gln Gly Arg
                675                 680                 685

Glu Asn Asn Lys Asp Tyr Phe Ser Pro Glu Leu Leu Val Leu Tyr Phe
                690                 695                 700

Ala Ser Ser Leu Ile Ile Pro Ala Ile Gly Met Ile Ile Tyr Phe Ala
705                 710                 715                 720

Arg Lys Ala Asn Met Lys Gly Ser Tyr Ser Leu Val Glu Ala Gln Lys
                725                 730                 735

Ser Lys Val

<210> SEQ ID NO 7
<211> LENGTH: 42
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Features an N-term Biotin with a
      Trioxatridecan-succinamic acid (Ttds) linker
<220> FEATURE:
<221> NAME/KEY: MOD_RES
<222> LOCATION: (42)..(42)
<223> OTHER INFORMATION: AMIDATION

<400> SEQUENCE: 7

Cys Ser Phe Asn Met Thr Thr Glu Leu Arg Asp Lys Lys Gln Lys Val
1               5                   10                  15
```

His Ala Leu Phe Tyr Lys Leu Asp Ile Val Pro Ile Glu Asp Asn Thr
            20                  25                  30

Ser Ser Ser Glu Tyr Arg Leu Ile Asn Cys
        35                  40

<210> SEQ ID NO 8
<211> LENGTH: 42
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Features an N-term Biotin with a
      Trioxatridecan-succinamic acid (Ttds) linker
<220> FEATURE:
<221> NAME/KEY: MOD_RES
<222> LOCATION: (42)..(42)
<223> OTHER INFORMATION: AMIDATION

<400> SEQUENCE: 8

Cys Ser Phe Asn Met Thr Thr Glu Leu Arg Asp Lys Lys Gln Lys Val
1               5                   10                  15

His Ala Leu Phe Tyr Lys Ala Ala Ala Ala Pro Ile Glu Asp Asn Thr
            20                  25                  30

Ser Ser Ser Glu Tyr Arg Leu Ile Asn Cys
        35                  40

<210> SEQ ID NO 9

<400> SEQUENCE: 9

000

<210> SEQ ID NO 10
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 10

Glu Val Gln Leu Gln Gln Ser Val Ala Glu Leu Val Arg Pro Gly Ala
1               5                   10                  15

Ser Val Lys Leu Ser Cys Thr Thr Ser Gly Phe Asn Ile Lys Asn Thr
            20                  25                  30

Tyr Met His Trp Val Lys Gln Arg Pro Lys Gln Gly Leu Glu Trp Ile
        35                  40                  45

Gly Arg Ile Asp Pro Ala Asn Gly His Thr Glu Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu His Leu Ser Ser Leu Thr Ser Asp Asp Thr Ala Ile Tyr Tyr Cys
                85                  90                  95

Tyr Tyr Val Asp Ser Trp Gly Gln Gly Thr Thr Leu Thr Val Ser Ser
            100                 105                 110

<210> SEQ ID NO 11
<211> LENGTH: 107
<212> TYPE: PRT
<213> ORGANISM: Artificial Sequence
<220> FEATURE:

<223> OTHER INFORMATION: Synthetic polypeptide

<400> SEQUENCE: 11

Asp Ile Leu Met Thr Gln Ser Pro Ser Ser Met Ser Val Ser Leu Gly
1               5                   10                  15

Asp Thr Val Ser Ile Thr Cys His Ala Ser Gln Gly Ile Ser Asp Asn
            20                  25                  30

Ile Gly Trp Leu Gln Gln Arg Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ala Gln Phe Pro Trp
                85                  90                  95

Thr Phe Gly Gly Gly Thr Thr Leu Glu Ile Lys
            100                 105

<210> SEQ ID NO 12
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 12

Asn Thr Tyr Met His
1               5

<210> SEQ ID NO 13
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 13

Arg Ile Asp Pro Ala Asn Gly His Thr Glu Tyr Ala Pro
1               5                   10

<210> SEQ ID NO 14
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 14

Val Asp Ser
1

<210> SEQ ID NO 15
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 15

His Ala Ser Gln Gly Ile Ser Asp Asn Ile Gly
1               5                   10

<210> SEQ ID NO 16

```
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 16

His Gly Thr Asn Leu Glu Asp
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 17

Val Gln Tyr Ala Gln Phe Pro Trp Thr
1               5

<210> SEQ ID NO 18

<400> SEQUENCE: 18

000

<210> SEQ ID NO 19

<400> SEQUENCE: 19

000

<210> SEQ ID NO 20
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 20

Glu Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asn Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly His Thr Glu Tyr Ala Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asp Ser Trp Gly Gln Gly Thr Thr Val Thr Val Ser Ser
            100                 105                 110

<210> SEQ ID NO 21
<211> LENGTH: 112
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: (23)..(23)
```

```
<223> OTHER INFORMATION: K to T
<220> FEATURE:
<221> NAME/KEY: VARIANT
<222> LOCATION: (24)..(24)
<223> OTHER INFORMATION: A to T
<220> FEATURE:
<221> NAME/KEY: VARIANT
<222> LOCATION: (38)..(38)
<223> OTHER INFORMATION: R to K
<220> FEATURE:
<221> NAME/KEY: VARIANT
<222> LOCATION: (40)..(40)
<223> OTHER INFORMATION: A to R
<220> FEATURE:
<221> NAME/KEY: VARIANT
<222> LOCATION: (48)..(48)
<223> OTHER INFORMATION: M to I
<220> FEATURE:
<221> NAME/KEY: VARIANT
<222> LOCATION: (67)..(67)
<223> OTHER INFORMATION: R to K
<220> FEATURE:
<221> NAME/KEY: VARIANT
<222> LOCATION: (68)..(68)
<223> OTHER INFORMATION: V to A
<220> FEATURE:
<221> NAME/KEY: VARIANT
<222> LOCATION: (77)..(77)
<223> OTHER INFORMATION: S to N
<220> FEATURE:
<221> NAME/KEY: VARIANT
<222> LOCATION: (81)..(81)
<223> OTHER INFORMATION: M to L
<220> FEATURE:
<221> NAME/KEY: VARIANT
<222> LOCATION: (97)..(97)
<223> OTHER INFORMATION: A to Y
<220> FEATURE:
<221> NAME/KEY: VARIANT
<222> LOCATION: (98)..(98)
<223> OTHER INFORMATION: R to Y

<400> SEQUENCE: 21

Glu Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asn Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly His Thr Glu Tyr Ala Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asp Ser Trp Gly Gln Gly Thr Thr Val Thr Val Ser Ser
            100                 105                 110

<210> SEQ ID NO 22
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 22

Glu Val Gln Leu Val Gln Ser Gly Ala Glu Val Lys Lys Pro Gly Ser
1               5                   10                  15

Ser Val Lys Val Ser Cys Thr Thr Ser Gly Phe Asn Ile Lys Asn Thr
```

```
                    20                  25                  30

Tyr Met His Trp Val Lys Gln Arg Pro Gly Gln Gly Leu Glu Trp Ile
            35                  40                  45

Gly Arg Ile Asp Pro Ala Asn Gly His Thr Glu Tyr Ala Pro Lys Phe
        50                  55                  60

Gln Gly Lys Ala Thr Ile Thr Ala Asp Glu Ser Thr Asn Thr Ala Tyr
65                  70                  75                  80

Leu Glu Leu Ser Ser Leu Arg Ser Glu Asp Thr Ala Val Tyr Tyr Cys
                85                  90                  95

Tyr Tyr Val Asp Ser Trp Gly Gln Gly Thr Thr Val Thr Val Ser Ser
            100                 105                 110

<210> SEQ ID NO 23
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 23

Glu Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asn Thr
            20                  25                  30

Tyr Met His Trp Val Arg Gln Ala Pro Gly Gln Gly Leu Glu Trp Ile
            35                  40                  45

Gly Arg Ile Asp Pro Ala Asn Gly His Thr Glu Tyr Ala Pro Lys Phe
        50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Tyr Tyr Val Asp Ser Trp Gly Gln Gly Thr Thr Val Thr Val Ser Ser
            100                 105                 110

<210> SEQ ID NO 24

<400> SEQUENCE: 24

000

<210> SEQ ID NO 25
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Ser Asp Asn
            20                  25                  30

Ile Gly Trp Tyr Gln Gln Lys Pro Gly Lys Ala Pro Lys Leu Leu Ile
            35                  40                  45

Tyr His Gly Thr Asn Leu Glu Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Val Gln Tyr Ala Gln Phe Pro Trp
                85                  90                  95

Thr Phe Gly Gly Gly Thr Lys Val Glu Ile Lys Arg
            100                 105

<210> SEQ ID NO 26
<211> LENGTH: 108
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: (36)..(36)
<223> OTHER INFORMATION: Y to L
<220> FEATURE:
<221> NAME/KEY: VARIANT
<222> LOCATION: (43)..(43)
<223> OTHER INFORMATION: A to S
<220> FEATURE:
<221> NAME/KEY: VARIANT
<222> LOCATION: (44)..(44)
<223> OTHER INFORMATION: P to F
<220> FEATURE:
<221> NAME/KEY: VARIANT
<222> LOCATION: (46)..(46)
<223> OTHER INFORMATION: L to G
<220> FEATURE:
<221> NAME/KEY: VARIANT
<222> LOCATION: (69)..(69)
<223> OTHER INFORMATION: T to A
<220> FEATURE:
<221> NAME/KEY: VARIANT
<222> LOCATION: (71)..(71)
<223> OTHER INFORMATION: F to Y

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Ser Asp Asn
            20                  25                  30

Ile Gly Trp Tyr Gln Gln Lys Pro Gly Lys Ala Pro Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Val Glu Ile Lys Arg
            100                 105

<210> SEQ ID NO 27
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Ser Asp Asn
            20                  25                  30

Ile Gly Trp Leu Gln Gln Lys Pro Gly Lys Ser Phe Lys Gly Leu Ile

```
                35                  40                  45

Tyr His Gly Thr Asn Leu Glu Asp Gly Val Pro Ser Arg Phe Ser Gly
        50                  55                  60

Ser Gly Ser Gly Ala Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Val Glu Ile Lys Arg
                100                 105

<210> SEQ ID NO 28
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Ser Asp Asn
                20                  25                  30

Ile Gly Trp Leu Gln Gln Lys Pro Gly Lys Ser Phe Lys Leu Leu Ile
            35                  40                  45

Tyr His Gly Thr Asn Leu Glu Asp Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Val Glu Ile Lys
                100                 105

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 32

Gly Phe Asn Ile Lys Asn Thr Tyr Met His
1               5                   10
```

```
<210> SEQ ID NO 33
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 33

Arg Ile Asp Pro Ala Asn Gly His Thr Glu Tyr Ala Pro Lys Phe Gln
1               5                   10                  15

Gly

<210> SEQ ID NO 34
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 34

Val Asp Ser
1

<210> SEQ ID NO 35
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 35

His Ala Ser Gln Gly Ile Ser Asp Asn Ile Gly
1               5                   10

<210> SEQ ID NO 36
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 36

His Gly Thr Asn Leu Glu Asp
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 37

Val Gln Tyr Ala Gln Phe Pro Trp Thr
1               5

<210> SEQ ID NO 38

<400> SEQUENCE: 38

000

<210> SEQ ID NO 39

<400> SEQUENCE: 39
```

```
<210> SEQ ID NO 40
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 40

Glu Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asn Thr
            20                  25                  30

Tyr Met His Trp Val Arg Gln Ala Pro Gly Gln Gly Leu Glu Trp Ile
        35                  40                  45

Gly Arg Ile Asp Pro Ala Asn Lys His Thr Glu Tyr Ala Pro Lys Phe
    50                  55                  60

Leu Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Tyr Tyr Val Ala Ser Trp Gly Gln Gly Thr Thr Val Thr Val Ser Ser
            100                 105                 110

<210> SEQ ID NO 41
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys His Ala Ser Gln Glu Ile Ser Asp Asn
            20                  25                  30

Ile Gly Trp Leu Gln Gln Lys Pro Gly Lys Ser Phe Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Val Glu Ile Lys
            100                 105

<210> SEQ ID NO 42
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 42

Gly Phe Asn Ile Lys Asn Thr Tyr Met His
1               5                   10

<210> SEQ ID NO 43
```

```
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 43

Arg Ile Asp Pro Ala Asn Lys His Thr Glu Tyr Ala Pro Lys Phe Leu
1               5                   10                  15

Gly

<210> SEQ ID NO 44
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 44

Val Ala Ser
1

<210> SEQ ID NO 45
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 45

His Ala Ser Gln Glu Ile Ser Asp Asn Ile Gly
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 46

His Gly Thr Asn Leu Glu Asp
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 47

Val Gln Tyr Ala Gln Phe Pro Trp Thr
1               5

<210> SEQ ID NO 48

<400> SEQUENCE: 48

000

<210> SEQ ID NO 49

<400> SEQUENCE: 49

000
```

<210> SEQ ID NO 50
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 50

Glu Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asn Thr
            20                  25                  30

Tyr Met His Trp Val Arg Gln Ala Pro Gly Gln Gly Leu Glu Trp Ile
        35                  40                  45

Gly Arg Ile Asp Pro Ala Arg Gly His Thr Glu Tyr Ala Pro Lys Phe
    50                  55                  60

Ser Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Tyr Tyr Val Asp Gln Trp Gly Gln Gly Thr Thr Val Thr Val Ser Ser
            100                 105                 110

<210> SEQ ID NO 51
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Asp Asn
            20                  25                  30

Ile Gly Trp Leu Gln Gln Lys Pro Gly Lys Ser Phe Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Val Glu Ile Lys
            100                 105

<210> SEQ ID NO 52
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 52

Gly Phe Asn Ile Lys Asn Thr Tyr Met His
1               5                   10

<210> SEQ ID NO 53
<211> LENGTH: 17
<212> TYPE: PRT

```
<213> ORGANISM: Artificial Sequence
<220> FEATURE:
<223> OTHER INFORMATION: Synthetic polypeptide

<400> SEQUENCE: 53

Arg Ile Asp Pro Ala Arg Gly His Thr Glu Tyr Ala Pro Lys Phe Ser
1               5                   10                  15

Gly

<210> SEQ ID NO 54
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 54

Val Asp Gln
1

<210> SEQ ID NO 55
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 55

His Ala Ser Gln Asp Ile Ser Asp Asn Ile Gly
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 56

His Gly Thr Asn Leu Glu Asp
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 57

Val Gln Tyr Ala Gln Phe Pro Trp Thr
1               5

<210> SEQ ID NO 58

<400> SEQUENCE: 58

000

<210> SEQ ID NO 59

<400> SEQUENCE: 59

000

<210> SEQ ID NO 60
```

<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 60

Glu Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asn Thr
            20                  25                  30

Tyr Met His Trp Val Arg Gln Ala Pro Gly Gln Gly Leu Glu Trp Ile
        35                  40                  45

Gly Arg Ile Asp Pro Ala Arg Gly His Thr Glu Tyr Ala Pro Lys Phe
    50                  55                  60

Glu Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Tyr Tyr Val Ala Ser Trp Gly Gln Gly Thr Thr Val Thr Val Ser Ser
            100                 105                 110

<210> SEQ ID NO 61
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Asp Asn
            20                  25                  30

Ile Gly Trp Leu Gln Gln Lys Pro Gly Lys Ser Phe Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys

-continued

```
210

<210> SEQ ID NO 62
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 62

Gly Phe Asn Ile Lys Asn Thr Tyr Met His
1               5                   10

<210> SEQ ID NO 63
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 63

Arg Ile Asp Pro Ala Arg Gly His Thr Glu Tyr Ala Pro Lys Phe Glu
1               5                   10                  15

Gly

<210> SEQ ID NO 64
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 64

Val Ala Ser
1

<210> SEQ ID NO 65
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 65

His Ala Ser Gln Asp Ile Ser Asp Asn Ile Gly
1               5                   10

<210> SEQ ID NO 66
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 66

His Gly Thr Asn Leu Glu Asp
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 67
```

-continued

```
Val Gln Tyr Ala Gln Phe Pro Trp Thr
1               5
```

<210> SEQ ID NO 68

<400> SEQUENCE: 68

000

<210> SEQ ID NO 69

<400> SEQUENCE: 69

000

<210> SEQ ID NO 70
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 70

```
Glu Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asn Thr
            20                  25                  30

Tyr Met His Trp Val Arg Gln Ala Pro Gly Gln Gly Leu Glu Trp Ile
        35                  40                  45

Gly Arg Ile Asp Pro Ala Lys Gly His Thr Glu Tyr Ala Pro Lys Phe
    50                  55                  60

Leu Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Tyr Tyr Val Asp Val Trp Gly Gln Gly Thr Thr Val Thr Val Ser Ser
            100                 105                 110
```

<210> SEQ ID NO 71
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 71

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Asp Asn
            20                  25                  30

Ile Gly Trp Leu Gln Gln Lys Pro Gly Lys Ser Phe Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Val Glu Ile Lys
            100                 105
```

```
<210> SEQ ID NO 72
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 72

Gly Phe Asn Ile Lys Asn Thr Tyr Met His
1               5                   10

<210> SEQ ID NO 73
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 73

Arg Ile Asp Pro Ala Lys Gly His Thr Glu Tyr Ala Pro Lys Phe Leu
1               5                   10                  15

Gly

<210> SEQ ID NO 74
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 74

Val Asp Val
1

<210> SEQ ID NO 75
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 75

His Ala Ser Gln Asp Ile Ser Asp Asn Ile Gly
1               5                   10

<210> SEQ ID NO 76
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 76

His Gly Thr Asn Leu Glu Asp
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 77

Val Gln Tyr Ala Gln Phe Pro Trp Thr
1               5
```

<210> SEQ ID NO 78

<400> SEQUENCE: 78

000

<210> SEQ ID NO 79

<400> SEQUENCE: 79

000

<210> SEQ ID NO 80
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 80

Glu Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asn Thr
            20                  25                  30

Tyr Met His Trp Val Arg Gln Ala Pro Gly Gln Gly Leu Glu Trp Ile
        35                  40                  45

Gly Arg Ile Asp Pro Ala Gly Gly His Thr Glu Tyr Ala Pro Lys Phe
    50                  55                  60

Ile Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Tyr Tyr Val Ala Ser Trp Gly Gln Gly Thr Thr Val Thr Val Ser Ser
            100                 105                 110

<210> SEQ ID NO 81
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys His Ala Ser Gln Glu Ile Ser Asp Asn
            20                  25                  30

Ile Gly Trp Leu Gln Gln Lys Pro Gly Lys Ser Phe Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Val Glu Ile Lys
            100                 105

<210> SEQ ID NO 82

```
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 82

Gly Phe Asn Ile Lys Asn Thr Tyr Met His
1               5                   10

<210> SEQ ID NO 83
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 83

Arg Ile Asp Pro Ala Gly Gly His Thr Glu Tyr Ala Pro Lys Phe Ile
1               5                   10                  15

Gly

<210> SEQ ID NO 84
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 84

Val Ala Ser
1

<210> SEQ ID NO 85
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 85

His Ala Ser Gln Glu Ile Ser Asp Asn Ile Gly
1               5                   10

<210> SEQ ID NO 86
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 86

His Gly Thr Asn Leu Glu Asp
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 87

Val Gln Tyr Ala Gln Phe Pro Trp Thr
1               5
```

<210> SEQ ID NO 88

<400> SEQUENCE: 88

000

<210> SEQ ID NO 89

<400> SEQUENCE: 89

000

<210> SEQ ID NO 90
<211> LENGTH: 442
<212> TYPE: PRT
<213> ORGANISM: Artificial Sequence
<220> FEATURE:
<223> OTHER INFORMATION: Synthetic polypeptide

<400> SEQUENCE: 90

```
Glu Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asn Thr
            20                  25                  30

Tyr Met His Trp Val Arg Gln Ala Pro Gly Gln Gly Leu Glu Trp Ile
        35                  40                  45

Gly Arg Ile Asp Pro Ala Lys Gly His Thr Glu Tyr Ala Pro Lys Phe
    50                  55                  60

Leu Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Tyr Tyr Val Asp Val Trp Gly Gln Gly Thr Thr Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300
```

```
His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440
```

<210> SEQ ID NO 91
<211> LENGTH: 441
<212> TYPE: PRT
<213> ORGANISM: Artificial Sequence
<220> FEATURE:
<223> OTHER INFORMATION: Synthetic polypeptide

<400> SEQUENCE: 91

```
Glu Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asn Thr
            20                  25                  30

Tyr Met His Trp Val Arg Gln Ala Pro Gly Gln Gly Leu Glu Trp Ile
        35                  40                  45

Gly Arg Ile Asp Pro Ala Lys Gly His Thr Glu Tyr Ala Pro Lys Phe
    50                  55                  60

Leu Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Tyr Tyr Val Asp Val Trp Gly Gln Gly Thr Thr Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220
```

```
Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser His Glu Asp Pro Glu Val Lys Phe Asn Trp
        260                 265                 270

Tyr Val Asp Gly Val Glu Val His Asn Ala Lys Thr Lys Pro Arg Glu
    275                 280                 285

Glu Gln Tyr Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
            325                 330                 335

Gln Pro Arg Glu Pro Gln Val Tyr Thr Leu Pro Pro Ser Arg Asp Glu
        340                 345                 350

Leu Thr Lys Asn Gln Val Ser Leu Thr Cys Leu Val Lys Gly Phe Tyr
    355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
            405                 410                 415

Val Phe Ser Cys Ser Val Met His Glu Ala Leu His Asn His Tyr Thr
        420                 425                 430

Gln Lys Ser Leu Ser Leu Ser Pro Gly
            435                 440

<210> SEQ ID NO 92
<211> LENGTH: 442
<212> TYPE: PRT
<213> ORGANISM: Artificial Sequence
<220> FEATURE:
<223> OTHER INFORMATION: Synthetic polypeptide

<400> SEQUENCE: 92

Glu Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asn Thr
            20                  25                  30

Tyr Met His Trp Val Arg Gln Ala Pro Gly Gln Gly Leu Glu Trp Ile
        35                  40                  45

Gly Arg Ile Asp Pro Ala Lys Gly His Thr Glu Tyr Ala Pro Lys Phe
    50                  55                  60

Leu Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
            85                  90                  95

Tyr Tyr Val Asp Val Trp Gly Gln Gly Thr Thr Val Thr Val Ser Ser
        100                 105                 110

Ala Ser Thr Lys Gly Pro Ser Val Phe Pro Leu Ala Pro Ser Ser Lys
    115                 120                 125

Ser Thr Ser Gly Gly Thr Ala Ala Leu Gly Cys Leu Val Lys Asp Tyr
130                 135                 140
```

-continued

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
            165                 170                 175

Leu Ser Ser Val Val Thr Val Pro Ser Ser Ser Leu Gly Thr Gln Thr
        180                 185                 190

Tyr Ile Cys Asn Val Asn His Lys Pro Ser Asn Thr Lys Val Asp Lys
            195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 93
<211> LENGTH: 441
<212> TYPE: PRT
<213> ORGANISM: Artificial Sequence
<220> FEATURE:
<223> OTHER INFORMATION: Synthetic polypeptide

<400> SEQUENCE: 93

Glu Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asn Thr
            20                  25                  30

Tyr Met His Trp Val Arg Gln Ala Pro Gly Gln Gly Leu Glu Trp Ile
        35                  40                  45

Gly Arg Ile Asp Pro Ala Lys Gly His Thr Glu Tyr Ala Pro Lys Phe
    50                  55                  60

```
Leu Gly Arg Val Thr Ile Thr Ala Asp Glu Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Tyr Tyr Val Asp Val Trp Gly Gln Gly Thr Thr Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly
        435                 440

<210> SEQ ID NO 94
<211> LENGTH: 442
<212> TYPE: PRT
<213> ORGANISM: Artificial Sequence
<220> FEATURE:
```

<223> OTHER INFORMATION: Synthetic polypeptide

<400> SEQUENCE: 94

```
Glu Val Gln Leu Val Gln Ser Gly Ala Glu Val Lys Lys Pro Gly Ser
1               5                   10                  15
Ser Val Lys Val Ser Cys Lys Ala Ser Gly Phe Asn Ile Lys Asn Thr
            20                  25                  30
Tyr Met His Trp Val Arg Gln Ala Pro Gly Gln Gly Leu Glu Trp Ile
        35                  40                  45
Gly Arg Ile Asp Pro Ala Lys Gly His Thr Glu Tyr Ala Pro Lys Phe
    50                  55                  60
Leu Gly Arg Val Thr Ile Thr Ala Asp Glu Ser Thr Asn Thr Ala Tyr
65                  70                  75                  80
Met Glu Leu Ser Ser Leu Arg Ser Glu Asp Thr Ala Val Tyr Tyr Cys
                85                  90                  95
Tyr Tyr Val Asp Val Trp Gly Gln Gly Thr Thr Val Thr Val Ser Ser
            100                 105                 110
Ala Ser Thr Lys Gly Pro Ser Val Phe Pro Leu Ala Pro Ser Ser Lys
        115                 120                 125
Ser Thr Ser Gly Gly Thr Ala Ala Leu Gly Cys Leu Val Lys Asp Tyr
    130                 135                 140
Phe Pro Glu Pro Val Thr Val Ser Trp Asn Ser Gly Ala Leu Thr Ser
145                 150                 155                 160
Gly Val His Thr Phe Pro Ala Val Leu Gln Ser Ser Gly Leu Tyr Ser
                165                 170                 175
Leu Ser Ser Val Val Thr Val Pro Ser Ser Leu Gly Thr Gln Thr
            180                 185                 190
Tyr Ile Cys Asn Val Asn His Lys Pro Ser Asn Thr Lys Val Asp Lys
        195                 200                 205
Lys Val Glu Pro Lys Ser Cys Asp Lys Thr His Thr Cys Pro Pro Cys
    210                 215                 220
Pro Ala Pro Glu Ala Ala Gly Gly Pro Ser Val Phe Leu Phe Pro Pro
225                 230                 235                 240
Lys Pro Lys Asp Thr Leu Met Ile Ser Arg Thr Pro Glu Val Thr Cys
                245                 250                 255
Val Val Val Asp Val Ser His Glu Asp Pro Glu Val Lys Phe Asn Trp
            260                 265                 270
Tyr Val Asp Gly Val Glu Val His Asn Ala Lys Thr Lys Pro Arg Glu
        275                 280                 285
Glu Gln Tyr Asn Ser Thr Tyr Arg Val Val Ser Val Leu Thr Val Leu
    290                 295                 300
His Gln Asp Trp Leu Asn Gly Lys Glu Tyr Lys Cys Lys Val Ser Asn
305                 310                 315                 320
Lys Ala Leu Pro Ala Pro Ile Glu Lys Thr Ile Ser Lys Ala Lys Gly
                325                 330                 335
Gln Pro Arg Glu Pro Gln Val Tyr Thr Leu Pro Pro Ser Arg Glu Glu
            340                 345                 350
Met Thr Lys Asn Gln Val Ser Leu Thr Cys Leu Val Lys Gly Phe Tyr
        355                 360                 365
Pro Ser Asp Ile Ala Val Glu Trp Glu Ser Asn Gly Gln Pro Glu Asn
    370                 375                 380
Asn Tyr Lys Thr Thr Pro Pro Val Leu Asp Ser Asp Gly Ser Phe Phe
385                 390                 395                 400
```

```
Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 95
<211> LENGTH: 441
<212> TYPE: PRT
<213> ORGANISM: Artificial Sequence
<220> FEATURE:
<223> OTHER INFORMATION: Synthetic polypeptide

<400> SEQUENCE: 95

Glu Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asn Thr
            20                  25                  30

Tyr Met His Trp Val Arg Gln Ala Pro Gly Gln Gly Leu Glu Trp Ile
        35                  40                  45

Gly Arg Ile Asp Pro Ala Lys Gly His Thr Glu Tyr Ala Pro Lys Phe
    50                  55                  60

Leu Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Tyr Tyr Val Asp Val Trp Gly Gln Gly Thr Thr Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320
```

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly
        435                 440

<210> SEQ ID NO 96
<211> LENGTH: 442
<212> TYPE: PRT
<213> ORGANISM: Artificial Sequence
<220> FEATURE:
<223> OTHER INFORMATION: Synthetic polypeptide

<400> SEQUENCE: 96

Glu Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asn Thr
            20                  25                  30

Tyr Met His Trp Val Arg Gln Ala Pro Gly Gln Gly Leu Glu Trp Ile
        35                  40                  45

Gly Arg Ile Asp Pro Ala Lys Gly His Thr Glu Tyr Ala Pro Lys Phe
    50                  55                  60

Leu Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Tyr Tyr Val Asp Val Trp Gly Gln Gly Thr Thr Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

```
Lys Pro Lys Asp Gln Leu Met Ile Ser Arg Thr Pro Glu Val Thr Cys
            245                 250                 255

Val Val Val Asp Val Ser His Glu Asp Pro Glu Val Lys Phe Asn Trp
        260                 265                 270

Tyr Val Asp Gly Val Glu Val His Asn Ala Lys Thr Lys Pro Arg Glu
    275                 280                 285

Glu Gln Tyr Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Leu His Glu Ala Leu His Asn His Tyr Thr
            420                 425                 430

Gln Lys Ser Leu Ser Leu Ser Pro Gly Lys
        435                 440

<210> SEQ ID NO 97
<211> LENGTH: 441
<212> TYPE: PRT
<213> ORGANISM: Artificial Sequence
<220> FEATURE:
<223> OTHER INFORMATION: Synthetic polypeptide

<400> SEQUENCE: 97

Glu Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asn Thr
            20                  25                  30

Tyr Met His Trp Val Arg Gln Ala Pro Gly Gln Gly Leu Glu Trp Ile
        35                  40                  45

Gly Arg Ile Asp Pro Ala Lys Gly His Thr Glu Tyr Ala Pro Lys Phe
    50                  55                  60

Leu Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Tyr Tyr Val Asp Val Trp Gly Gln Gly Thr Thr Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160
```

```
Gly Val His Thr Phe Pro Ala Val Leu Gln Ser Ser Gly Leu Tyr Ser
            165                 170                 175

Leu Ser Ser Val Val Thr Val Pro Ser Ser Leu Gly Thr Gln Thr
        180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Gln Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Leu His Glu Ala Leu His Asn His Tyr Thr
            420                 425                 430

Gln Lys Ser Leu Ser Leu Ser Pro Gly
        435                 440

<210> SEQ ID NO 98
<211> LENGTH: 442
<212> TYPE: PRT
<213> ORGANISM: Artificial Sequence
<220> FEATURE:
<223> OTHER INFORMATION: Synthetic polypeptide

<400> SEQUENCE: 98

Glu Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asn Thr
            20                  25                  30

Tyr Met His Trp Val Arg Gln Ala Pro Gly Gln Gly Leu Glu Trp Ile
        35                  40                  45

Gly Arg Ile Asp Pro Ala Lys Gly His Thr Glu Tyr Ala Pro Lys Phe
    50                  55                  60

Leu Gly Arg Val Thr Ile Thr Ala Asp Glu Ser Thr Asn Thr Ala Tyr
65                  70                  75                  80
```

```
Met Glu Leu Ser Ser Leu Arg Ser Glu Asp Thr Ala Val Tyr Tyr Cys
                85                  90                  95
Tyr Tyr Val Asp Val Trp Gly Gln Gly Thr Thr Val Thr Val Ser Ser
            100                 105                 110
Ala Ser Thr Lys Gly Pro Ser Val Phe Pro Leu Ala Pro Ser Ser Lys
        115                 120                 125
Ser Thr Ser Gly Gly Thr Ala Ala Leu Gly Cys Leu Val Lys Asp Tyr
    130                 135                 140
Phe Pro Glu Pro Val Thr Val Ser Trp Asn Ser Gly Ala Leu Thr Ser
145                 150                 155                 160
Gly Val His Thr Phe Pro Ala Val Leu Gln Ser Ser Gly Leu Tyr Ser
            165                 170                 175
Leu Ser Ser Val Val Thr Val Pro Ser Ser Ser Leu Gly Thr Gln Thr
            180                 185                 190
Tyr Ile Cys Asn Val Asn His Lys Pro Ser Asn Thr Lys Val Asp Lys
        195                 200                 205
Lys Val Glu Pro Lys Ser Cys Asp Lys Thr His Thr Cys Pro Pro Cys
    210                 215                 220
Pro Ala Pro Glu Ala Ala Gly Gly Pro Ser Val Phe Leu Phe Pro Pro
225                 230                 235                 240
Lys Pro Lys Asp Gln Leu Met Ile Ser Arg Thr Pro Glu Val Thr Cys
            245                 250                 255
Val Val Val Asp Val Ser His Glu Asp Pro Glu Val Lys Phe Asn Trp
            260                 265                 270
Tyr Val Asp Gly Val Glu Val His Asn Ala Lys Thr Lys Pro Arg Glu
        275                 280                 285
Glu Gln Tyr Asn Ser Thr Tyr Arg Val Val Ser Val Leu Thr Val Leu
    290                 295                 300
His Gln Asp Trp Leu Asn Gly Lys Glu Tyr Lys Cys Lys Val Ser Asn
305                 310                 315                 320
Lys Ala Leu Pro Ala Pro Ile Glu Lys Thr Ile Ser Lys Ala Lys Gly
            325                 330                 335
Gln Pro Arg Glu Pro Gln Val Tyr Thr Leu Pro Pro Ser Arg Glu Glu
            340                 345                 350
Met Thr Lys Asn Gln Val Ser Leu Thr Cys Leu Val Lys Gly Phe Tyr
        355                 360                 365
Pro Ser Asp Ile Ala Val Glu Trp Glu Ser Asn Gly Gln Pro Glu Asn
    370                 375                 380
Asn Tyr Lys Thr Thr Pro Pro Val Leu Asp Ser Asp Gly Ser Phe Phe
385                 390                 395                 400
Leu Tyr Ser Lys Leu Thr Val Asp Lys Ser Arg Trp Gln Gln Gly Asn
            405                 410                 415
Val Phe Ser Cys Ser Val Leu His Glu Ala Leu His Asn His Tyr Thr
            420                 425                 430
Gln Lys Ser Leu Ser Leu Ser Pro Gly Lys
        435                 440

<210> SEQ ID NO 99
<211> LENGTH: 441
<212> TYPE: PRT
<213> ORGANISM: Artificial Sequence
<220> FEATURE:
<223> OTHER INFORMATION: Synthetic polypeptide

<400> SEQUENCE: 99
```

```
Glu Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asn Thr
            20                  25                  30

Tyr Met His Trp Val Arg Gln Ala Pro Gly Gln Gly Leu Glu Trp Ile
        35                  40                  45

Gly Arg Ile Asp Pro Ala Lys Gly His Thr Glu Tyr Ala Pro Lys Phe
    50                  55                  60

Leu Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Tyr Tyr Val Asp Val Trp Gly Gln Gly Thr Thr Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
            165                 170                 175

Leu Ser Ser Val Val Thr Val Pro Ser Ser Leu Gly Thr Gln Thr
        180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
        210                 215                 220

Pro Ala Pro Glu Ala Ala Gly Gly Pro Ser Val Phe Leu Phe Pro Pro
225                 230                 235                 240

Lys Pro Lys Asp Gln Leu Met Ile Ser Arg Thr Pro Glu Val Thr Cys
            245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
        290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
            325                 330                 335

Gln Pro Arg Glu Pro Gln Val Tyr Thr Leu Pro Pro Ser Arg Glu Glu
        340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
            405                 410                 415

Val Phe Ser Cys Ser Val Leu His Glu Ala Leu His Asn His Tyr Thr
```

-continued

```
                420            425              430

Gln Lys Ser Leu Ser Leu Ser Pro Gly
        435                 440

<210> SEQ ID NO 100
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Asp Asn
            20                  25                  30

Ile Gly Trp Leu Gln Gln Lys Pro Gly Lys Ser Phe Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

ANTI-ALPHA-4-BETA-7 ANTIBODIES

1. SEQUENCE LISTING

The instant application contains a Sequence Listing which has been submitted electronically in ASCII format and is hereby incorporated by reference in its entirety. Said ASCII copy, created on Jul. 16, 2021, is named 483US_SL.txt and is 106,797 bytes in size.

2. TECHNICAL FIELD

The present application pertains to, among other things, novel anti-α4β7 antibodies, polynucleotides encoding the antibodies, methods of making the same, and methods of use of these antibodies.

3. BACKGROUND

Over 37 million people are infected with human immunodeficiency virus (HIV) globally today and the prevalent population continues to grow. Significant progress has been made in the management of HIV with the advent of combination antiretroviral therapy (cART). cART needs to be taken consistently throughout the life of a person living with HIV. cART has risk benefit limitations and moreover, it does not decrease the HIV latent viral reservoir. There is a significant need for improved treatment that is capable of keeping the viral load below the level of detection without needing life-long treatment.

In acute human HIV infection, both high level viral replication and a profound depletion of infected CD4+ T cells are believed to play a central role in the development of immune deficiency associated with HIV infection. α4β7 is a gut-homing integrin expressed on T cells (CD4+ or CD8+), B cells and other immune cells, and plays an important role in the pathogenesis of HIV infection. α4β7 has also been reported to be incorporated into the envelope of HIV when the virions bud from the infected host cells (Guzzo et al., Sci. Immunol., 2017).

The α4β7 integrin is a heterodimeric receptor expressed on T cell subsets, B cells, NK cells and other immune cells. This integrin mediates the lymphocyte trafficking into gut-associated lymphoid tissues (GALT) by binding to its ligand mucosal addressin cell adhesion molecule 1 (MAdCAM-1) expressed on endothelial venules of intestinal mucosa. High α4β7 expressing CD4+ T cells are targets for HIV infection in vitro (Cicala et al., PNAS 2009), which are infected and therefore depleted during acute HIV infection (Sivro et al., Sci Transl Med 2018). α4β7 present in HIV-infected CD4+ cells as well as in HIV virions could mediate their trafficking to GALT (Guzzo et al., Sci Immunol 2017). CD4+ T cells that home to GALT account for the largest HIV reservoir in the body (Brenchley and Douek, Mucosal Immunol 2008) even during anti-retroviral therapy.

4. SUMMARY

The present disclosure provides anti-α4β7 antibodies and binding fragments thereof that specifically bind to human α4β7. The amino acid sequences of exemplary CDRs, as well as the amino acid sequence of the $V_H$ and $V_L$ regions of the heavy and light chains of exemplary anti-α4β7 antibodies are provided in the Detailed Description below.

Polynucleotides comprising nucleotide sequences encoding the anti-α4β7 antibodies of the disclosure are provided herein, as are vectors comprising polynucleotides. Additionally, prokaryotic cells transformed with and eukaryotic cells transfected with a vector comprising a nucleotide sequence encoding a disclosed anti-α4β7 antibody are provided herein, as well as eukaryotic (such as mammalian) host cells engineered to express the nucleotide sequences. Methods of producing antibodies, by culturing host cells and recovering the antibodies are also provided.

The present disclosure provides methods of treating subjects, such as human subjects, diagnosed with HIV infection with an anti-α4β7 antibody. The method generally involves administering to the subject an amount of an anti-α4β7 antibody described herein effective to provide therapeutic benefit. The subject may be diagnosed with any clinical category of HIV infection.

Since the anti-α4β7 antibodies described herein target human α4β7 instead of a viral protein, they provide an advantageous therapeutic approach that does not induce HIV mutation-based resistance mechanisms, which frequently occur with treatments targeting viral proteins due to the high mutation frequency of HIV.

Based on data presented herein, it is expected that the anti-α4β7 antibodies described herein will provide therapeutic benefit to subjects diagnosed with HIV infection.

5. BRIEF DESCRIPTION OF THE DRAWINGS

FIGS. 6A-6F show α4β7 expression analysis on samples from 45 HIV+ individuals and 10 healthy (HIV−) donors. Expression of α4β7 (as % or as levels measured by MESF) on CD4+ and CD8+ T cells was compared among HIV+ and HIV− individuals. Only the comparisons that were significantly different by Mann-Whitney two-tailed test are shown in the figures. T cell populations are abbreviated as: N+=naïve (CD28+CD45RO−), CM=central memory (CD28+CD45RO+CCR7+), TM=transient memory (CD28+CD45RO+CCR7−), EM=effector memory (CD28−CD45RO+), TE=terminal effector (CD28−CD45RO−); MESF=Molecules of Equivalent Soluble Fluorochrome.

Figure 1:
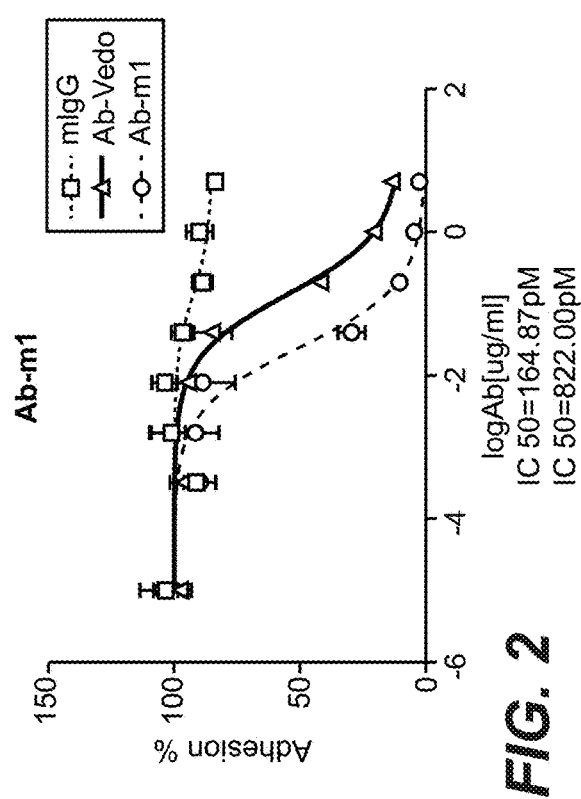
FIG. 1 shows the blockade of adhesion of HuT78 cells to MAdCAM-1 by murine antibody Ab-m1.
Figure 2:
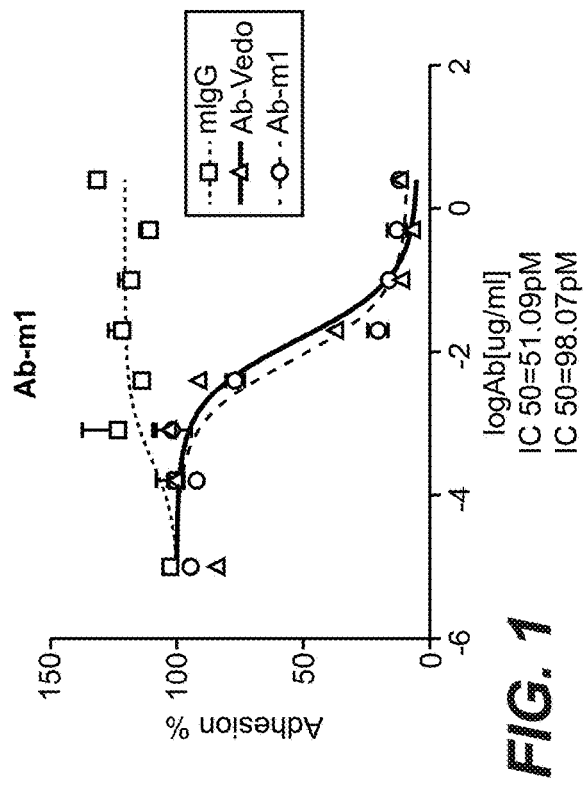
FIG. 2 shows the functional cynomolgus monkey cross-reactivity of Ab-m1 using CHOK1-cα4β7 (cyno α4β7) cell adhesion assay to MAdCAM-1.
Figures 1, 7G:
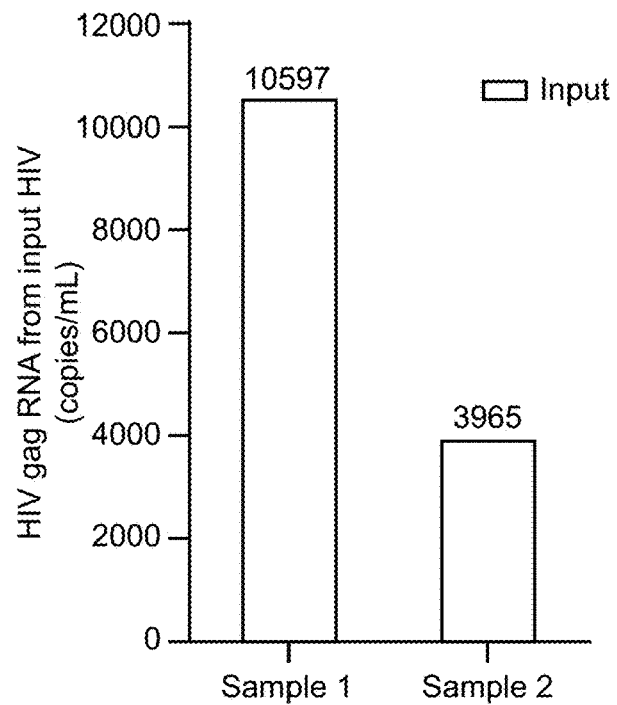
Figures 2, 7G:
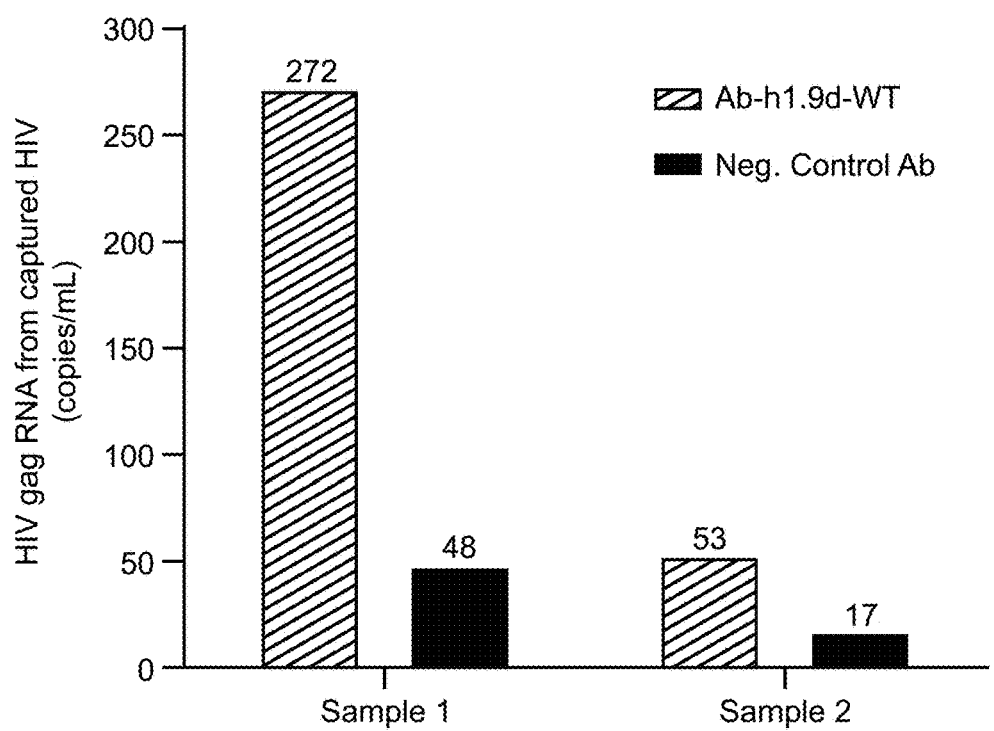
Figure 8A:
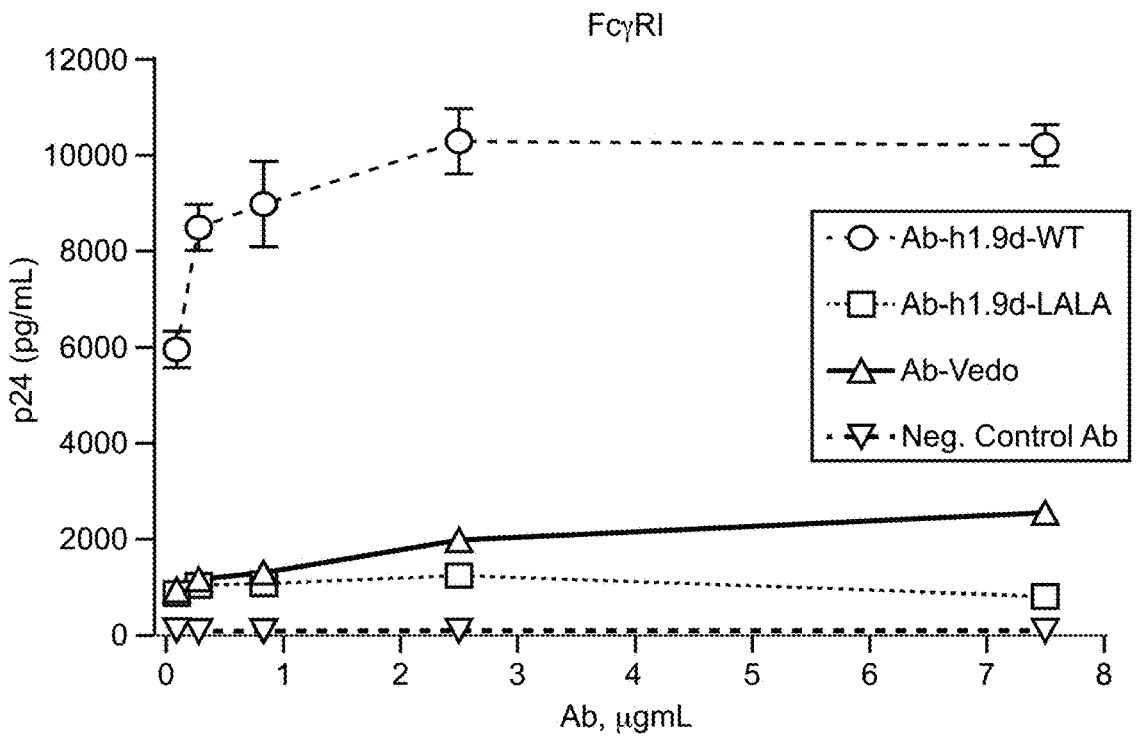
Figure 8B:
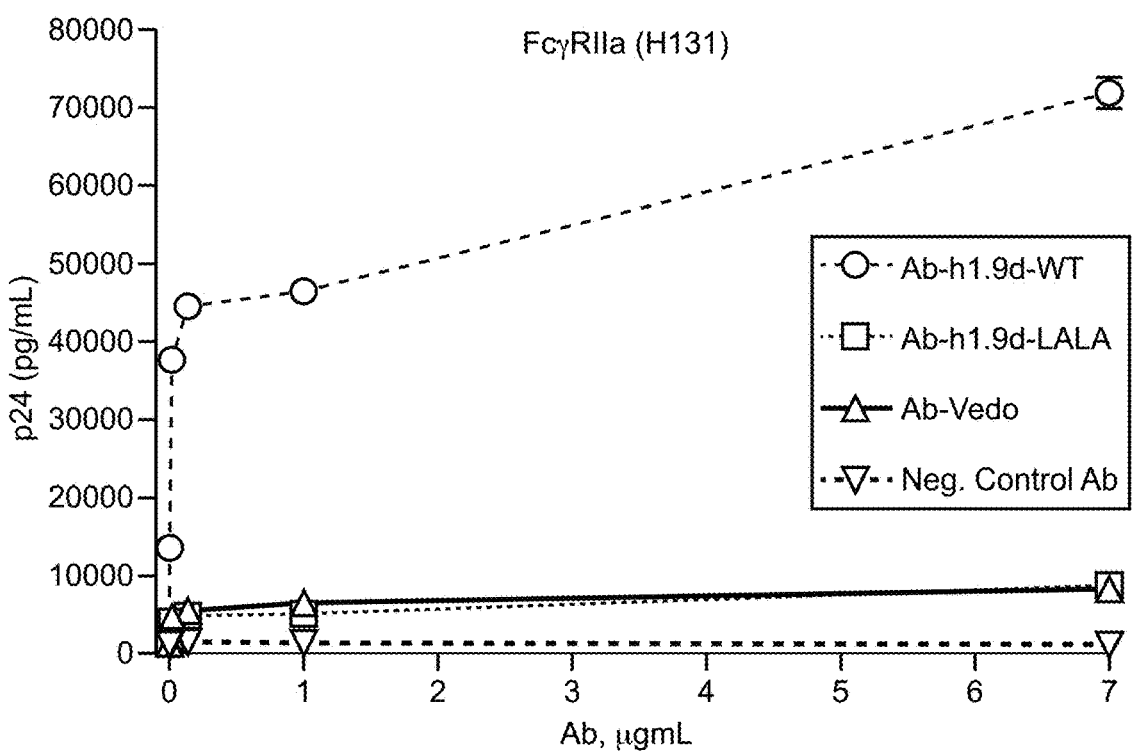
Figure 8C:
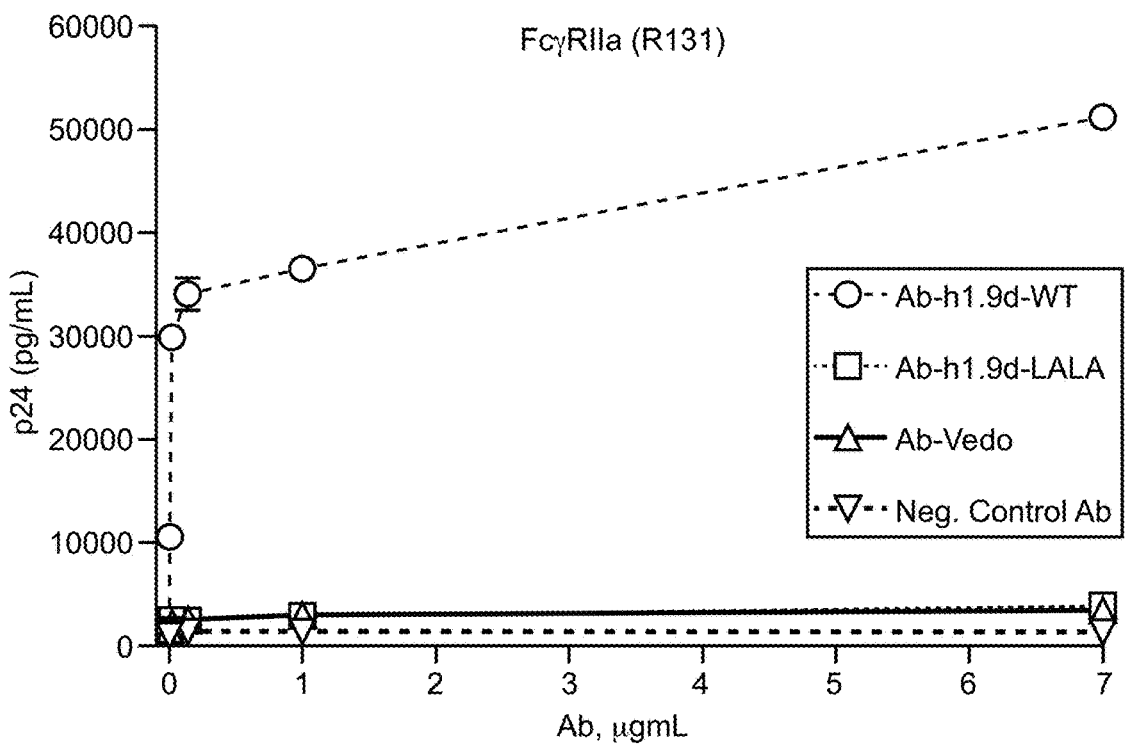
Figure 8D:
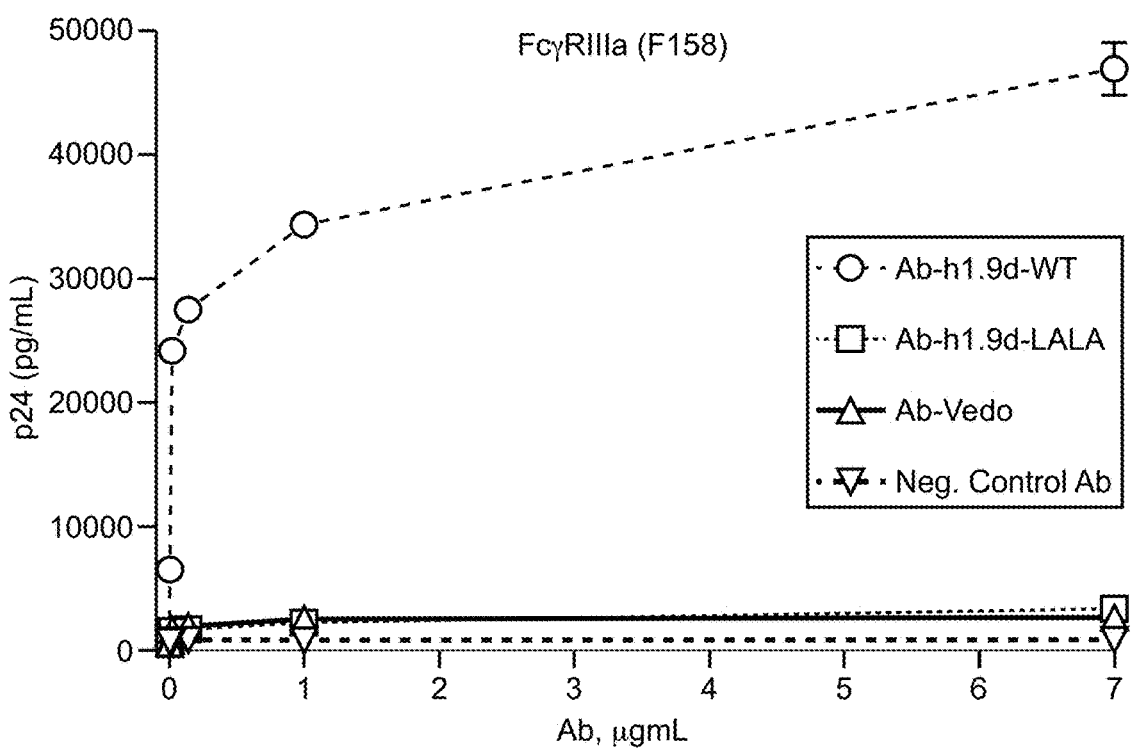
Figure 8E:
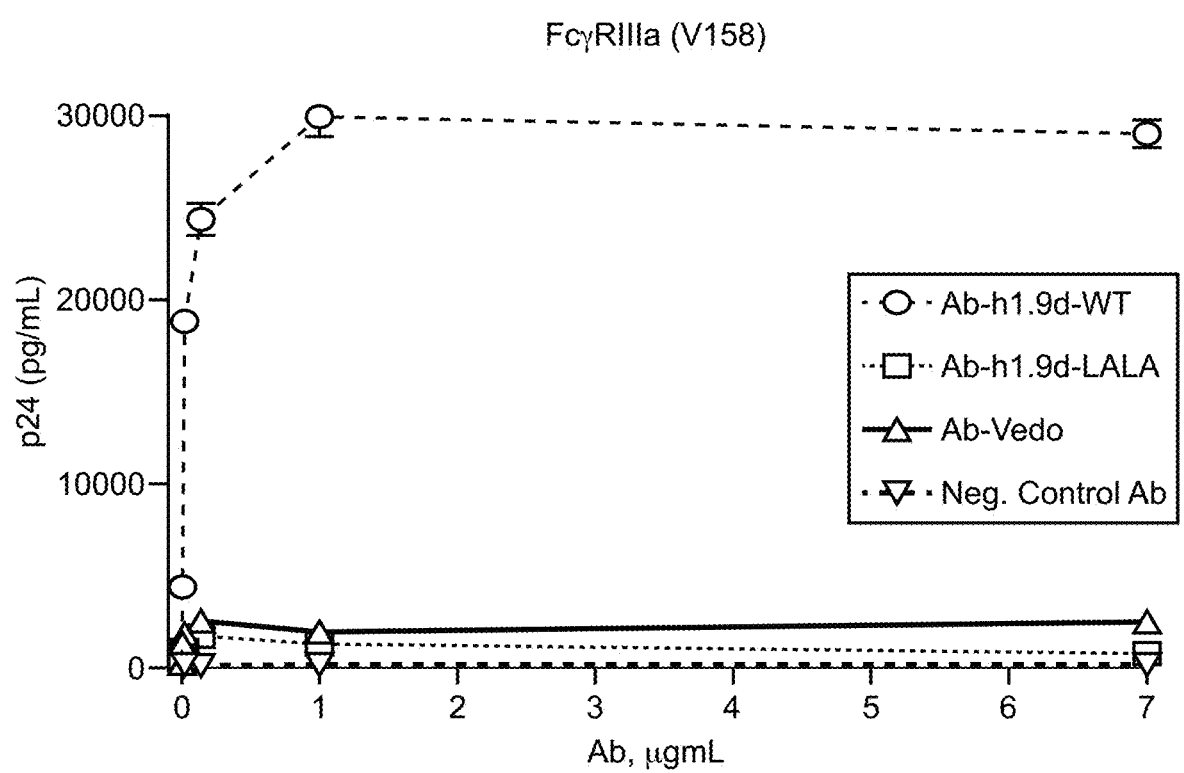

FIGS. 7A-7G-2 show HIV virion capture with Ab-h1.9d-WT. All testing was done with a virion capture assay in a bead format. Ab-h1.9d-WT was tested with six laboratory grown HIV strains (FIGS. 7A-7F) at 5 nM and 15 nM, whereas the negative control antibody was tested at 15 nM only. Amount of HIV p24 gag in the captured samples is shown in pg/mL in 10 µL assayed. Ab-h1.9d-WT was also tested with samples from two HIV-infected individuals with beads coated with 10 µg of the antibody (FIGS. 7G-1 and 7G-2). Amount of HIV gag RNA in the input samples (FIG. 7G-1) and in captured samples (FIG. 7G-2) as detected by digital droplet PCR is shown in copies/mL.

FIGS. 8A-8E shows immune complexes (HIV virions with different antibodies) binding to FcγRs. Immune complexes were first formed by incubating antibodies (Ab-h1.9d-WT, Ab-h1.9d with LALA mutations to significantly reduce FcγR binding, Ab-Vedo, and isotype negative control) with HIV NL4-3, and then captured on FcγRs immobilized on a plate. FcγRI, and FcγRIIIa (V158) were captured on nickel plates, whereas FcγRIIa (H131), FcγRIIa (R131) and FcγRIIIa (F158) were captured on neutravidin plates to increase the sensitivity of the detection. Amount of HIV p24 gag detected is shown in pg/mL in 10 μL assayed. Results of a representative experiment are shown.

Figure 9C:
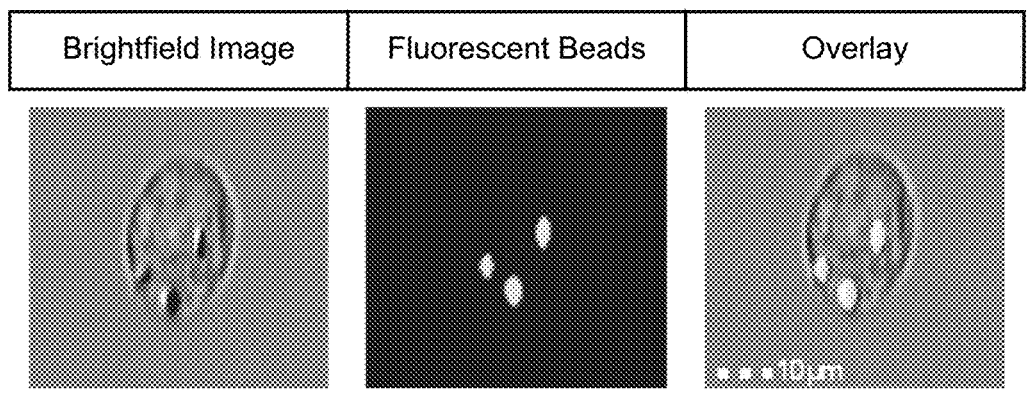

FIGS. 9A-9C show α4β7- and Fc-dependence of Ab-h1.9d-WT-mediated uptake of α4β7-coated beads in THP-1 cells. Phagocytosis scores of immune complexes (containing α4β7 coated beads and the indicated anti-α4β7 or control antibody) in THP-1 cells treated with the complexes for 3 h are plotted. FIG. 9A shows data from one representative experiment. FIG. 9B shows normalized data from 3 independent experiments. Significance was determined using one-way ANOVA coupled to Tukey's multiple comparisons test. **$p<0.0001$, *$p=0.0001$-$0.001$, **$p=0.001$-$0.01$, *$p=0.01$-$0.05$, ns≥$0.05$. FIG. 9C shows representative images of Ab-h1.9d-WT immune complex treated cell with 3 internalized α4β7-coated beads, acquired by imaging cytometry.

Figure 10:
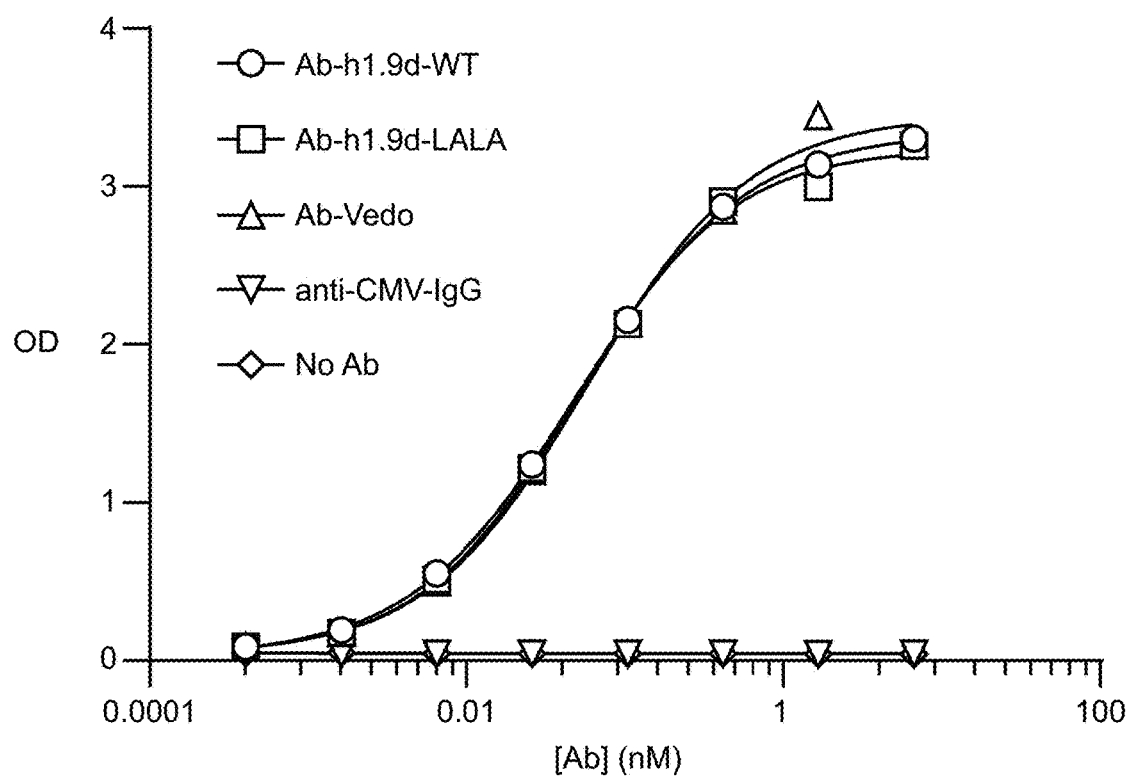

FIG. 10 shows binding of anti-α4β7 antibodies to α4β7+ GFP+VLPs (viral like particles). Binding of Abs to VLPs was determined using ELISA. Ab-h1.9d-WT, Ab-h1.9d-LALA and Ab-Vedo bound to α4β7+GFP+VLPs coated plated with similar EC50 values. Representative data from two independent experiments is shown.

Figure 11A:
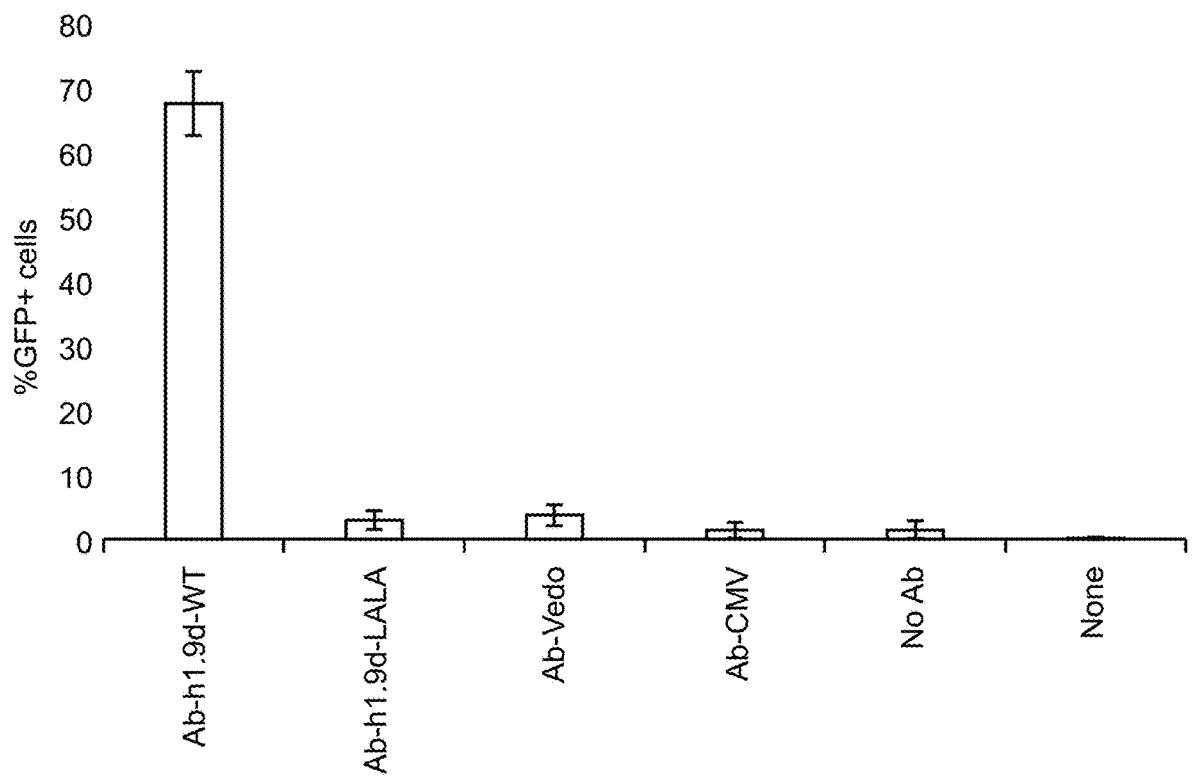
Figure 11B:
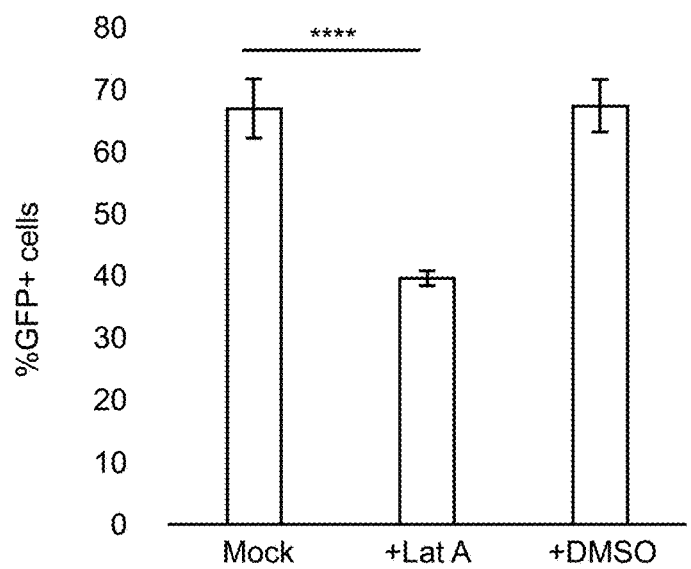

FIGS. 11A-11B show α4β7- and Fc-dependence of Ab-h1.9d-WT-mediated α4β7+GFP+VLP (viral like particles) uptake by THP-1 cells. FIG. 11A shows α4β7+GFP+VLP uptake by THP-1 cells as a percentage of GFP+ cells measured by flow cytometry. FIG. 11B shows inhibition of α4β7+GFP+VLP uptake by Latrunculin A (Lat A). For FIG. 11B, THP-1 cells were pretreated with Lat A for 2 h and then incubated with VLPs and antibodies as in FIG. 11A. Mean±s.d. presented in FIGS. 10A-10B were compiled from 4 and 3 independent experiments, respectively. Significance (****$p=5.4\times10^{-5}$) was calculated by two-tailed student's t-test, where $p<0.05$ is considered significant.

Figure 12A:
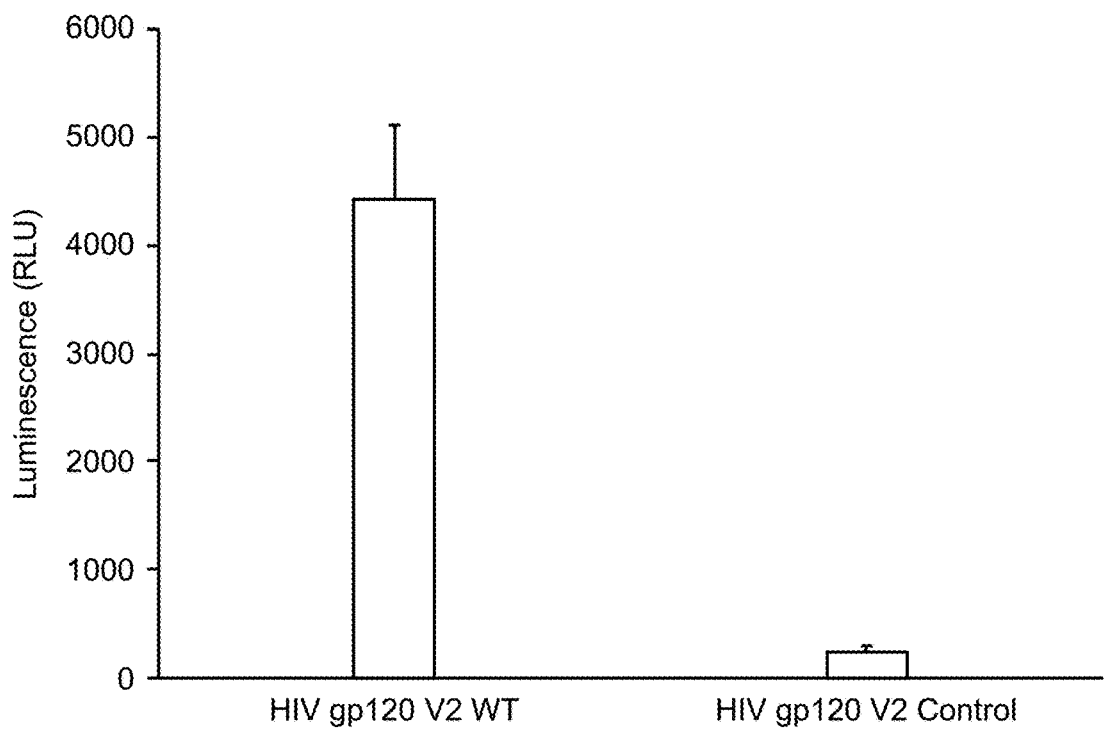
Figure 12B:
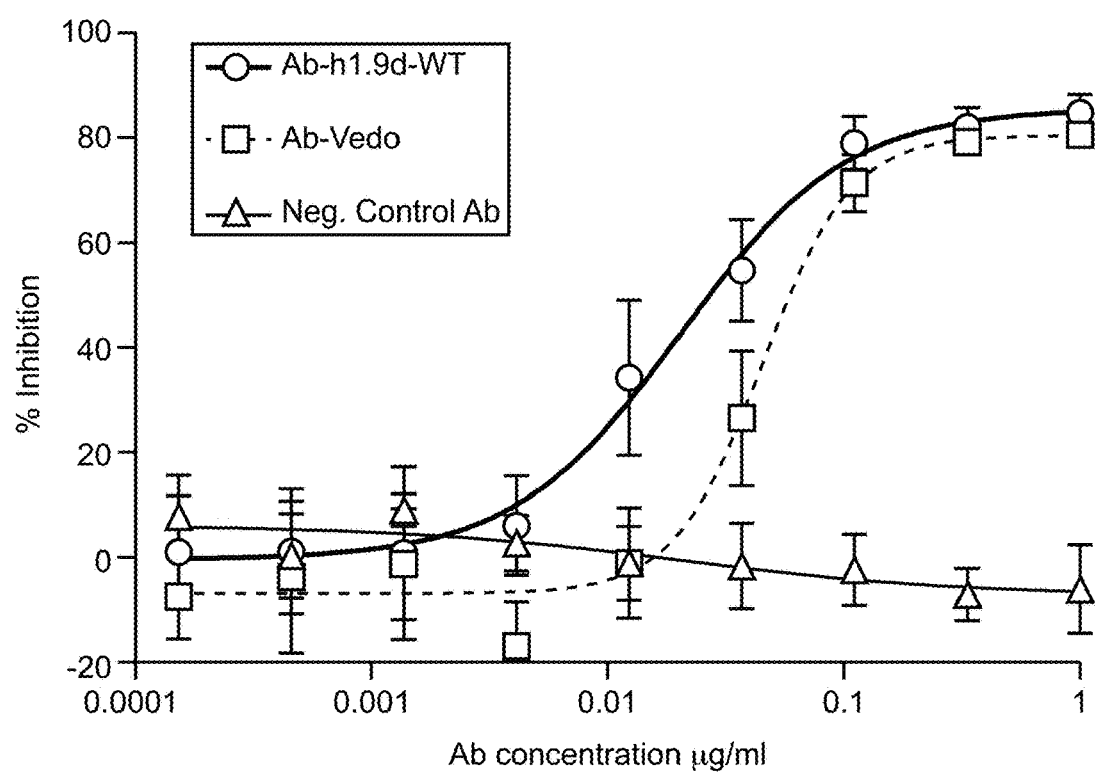

FIGS. 12A-12B show inhibition of interaction of HIV gp120 with α4β7 by different antibodies. FIG. 12A shows binding of RPMI 8866 cells to the HIV gp120-V2 WT peptide, but not the control peptide. RPMI 8866 cells constitutively express α4β7 on the cell surface. HIV gp120 V2 WT peptide and HIV gp120 V2 control peptide were identical in sequence except four amino acids reported to mediate the binding between α4β7 and gp120 were mutated in the control peptide. FIG. 12B shows inhibition of binding of HIV gp120 peptides to RPMI 8866 cells expressing α4β7 by different antibodies. Ab-h1.9d-WT was more potent than Ab-Vedo in inhibiting the binding of HIV gp120-V2 WT peptide to RPMI 8866 cells expressing α4β7.

Figure 13:
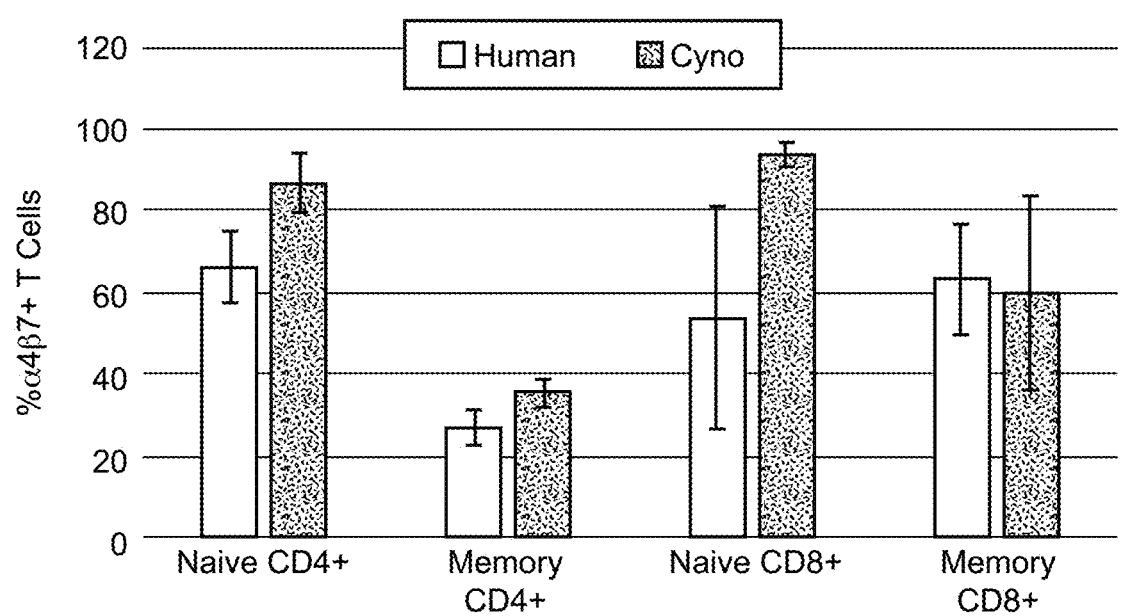

FIG. 13 shows the percentage of human and cynomolgus CD4+ and CD8+ T subsets bound by Ab-h1.9d-WT. The binding of Ab-h1.9d-WT to human and cynomolgus CD4+ and CD8+ T cells was assessed by flow cytometry analysis. The percentage of α4β7+ T cell subsets bound by Ab-h1.9d-WT were determined. The data were obtained from 3 human and 5 cynomolgus donors.

FIGS. 14A-14F show binding specificity of Ab-h1.9d-WT to various integrins. Binding specificity of Ab-h1.9d-WT was assessed on recombinant cells expressing human (14A, 14C and 14E) or cynomolgus integrins (14B, 14D and 14F). Binding to target integrin α4β7 (FIG. 14A/14B) in comparison to α4β1 (FIG. 14C/14D) and αEβ7 (FIG. 14E/14F) integrins. Ab-Nata and etrolizumab-derived Ab-Etro were used as α4 and β7 integrin specific positive controls, respectively and Ab-Ctet as an isotype control. FACS binding results are represented as MFI for titrated mAbs. N=1.

Figure 15:
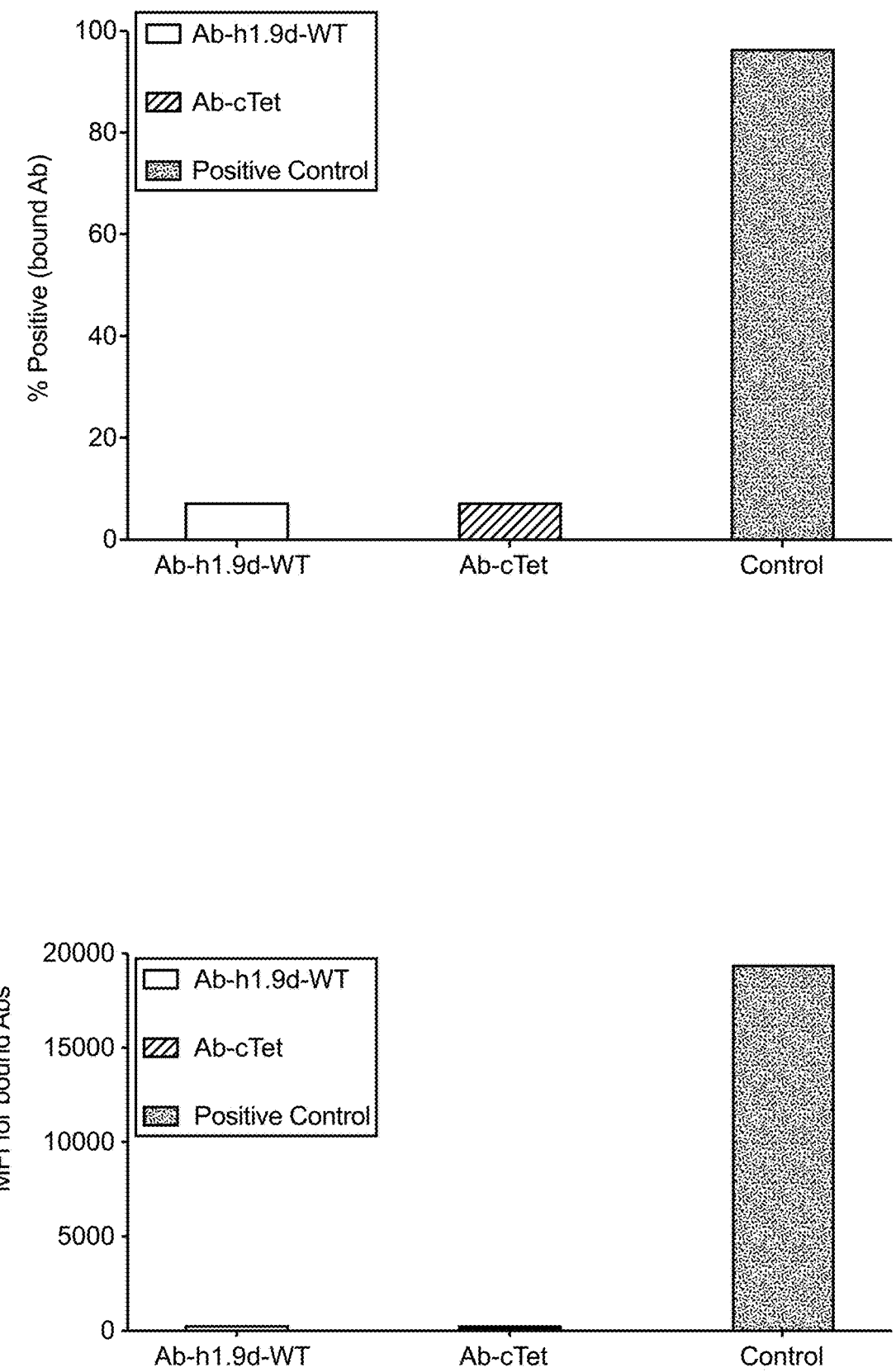

FIG. 15 shows non-specific binding evaluation of Ab-h1.9d-WT in HEK293 cells. Non-specific binding of Ab-h1.9d-WT to HEK293 cells was assessed by flow cytometry analysis. A positive control showed high binding whereas negligible binding was observed for both Ab-h1.9d-WT and isotype control Ab-cTet at 100 μg/mL test concentration. Percentage HEK293 cells bound to test mAbs (A) and MFI of binding intensity by test mAbs (B) are presented. N=2.

Figure 16A:
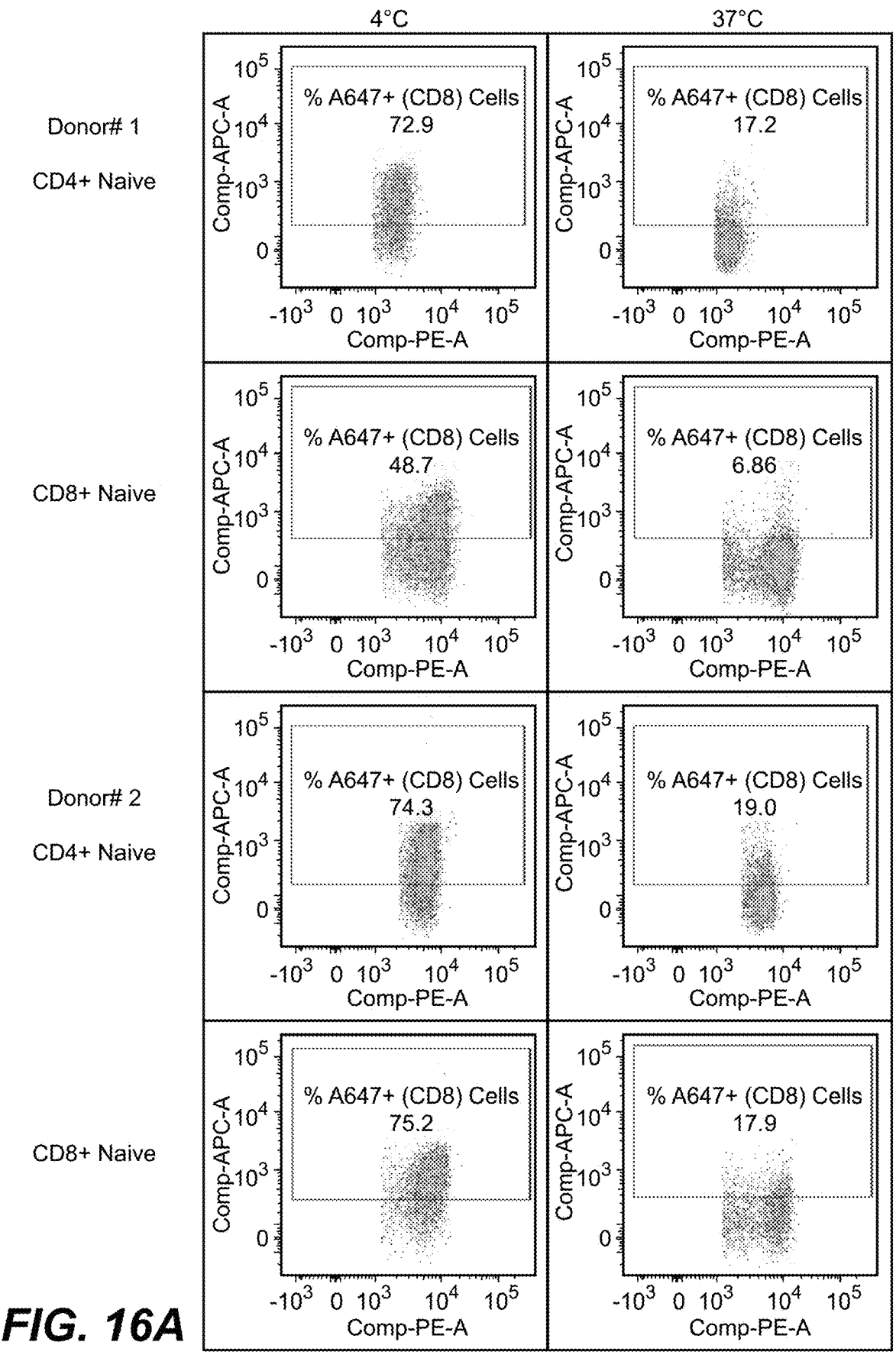
Figure 16B:
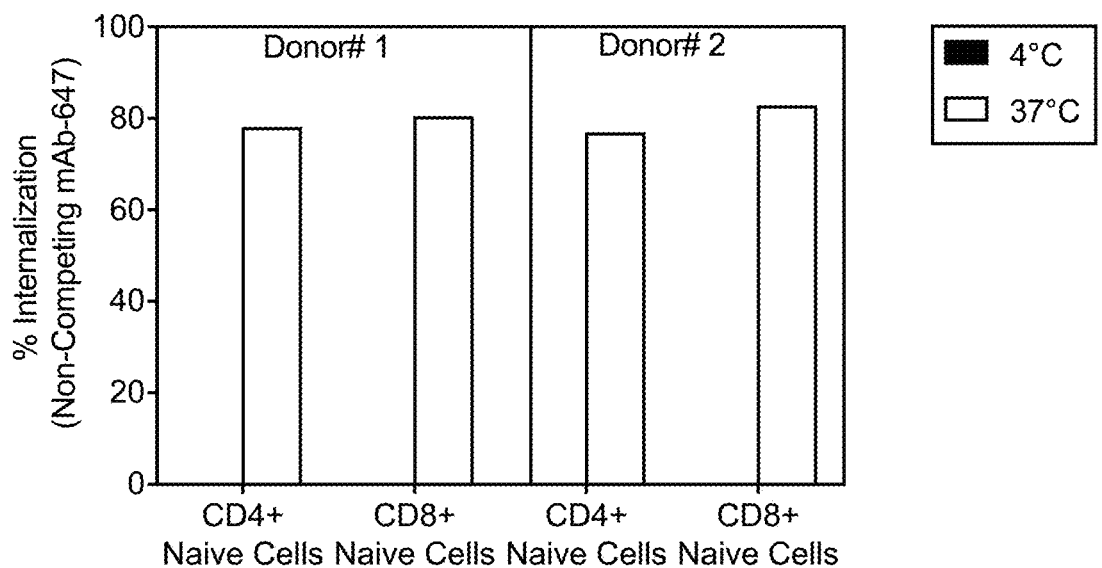

FIGS. 16A-16B show internalization of α4β7 complex with Ab-h1.9d-WT or Ab-Vedo on human primary cells. FIG. 16A shows internalization of Ab-h1.9d-WT on CD4+ T and CD8+ T naïve cells from peripheral blood human donors. Dot plots from two donors indicating the percentage of α4β7 cells upon treatment with Ab-h1.9d-WT at 4 or 37° C. at 18 hours post treatment. The remaining α4β7 on the cell surface was detected with Alexa-647 labeled anti-β7 Ab-Etro. FIG. 16B shows quantification of α4β7 internalization (reduced surface α4β7 expression related to expression observed after treatment at 4° C.) in T cell subsets treated with Ab-h1.9d-WT. (N=two donors). Naive cells were defined as CD45RA+.

Figure 17A:
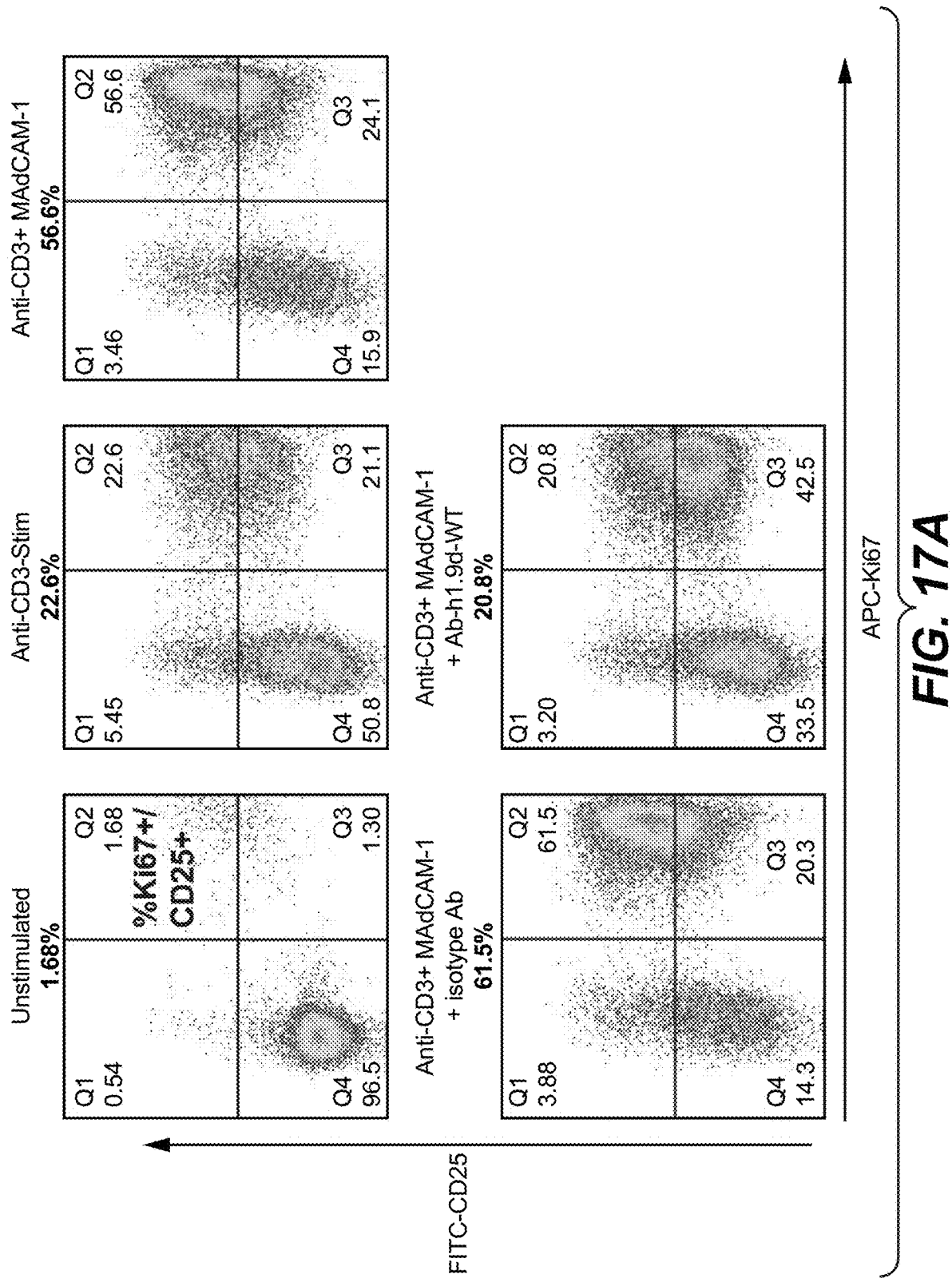
Figure 17B:
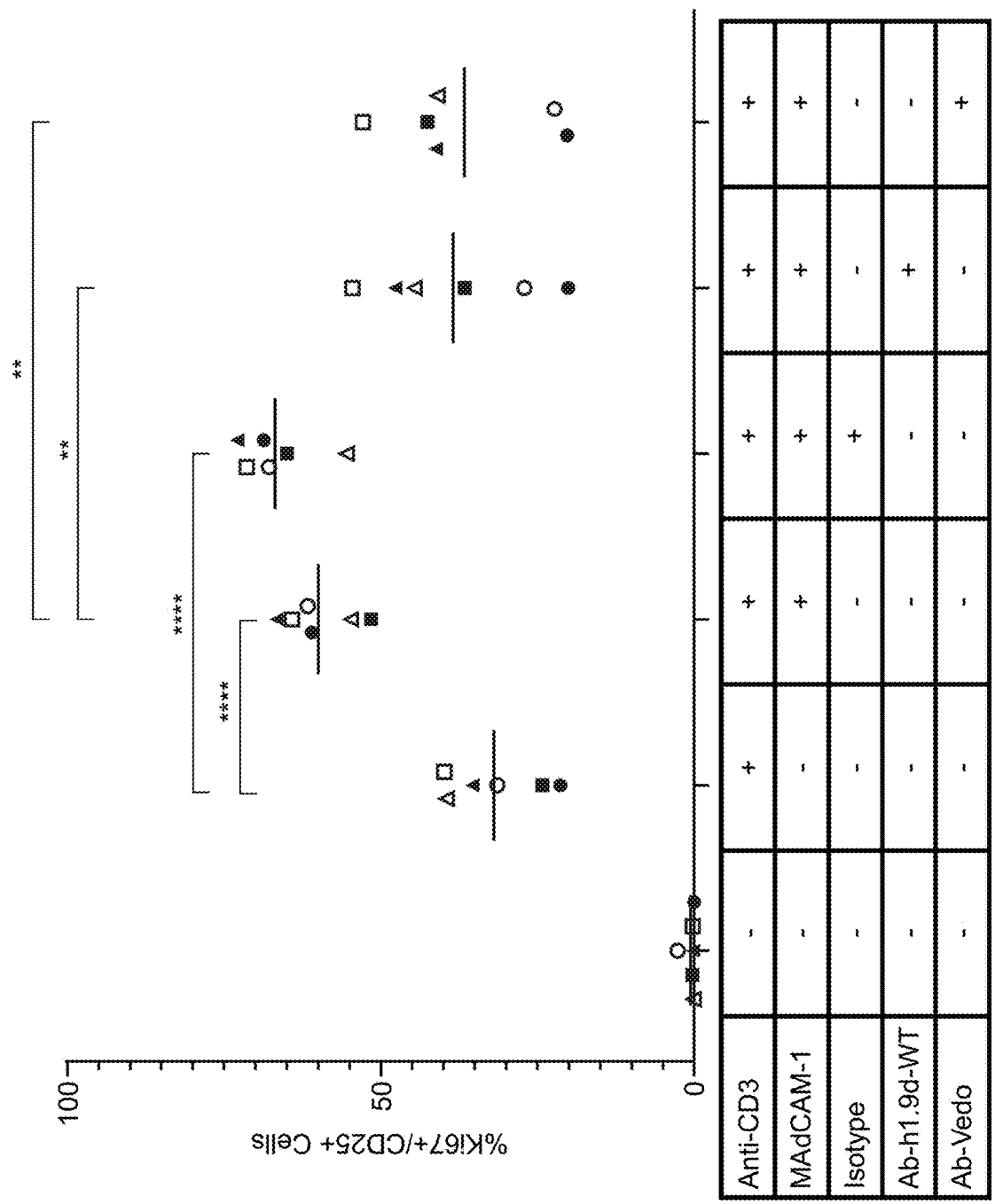

FIGS. 17A-17B show Ab-h1.9d-WT blocks MAdCAM-1 co-stimulation signal on human primary CD4+ T cells. For FIG. 17A, the activation of human primary CD4+ T cells by anti-CD3 and MAdCAM-1 in the presence of isotype control Ab and Ab-h1.9d-WT was measured as percentage of Ki67+CD25+ cells (Ki67+ on X axis, CD25+ on Y axis) by flow cytometry analysis. The data is from a representative donor. For FIG. 17B, the activation of human primary CD4+ T cells by anti-CD3 and MAdCAM-1 in the presence of isotype control Ab, Ab-h1.9d-WT and Ab-Vedo was measured as percentage of Ki67+CD25+ cells (on Y axis). Data is from 6 individual healthy donors. Statistical analysis was performed using two-tailed parametric paired t test: $P<0.01$, **$P<0.0001$).

Figure 18:
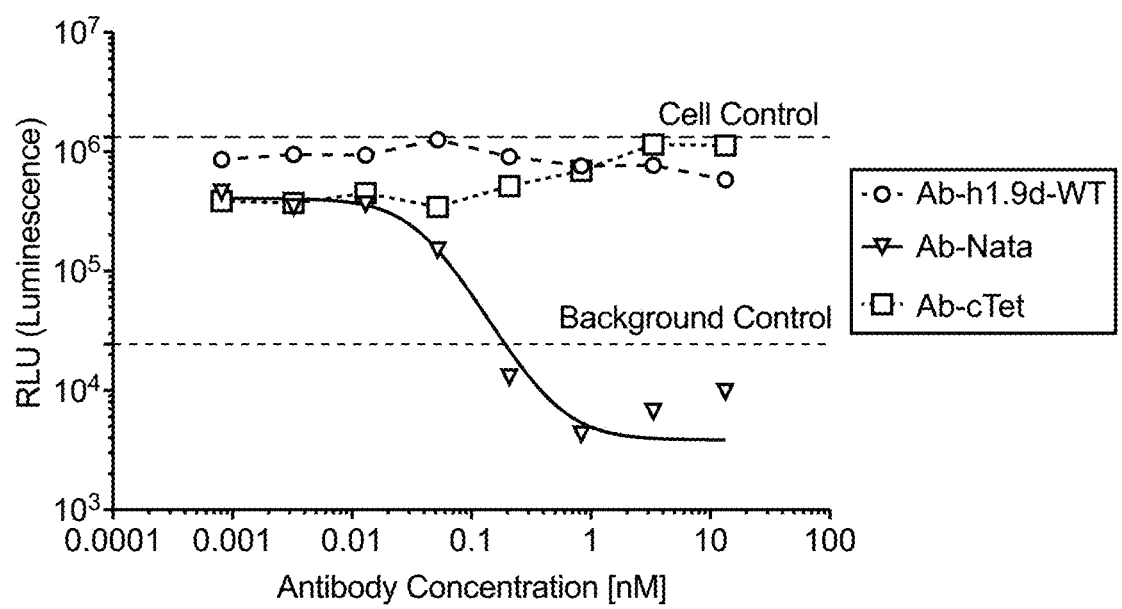

FIG. 18 shows Ab-h1.9d-WT does not block VCAM-1 mediated cell adhesion. Cell adhesion blockade by Ab-h1.9d-WT to VCAM-1 was determined using HuT78 cell adhesion assay. Ab-Nata, an anti-α4 mAb, served as a positive control and Ab-cTet was used as a negative control. Representative data is shown where reduction in luminescence (RLU) indicates decreased cell binding due to ligand blockade. N=3.

Figure 19A:
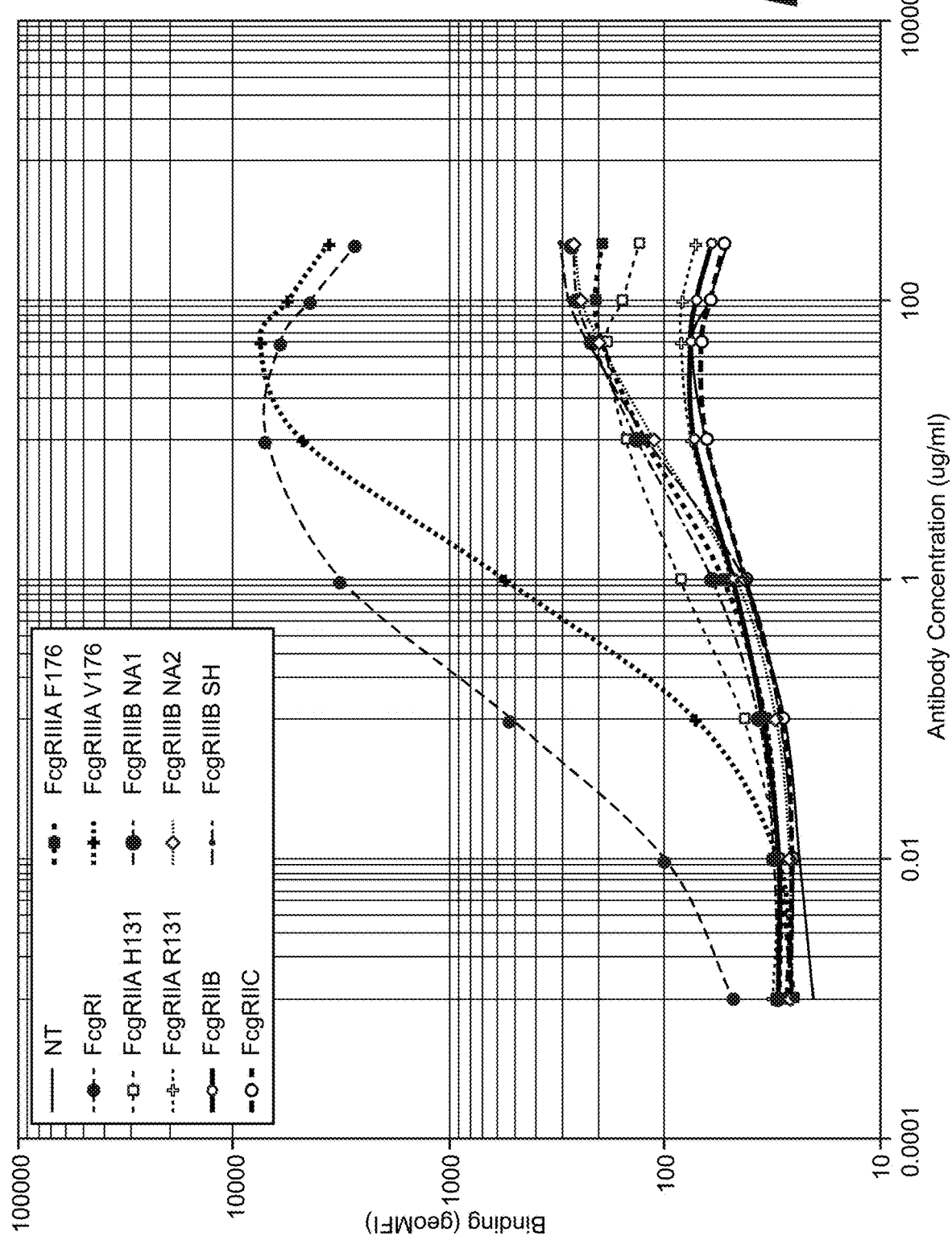
Figure 19B:
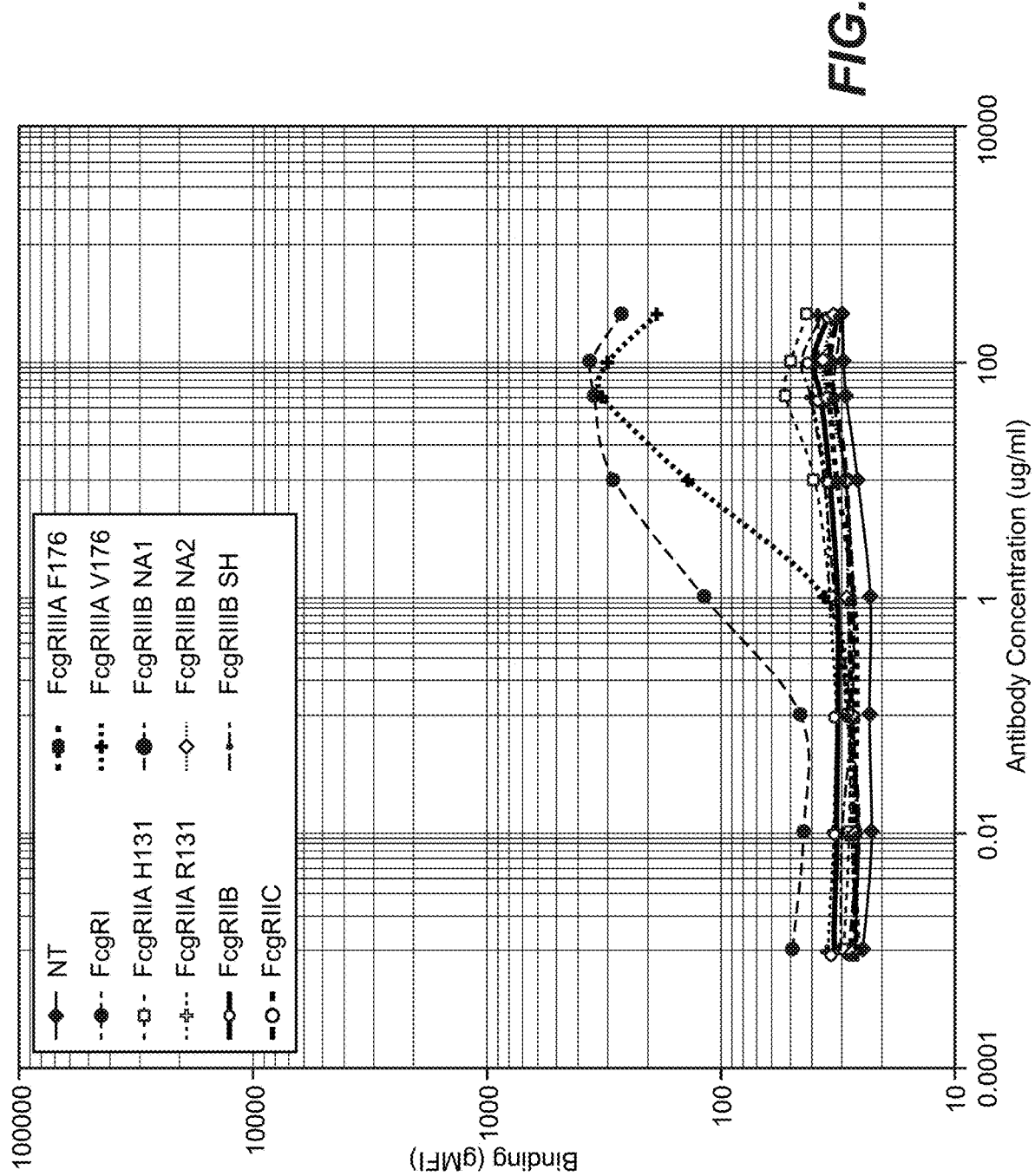

FIGS. 19A-19B show binding of Ab-h1.9d-WT to human FcγR-expressing cells in comparison to Ab-Vedo via flow cytometry. The binding of Ab-h1.9d-WT (FIG. 19A) and Ab-Vedo (FIG. 19B) to human FcγRs was analyzed by using engineered CHO-K1 cells expressing various cell surface human FcγRs and is represented by geometric mean of fluorescence. N=1.

Figure 20A:
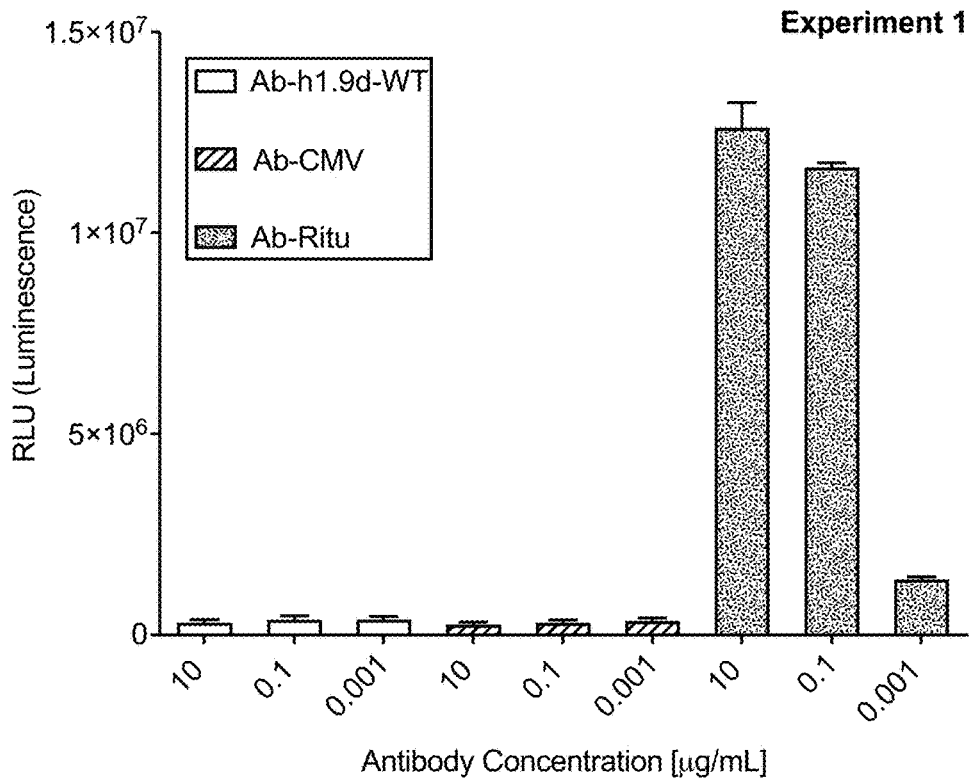
Figure 20A:
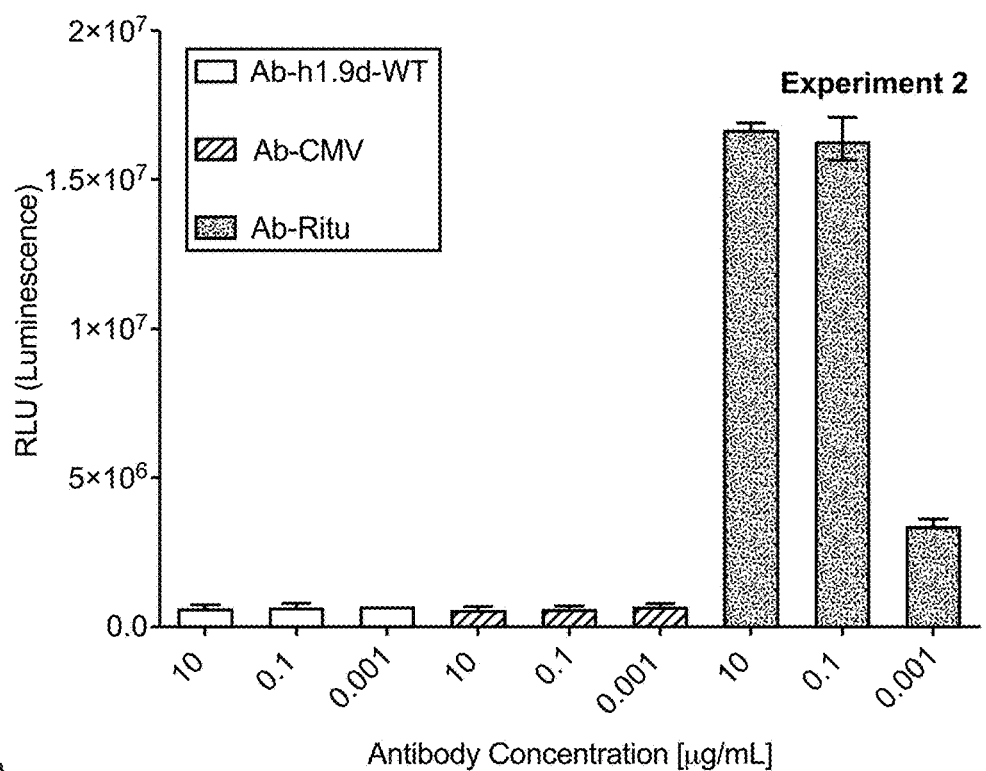
Figure 20B:
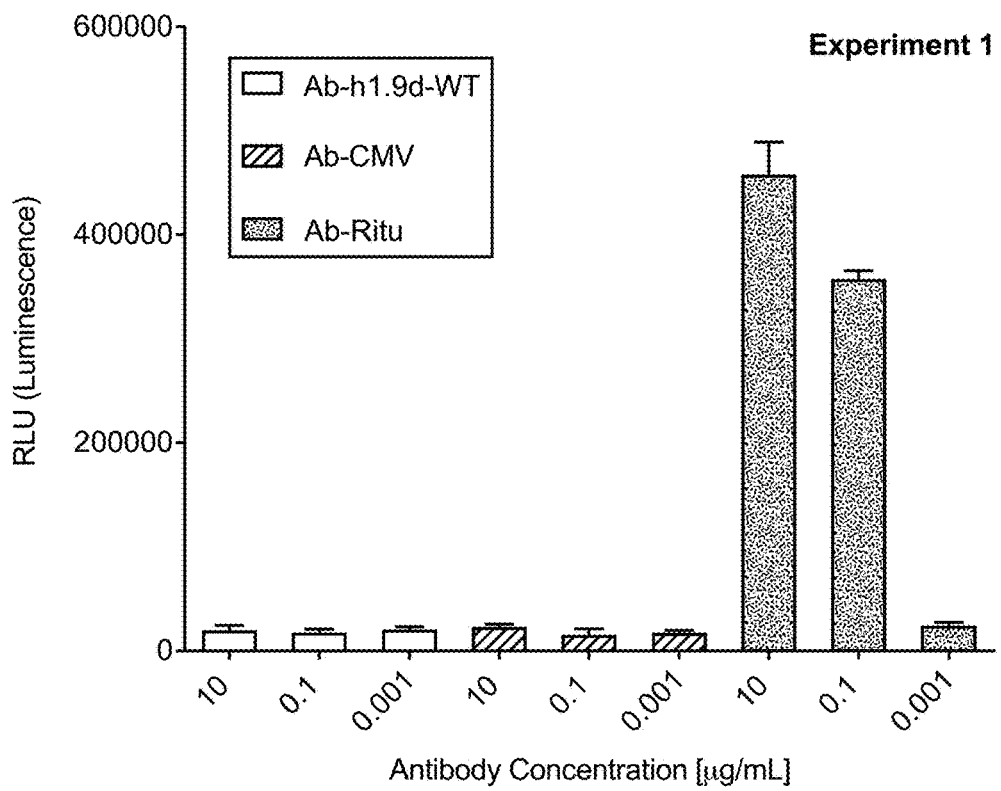
Figure 20B:
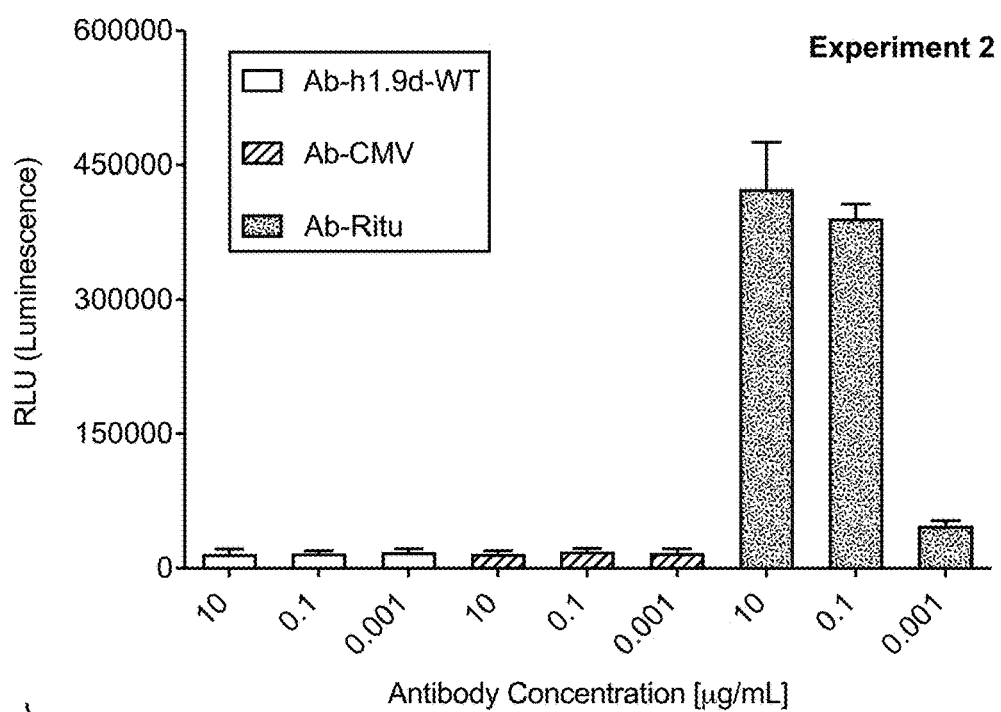

FIGS. 20A-20B show reporter-based ADCC and ADCP activity of Ab-h1.9d-WT. The ability of Ab-h1.9d-WT to induce Fc mediated in vitro ADCC and ADCP activities were assessed by reporter assays (FIG. 20A) ADCC activity using engineered Jurkat human FcγRIIIa V158+ effector reporter cells and RPMI8866 target cells; N=2. (FIG. 20B) ADCP activity using engineered Jurkat human FcγRIIa H131+ effector reporter cells and RPMI8866 target cells; N=2. Ab-Ritu was used as a positive control in the assays. Results are represented by luminescence (RLU); high signal indicates ADCC and ADCP activity.

Figure 21:
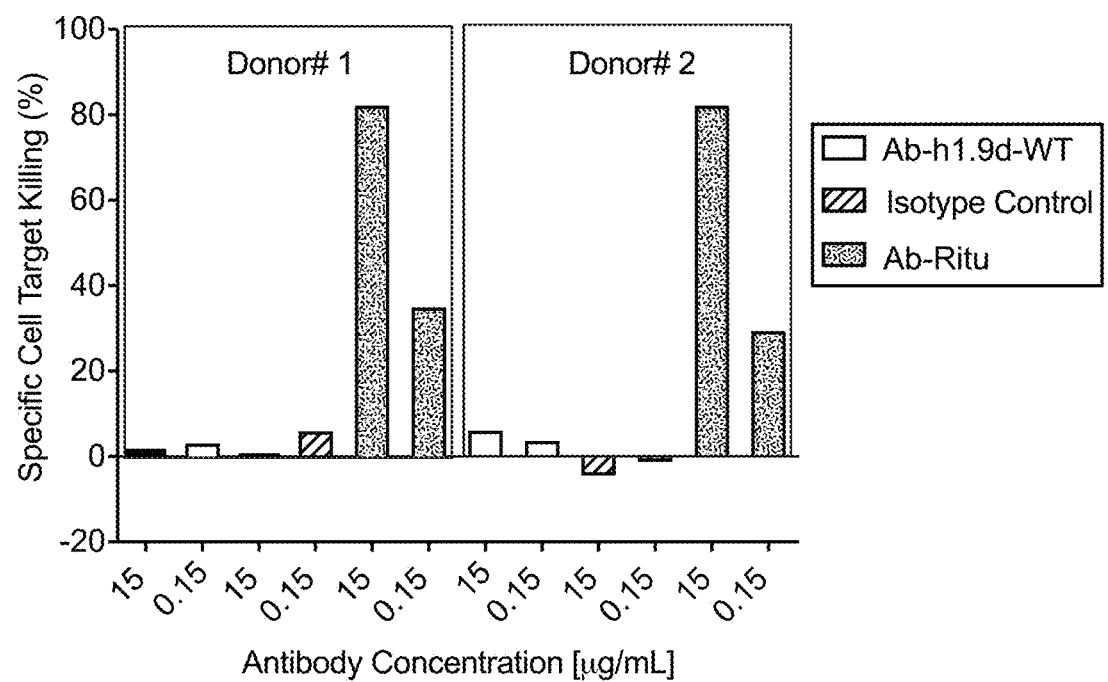

FIG. 21 shows CDC Activity of Ab-h1.9d-WT. The ability of Ab-h1.9d-WT to induce Fc mediated in vitro CDC activity was assessed using RPMI8866 target cells and human serum as the source of complement factors; N=2 donor serum tested. Ab-Ritu was used as a positive control. Results are represented as percentage cell killing; higher cell killing indicates CDC activity.

Figure 22:
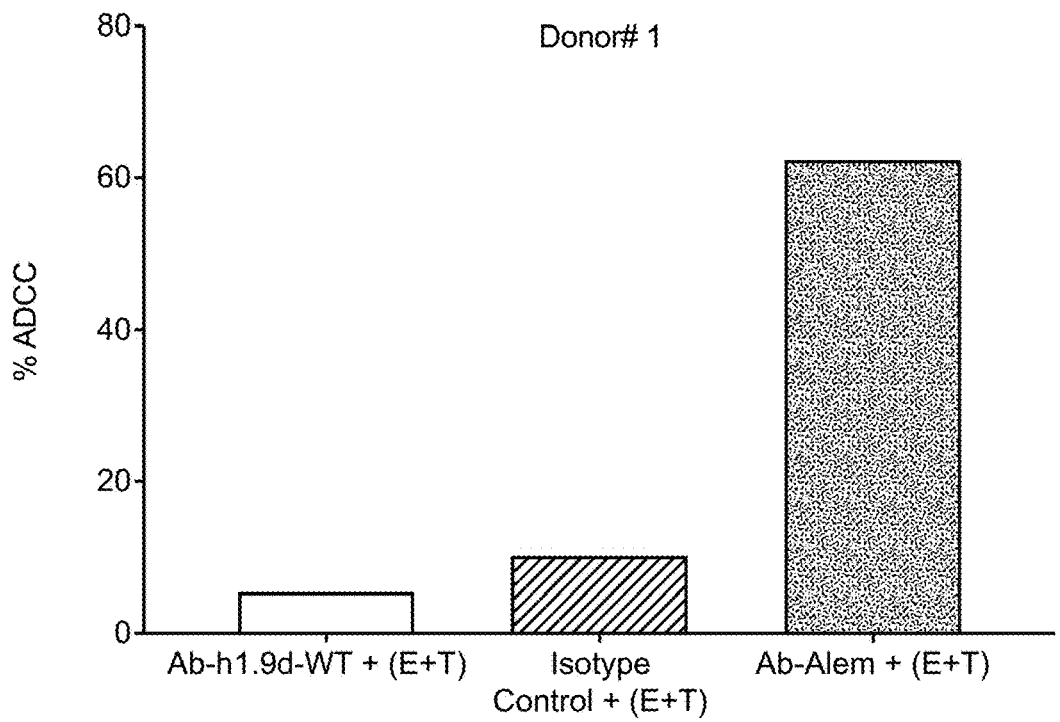
Figure 22:
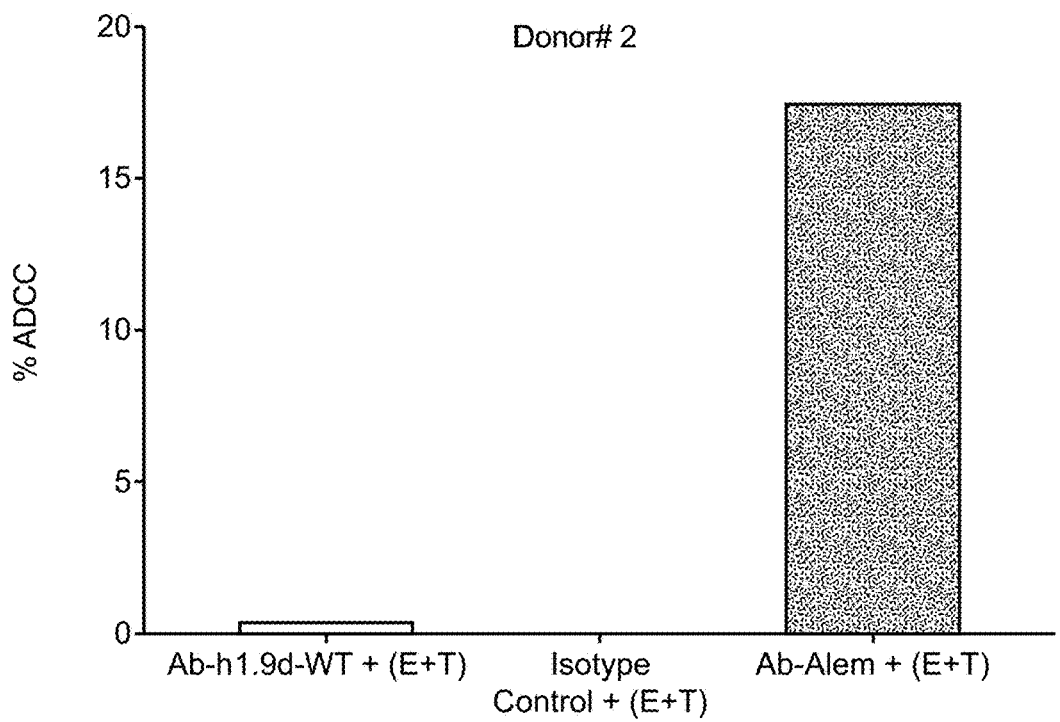

FIG. 22 shows cytotoxicity-based ADCC activity of Ab-h1.9d-WT. The ability of Ab-h1.9d-WT to induce Fc mediated in-vitro ADCC was assessed using HuT78 cells as target cells and human primary NK cells from two donors as effector cells in FACS-based cytotoxicity assay. Target cell killing (cytotoxicity) is represented by percentage ADCC for both donors.

6. DETAILED DESCRIPTION

Without being bound by theory, embodiments of the invention, are hypothesized to exert viral control against HIV infection via two major mechanisms of action: 1) Fab-dependent mechanism: blocking interaction of α4β7 with its ligands such as MAdCAM-1 and HIV gp120, thus inhibiting the co-stimulation of CD4+ T cells mediated by the signaling of these ligands, and suppressing HIV replication in these stimulated cells (Nawaz et al., Mucosal Immunol. 2018, Livia et al., PNAS. 2020), HIV infection of gut tissues (Guzzo et. al., Sci Immunol. 2017), and cell-to-cell viral transmission (Arthos et al. Nat. Immunol. 2008), respectively, and 2) Fc-dependent mechanism: inducing a "vaccination effect" wherein an anti-α4β7 mAb binds to α4β7+HIV virions forming immune-complexes, which are internalized through the interaction of mAb Fc domain with FcγRs on antigen presenting cells (APCs) and processed, and the resulting viral peptides are subsequently presented on the surface of the APCs to elicit new and durable HIV-specific immune responses to suppress viral replication (Parsons et al., Retrovirology 2018; Naranjo-Gomez et al. Curr. Opin. HIV AIDS 2019).

α4β7 integrin is usually in a resting (inactive) state with low affinity for its ligands. Once it is activated, it can bind to its ligands (e.g MAdCAM-1 and gp120) with high-affinity (Ye et al., Blood, 2012; Lertjuthaporn et al., PloS One, 2018). During HIV infection, a motif in the V2 region of HIV gp120 mimics MAdCAM-1 and is capable of binding to α4β7 (Peachman et al., PloS One, 2015). The interaction of α4β7 with gp120 induces the activation of lymphocyte function-associated antigen-1 (LFA-1), potentially inducing the formation of virological synapses and thus enhancing HIV cell-to-cell transmission (Arthos et al. Nat Immunol 2008). Cell-to-cell transmission is critical for promoting viral spread in tissues, and is more important than cell-free virus for viral transmission. Upon binding to α4β7, embodiments of the invention can reduce α4β7-mediated cell-to-cell transmission of HIV by disrupting the interaction of α4β7 with gp120, inducing the internalization of the α4β7-antibody bound complex to the cells, or may inactivate α4β7. Accordingly, the embodiments of the invention demonstrate the ability to inhibit HIV replication and viral spread in tissues.

By targeting the human protein of α4β7 instead of a viral protein, embodiments of the invention do not induce the emergence of viral resistance mutations that are usually associated with a treatment targeting a viral protein due to the high mutation frequency of HIV.

6.1. Abbreviations

The antibodies described herein are, in many embodiments, described by way of their respective polypeptide sequences. Unless indicated otherwise, polypeptide sequences are provided in N→C orientation.

The polynucleotides described herein are, in many embodiments, described by way of their respective polynucleotide sequences. Unless indicated otherwise, polynucleotide sequences in 5'→3' orientation.

For polypeptide sequences, the conventional three or one-letter abbreviations for the genetically encoded amino acids may be used, as noted in TABLE 1, below.

TABLE 1

Encoded Amino Acid Abbreviations

| Amino Acid | Three Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Certain sequences are defined by structural formulae specifying amino acid residues belonging to certain classes (e.g., aliphatic, hydrophobic, etc.). The various classes to which the genetically encoded amino acids belong as used herein are noted in TABLE 2, below. Some amino acids may belong to more than one class. Cysteine, which contains a sulfhydryl group, and proline, which is conformationally constrained, are not assigned classes.

TABLE 2

Encoded Amino Acid Classes

| Class | Amino Acids |
| --- | --- |
| Aliphatic | A, I, L, V |
| Aromatic | F, Y, W |
| Non-Polar | M, A, I, L, V |
| Polar | N, Q, S, T |
| Basic | H, K, R |
| Acidic | D, E |
| Small | A, G |

Abbreviations used throughout the various exemplary embodiments include those provided in TABLE 3, below:

TABLE 3

Abbreviations

| Abbreviations | Definition |
|---|---|
| Ab-h1.9d-WT | Anti-human α4β7 (AC-166667) hu IgG1/k WT mAb |
| Ab-h1.9d-LALA | Anti-human α4β7 hu IgG1/k LALA mAb with reduced binding to human FcγRs |
| α4β7 | Alpha 4 beta 7 integrin |
| α4β7 | Alpha E beta 7 integrin |
| α4β1 | Alpha 4 beta 1 integrin |
| Ab or mAb | Antibody or monoclonal antibody |
| ADCC | Antibody dependent cellular cytotoxicity |
| ADCP | Antibody dependent cellular phagocytosis |
| AF647 | Alexa fluorochrome 647 dye |
| ATI | Antiretroviral treatment interruption |
| APC | Allophycocyanin fluorochrome dye; or Antigen presenting cell |
| BSA | Bovine serum albumin |
| BV421 | Brilliant violet fluorochrome dye |
| Ca | Calcium |
| CDB | Cell dissociation buffer |
| CDC | Complement dependent cytotoxicity |
| CellTrace ™ | Cell proliferation fluorescent dye(s) |
| CFSE | Carboxyfluorescein succinimidyl ester fluorochrome dye |
| CHOK1 | Chinese hamster ovary cell line |
| CM5 | Carboxymethyl-dextran sensor chip used in BIAcore |
| CMV | Cytomegalovirus |
| Conc | Concentration |
| Cyno | Cynomolgus |
| DMEM | Dulbecco's modified eagle's medium |
| DMSO | Dimethyl sulfoxide |
| DPBS | Dulbecco's phosphate buffered saline |
| E | Effector cells |
| $EC_{50}$ | Hail maximal effective concent-cation |
| ECL | Electrochemiluminescent |
| EDTA | Ethylenediaminetetraacetic acid |
| FACS | Fluorescence activated cell sorting |
| FBS | Fetal bovine serum |
| Fc | Fragment crystallizable |
| FcRn | Neonatal Fc receptor |
| Fcγ | Fc gamma |
| FcγR | Fc gamma receptor |
| FcγRIIa | Fc gamma receptor IIa (H131 and R131) |
| FcγRIIb | Fc gamma receptor IIb |
| FcγRIIc | Fc gamma receptor IIc |
| FcγRIIIa | Fc gamma receptor IIIa (F158/176 or V158/176) |
| FcγRIIIb | Fc gamma receptor IIIb (NA1, NA2 and SH) |
| FITC | Fluorescein isothiocyanate fluorochrome dye |
| FVD | Fixable viability fluorochrome dye |
| FMO | Fluorescence Minus One |
| FR | Framework |
| G418 | Geneticin (antibiotic used for stable cell line selection) |
| HBS | Hepes based buffer containing EDTA and NaCl for (HBS-EP) |
| HBSS | Hank's balanced salt solution |
| HEK293 | Human embryonic kidney cell line |
| HER2 | Human epidermal growth factor receptor 2 |
| HI | Heat inactivated |
| hIL-2 | Human interleukin 2 |
| HIV | Human immunodeficiency virus |
| hr | Hour |
| hu Fc | Human Fragment crystallizable |
| HuT78 | Human cutaneous t-cell lymphoma line endogenously expressing α4β7 |
| $IC_{50}$ | Half maximal inhibitoly concentration |
| IgG | Immunoglobulin type G |
| IgG1 | Immunoglobulin type GI |
| IgG1/κ | Human immunoglobulin gamma 1 with kappa light chain |
| EVIDM | Iscove's modified dulbecco's medium |
| $K_D$ | Equilibrium dissociation constant |
| mAb | Monoclonal antibody |
| MES | MES buffer: 2-ethanesulfonic acid |
| MESF | Molecules of equivalent soluble fluorochrome |
| MAdCAM-1 | Mucosal addressin cell adhesion molecule 1 |
| MFI | Mean fluorescence intensity |
| μg | Microgram |
| μL | Microliter |
| mg | Milligram |
| Mg | Magnesium |
| mL | Milliliter |
| mM | Millimolar |
| Min | Minute |
| $MnCl_2$ | Manganese chloride |
| MOA | Mechanism of action |

TABLE 3-continued

Abbreviations

| Abbreviations | Definition |
|---|---|
| MSD | Meso Scale Discovery |
| N | Sample size |
| ND | Not determined |
| NaCl | Sodium chloride |
| nM | Nanomolar |
| NFAT | Nuclear factor of activated T-cells |
| NK | Natural Killer |
| PBMCs | Peripheral blood mononuclear cells |
| PBS | Phosphate buffered saline |
| PE | Phycoerythrin fluorochrome dye |
| PFA | Paraformaldehyde |
| Pg | Picogram |
| PHA | Phytohemagglutinin |
| Puro | Puromycin (antibiotic used for stable cell line selection) |
| RA | Retinoic acid |
| RBC | Research Blood Components |
| $R_{Max}$ | Maximal response-analyte binding capacity by BIAcore |
| RPM | Revolutions per minute |
| RPMI8866 | Human B-cell lymphoma line endogenously expressing α4β7 |
| RLU | Relative luminescence units |
| RT | Room temperature |
| RU | Response in binding used in BIAcore |
| SPR | Surface plasmon resonance allowing real-time binding via BIAcore |
| T | Target cells or T cells |
| VCAM-1 | Vascular cell adhesion molecule 1 |
| WT | Wild type |

6.2. Definitions

Unless otherwise defined herein, scientific and technical terms used in connection with the present disclosure have the meanings that are commonly understood by those of ordinary skill in the art.

As used herein, numbering of antibody amino acid residues is done according to the EU numbering scheme, unless otherwise indicated.

6.3. Anti-α4β7 Antibodies

In one aspect, the disclosure concerns antibodies that specifically bind α4β7 heterodimeric integrin receptor (also known as α4β7, LPAM-1, lymphocyte Peyer's patch adhesion molecule 1, and a dimer of Integrin alpha-4 and Integrin beta-7).

As used herein, the term "antibody" (Ab) refers to an immunoglobulin molecule that specifically binds to a particular antigen, e.g., α4β7. In some embodiments, the anti-α4β7 antibodies of the disclosure bind to human α4β7 and thereby modulate the immune system. Anti-α4β7 antibodies of the disclosure comprise complementarity determining regions (CDRs), also known as hypervariable regions, in both the light chain and the heavy chain variable domains. The more highly conserved portions of variable domains are called the framework (FR). As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The disclosure provides antibodies comprising modifications in these hybrid hypervariable positions. The variable domains of native heavy and light chains each comprise four FR regions, largely by adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the target binding site of antibodies. See Kabat et al., Sequences of Proteins of Immunological Interest (National Institute of Health, Bethesda, Md. 1987).

The antibodies of the disclosure may be polyclonal, monoclonal, genetically engineered, and/or otherwise modified in nature, including but not limited to chimeric antibodies, humanized antibodies, human antibodies, single chain antibodies, etc. In various embodiments, the antibodies comprise all or a portion of a constant region of an antibody. In some embodiments, the constant region is an isotype selected from: IgA (e.g., IgA$_1$ or IgA$_2$), IgD, IgE, IgG (e.g., IgG$_1$, IgG$_2$, IgG$_3$ or IgG$_4$), and IgM. In specific embodiments, the anti-α4β7 antibodies described herein comprise an IgG$_1$. In other embodiments, the anti-α4β7 antibodies comprise an IgG$_2$. In yet other embodiments, the anti-α4β7 antibodies comprise an IgG$_4$. As used herein, the "constant region" of an antibody includes the natural constant region, allotypes or variants, such as any of T250Q, L234A, L235A, D356E, L358M, M428L, and/or A431G in human IgG$_1$.

The light constant region of an anti-α4β7 antibody may be a kappa (κ) light region or a lambda (λ) region. A λ light region can be any one of the known subtypes, e.g., λ$_1$, λ$_2$, λ$_3$, or λ$_4$. In some embodiments, an anti-α4β7 antibody comprises a kappa (κ) light region.

The term "monoclonal antibody" as used herein is not limited to antibodies produced through hybridoma technology. A monoclonal antibody is derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

The term "chimeric" antibody as used herein refers to an antibody having variable sequences derived from a non-human immunoglobulin, such as a rat or a mouse antibody, and human immunoglobulin constant regions, typically chosen from a human immunoglobulin template.

"Humanized" forms of non-human (e.g., murine) antibodies comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence.

"Human antibodies" include antibodies having the amino acid sequence of a human immunoglobulin and include antibodies isolated from human immunoglobulin libraries or from animals transgenic for one or more human immunoglobulins and that do not express endogenous functional immunoglobulins. Human antibodies can be made by a variety of methods known in the art including phage display methods using antibody libraries derived from human immunoglobulin sequences.

Anti-α4β7 antibodies of the disclosure include full-length (intact) antibody molecules.

The anti-α4β7 antibodies may be antibodies whose sequences have been modified to alter at least one constant region-mediated biological effector function. For example, in some embodiments, an anti-α4β7 antibody may be modified to reduce at least one constant region-mediated biological effector function relative to the unmodified antibody, e.g., reduced binding to one or more of the Fc receptors (FcγR) such as FcγRI, FcγRIIa, FcγRIIb, FcγRIIIa and/or FcγRIIIb. FcγR binding can be reduced by mutating the immunoglobulin constant region segment of the antibody at particular regions necessary for FcγR interactions (See, e.g., Canfield and Morrison, 1991, J. Exp. Med. 173:1483-1491; and Lund et al., 1991, J. Immunol. 147:2657-2662). Reduction in FcγR binding ability of the antibody can also reduce other effector functions which rely on FcγR interactions, such as opsonization, phagocytosis and antigen-dependent cellular cytotoxicity ("ADCC").

The anti-α4β7 antibodies described herein include antibodies that have been modified to acquire or improve at least one constant region-mediated biological effector function relative to an unmodified antibody, e.g., to enhance FcγR interactions (See, e.g., US Patent Appl. No. 2006/0134709). For example, an anti-α4β7 antibody of the disclosure can have a constant region that binds FcγRI, FcγRIIa, FcγRIIb, FcγRIIIa and/or FcγRIIIb with greater affinity than the corresponding unmodified constant region.

Additional substitutions that can modify FcγR binding and/or ADCC effector function of an anti-α4β7 antibody include the K322A substitution or the L234A and L235A double substitution in the Fc region. See, e.g., Hezareh, et al. J. Virol., 75 (24): 12161-12168 (2001).

The anti-α4β7 antibodies of the disclosure can comprise modified (or variant) CH2 domains or entire Fc domains that include amino acid substitutions that increase binding to FcγRIIb and/or reduced binding to FcγRIIIa as compared to the binding of a corresponding wild-type CH2 or Fc region. A variant CH2 or variant Fc domain may include one or more substitutions at position 263, position 266, position 273, and position 305. In some embodiments, the anti-α4β7 antibodies comprise one or more substitutions selected from V263L, V266L, V273C, V273E, V273F, V273L, V273M, V273S, V273Y, V305K, and V305W, relative to the wild-type CH2 domain.

Other examples of variant CH2 or variant Fc domains that can afford increased binding to FcγRIIb and/or reduced binding to FcγRIIIa as compared to the binding of a corresponding wild-type CH2 or Fc region include those found in Vonderheide, et al. Clin. Cancer Res., 19(5), 1035-1043 (2013), such as S267E or S267E/L328F in human $IgG_1$.

Anti-α4β7 antibodies that comprise a human $IgG_4$ constant region can comprise the S228P mutation, which has been reported to prevent Fab arm exchange. See, e.g., Silva, J P et al. Journal of Biological Chemistry, 290(9), 5462-5469 (2015).

In some embodiments, the anti-α4β7 antibodies include modifications that increase or decrease their binding affinities to the fetal Fc receptor, FcRn, for example, by mutating the immunoglobulin constant region segment at particular regions involved in FcRn interactions. In particular embodiments, an anti-α4β7 antibody of the IgG class is mutated such that at least one of amino acid residues 250, 314, and 428 of the heavy chain constant region is substituted alone, or in any combinations thereof. For position 250, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. An exemplary substitution known to modify Fc effector function is the Fc substitution M428L, which can occur in combination with the Fc substitution T250Q. Additional specific combinations of suitable amino acid substitutions are identified in Table 1 of U.S. Pat. No. 7,217,797. Such mutations increase binding to FcRn, which protects the antibody from degradation and increases its half-life.

Anti-α4β7 antibodies with high affinity for human α4β7 may be desirable for therapeutic and diagnostic uses. Accordingly, the present disclosure contemplates antibodies having a high binding affinity to human α4β7. In specific embodiments, the anti-α4β7 antibodies binds to human α4β7 with an affinity of at least about 100 nM, but may exhibit higher affinity, for example, at least about 90 nM, 80 nM, 70 nM, 60 nM, 50 nM, 40 nM, 30 nM, 25 nM, 20 nM, 15 nM, 10 nM, 7 nM, 6 nM, 5 nM, 4 nM, 3 nM, 2 nM, 1 nM, 0.1 nM, 0.01 nM, or even higher. In some embodiments, the antibodies bind human α4β7 with an affinity in the range of about 1 pM to about 10 nM, of about 100 pM to about 10 nM, about 100 pM to about 1 nM, or an affinity ranging between any of the foregoing values.

Affinity of anti-α4β7 antibodies for human α4β7 can be determined using techniques well known in the art or described herein, such as for example, but not by way of limitation, ELISA, isothermal titration calorimetry (ITC), surface plasmon resonance, or fluorescent polarization assay.

Anti-α4β7 antibodies generally comprise a heavy chain comprising a variable region ($V_H$) having three complementarity determining regions ("CDRs") referred to herein (in N→C order) as $V_H$ CDR #1, $V_H$ CDR #2, and $V_H$ CDR #3, and a light chain comprising a variable region ($V_L$) having three complementarity determining regions referred to herein (in N→C order) as $V_L$ CDR #1, $V_L$ CDR #2, and $V_L$ CDR #3. The amino acid sequences of exemplary CDRs, as well as the amino acid sequence of the $V_H$ and $V_L$ regions of the heavy and light chains of exemplary anti-α4β7 are provided herein. Specific embodiments of anti-α4β7 antibodies include these exemplary CDRs and/or $V_H$ and/or $V_L$ sequences, as well as antibodies that compete for binding human α4β7 with such antibodies.

In some embodiments, an anti-α4β7 antibody is suitable for administration to humans. In specific embodiments, the anti-α4β7 antibody is humanized.

In some embodiments, the amino acid sequences of the CDRs of an anti-α4β7 antibody are selected from the sequences of TABLE 4.

TABLE 4

CDR Sequences of Specific Embodiments

| CDR | Sequence (N → C) | Sequence Identifier |
|---|---|---|
| $V_H$ CDR #1: | NTYMH | SEQ ID NO: 12 |
| | GFNIKNTYMH | SEQ ID NOS: 32, 42, 52, 62, 72, 82 |
| $V_H$ CDR #2: | RIDPANGHTEYAP | SEQ ID NO: 13 |
| | RIDPANGHTEYAPKFQG | SEQ ID NO: 33 |
| | RIDPANKHTEYAPKFLG | SEQ ID NO: 43 |
| | RIDPARGHTEYAPKFSG | SEQ ID NO: 53 |
| | RIDPARGHTEYAPKFEG | SEQ ID NO: 63 |
| | RIDPAKGHTEYAPKFLG | SEQ ID NO: 73 |
| | RIDPAGGHTEYAPKFIG | SEQ ID NO: 83 |
| $V_H$ CDR #3: | YYVDS | SEQ ID NO: 14 |
| | VDS | SEQ ID NO: 34 |
| | VAS | SEQ ID NOS: 44, 64, 84 |
| | VDQ | SEQ ID NO: 54 |
| | VDV | SEQ ID NO: 74 |
| $V_L$ CDR #1: | HASQGISDNIG | SEQ ID NOS: 15, 35 |
| | HASQEISDNIG | SEQ ID NO: 45, 85 |
| | HASQDISDNIG | SEQ ID NO: 55, 65, 75 |
| $V_L$ CDR #2: | HGTNLED | SEQ ID NOS: 16, 36, 46, 56, 66, 76, 86 |
| $V_L$ CDR #3: | VQYAQFPWT | SEQ ID NOS: 17, 37, 47, 57, 67, 77, 87 |

Specific exemplary embodiments of anti-α4β7 antibodies with the above CDRs are described herein. In some embodiments, an anti-α4β7 antibody has the CDRs of SEQ ID NOS:12, 13, 14, 15, 16, and 17. In some embodiments, an anti-α4β7 antibody has the CDRs of SEQ ID NOS:32, 33, 34, 35, 36, and 37. In some embodiments, an anti-α4β7 antibody has the CDRs of SEQ ID NOS:42, 43, 44, 45, 46, and 47. In some embodiments, an anti-α4β7 antibody has the CDRs of SEQ ID NOS:52, 53, 54, 55, 56, and 57. In some embodiments, an anti-α4β7 antibody has the CDRs of SEQ ID NOS:62, 63, 64, 65, 66, and 67. In some embodiments, an anti-α4β7 antibody has the CDRs of SEQ ID NOS:72, 73, 74, 75, 76, and 77. In some embodiments, an anti-α4β7 antibody has the CDRs of SEQ ID NOS:82, 83, 84, 85, 86, and 87.

In some embodiments, an anti-α4β7 antibody comprises a $V_H$ chain and a $V_L$ chain selected from the sequences of TABLE 5:

TABLE 5

Variable Region Sequences of Specific Embodiments

| Type | Sequence ID |
|---|---|
| $V_H$: | SEQ ID NO: 10 |
| | SEQ ID NO: 20 |
| | SEQ ID NO: 21 |
| | SEQ ID NO: 22 |
| | SEQ ID NO: 23 |
| | SEQ ID NO: 40 |
| | SEQ ID NO: 50 |
| | SEQ ID NO: 60 |
| | SEQ ID NO: 70 |
| | SEQ ID NO: 80 |
| $V_L$: | SEQ ID NO: 11 |
| | SEQ ID NO: 25 |
| | SEQ ID NO: 26 |
| | SEQ ID NO: 27 |
| | SEQ ID NO: 28 |
| | SEQ ID NO: 41 |

TABLE 5-continued

Variable Region Sequences of Specific Embodiments

| Type | Sequence ID |
|---|---|
| | SEQ ID NO: 51 |
| | SEQ ID NO: 61 |
| | SEQ ID NO: 71 |
| | SEQ ID NO: 81 |

In some embodiments, an anti-α4β7 antibody comprises a $V_H$ chain corresponding in sequence to SEQ ID NO:10; and a $V_L$ chain corresponding in sequence to SEQ ID NO:11. In some embodiments, an anti-α4β7 antibody comprises a $V_H$ chain corresponding in sequence to any one of SEQ ID NOS:20, or 22-23; and a $V_L$ chain corresponding in sequence to any one of SEQ ID NOS:25, or 27-28. In some embodiments, an anti-α4β7 antibody comprises a $V_H$ chain corresponding in sequence to a variant of SEQ ID NO:21;

and a $V_L$ chain corresponding in sequence to a variant of SEQ ID NOS:26. In some embodiments, an anti-α4β7 antibody comprises a $V_H$ chain corresponding in sequence to SEQ ID NO:40; and a $V_L$ chain corresponding in sequence to SEQ ID NO:41. In some embodiments, an anti-α4β7 antibody comprises a $V_H$ chain corresponding in sequence to SEQ ID NO:50; and a $V_L$ chain corresponding in sequence to SEQ ID NO:51. In some embodiments, an anti-α4β7 antibody comprises a $V_H$ chain corresponding in sequence to SEQ ID NO:60; and a $V_L$ chain corresponding in sequence to SEQ ID NO:61. In some embodiments, an anti-α4β7 antibody comprises a $V_H$ chain corresponding in sequence to SEQ ID NO:70; and a $V_L$ chain corresponding in sequence to SEQ ID NO:71. In some embodiments, an anti-α4β7 antibody comprises a $V_H$ chain corresponding in sequence to SEQ ID NO:80; and a $V_L$ chain corresponding in sequence to SEQ ID NO:81.

Certain mutations of a $V_H$ or $V_L$ sequence in an anti-α4β7 antibody described herein would be understood by a person of skill to afford anti-α4β7 antibodies within the scope of the disclosure. Mutations may include amino acid substitutions, additions, or deletions from a $V_H$ or $V_L$ sequence as disclosed herein while retaining significant anti-α4β7 activity. Accordingly, in some embodiments, an anti-α4β7 antibody comprises a $V_H$ sequence having at least 85%, at least 90%, at least 93%, at least 95%, at least 96%, at least 97%, at least 98%, or at least 99% sequence identity to the $V_H$ sequence of any one of the antibodies shown in TABLE 5. An anti-α4β7 antibody can comprise a $V_H$ sequence having up to 8, up to 7, up to 6, up to 5, up to 4, up to 3, or up to 2 mutations compared with the $V_H$ sequence of any one of the antibodies shown in TABLE 5. In some embodiments, an anti-α4β7 antibody can comprise a $V_H$ sequence having 5 or fewer, 4 or fewer, 3 or fewer, or 2 or fewer mutations compared with the $V_H$ sequence of any one of the antibodies shown in TABLE 5. In some embodiments, an anti-α4β7 antibody comprises a $V_H$ sequence having a single amino acid substitution. In some embodiments, the mutation in the $V_H$ sequence is located in $V_H$ CDR #1, $V_H$ CDR #2, or $V_H$ CDR #3. In some embodiments, an anti-α4β7 antibody comprises a $V_L$ sequence having at least 85%, at least 90%, at least 93%, at least 95%, at least 96%, at least 97%, at least 98%, or at least 99% sequence identity to the $V_L$ sequence of any one of the antibodies shown in TABLE 5. An anti-α4β7 antibody can comprise a $V_L$ sequence having up to 8, up to 7, up to 6, up to 5, up to 4, up to 3, or up to 2 mutations compared with the $V_L$ sequence of any one of the antibodies shown in TABLE 5. In some embodiments, an anti-α4β7 antibody can comprise a $V_L$ sequence having 5 or fewer, 4 or fewer, 3 or fewer, or 2 or fewer mutations compared with the $V_L$ sequence of any one of the antibodies shown in TABLE 5. In some embodiments, an anti-α4β7 antibody comprises a $V_L$ sequence having a single amino acid substitution. In some embodiments, the mutation in the $V_L$ sequence is located in $V_L$ CDR #1, $V_L$ CDR #2, or $V_L$ CDR #3.

In some embodiments, an anti-α4β7 antibody comprises a heavy chain amino acid sequence, and/or a light chain amino acid sequence selected from the sequences of TABLE 6.

TABLE 6

| Full Length Chains | |
|---|---|
| Chain | Sequence ID |
| Heavy Chain | SEQ ID NO: 90 |
| | SEQ ID NO: 91 |
| | SEQ ID NO: 92 |
| | SEQ ID NO: 93 |
| | SEQ ID NO: 94 |
| | SEQ ID NO: 95 |
| | SEQ ID NO: 96 |
| | SEQ ID NO: 97 |
| | SEQ ID NO: 98 |
| | SEQ ID NO: 99 |
| Light Chain | SEQ ID NO: 100 |

In some embodiments, an anti-α4β7 antibody comprises a heavy chain corresponding in sequence to SEQ ID NO:90; and a light chain corresponding in sequence to SEQ ID NO:100. In some embodiments, an anti-α4β7 antibody comprises a heavy chain corresponding in sequence to SEQ ID NO:92; and a light chain corresponding in sequence to SEQ ID NO:100. In some embodiments, an anti-α4β7 antibody comprises a heavy chain corresponding in sequence to SEQ ID NO:94; and a light chain corresponding in sequence to SEQ ID NO:100. In some embodiments, an anti-α4β7 antibody comprises a heavy chain corresponding in sequence to SEQ ID NO:96; and a light chain corresponding in sequence to SEQ ID NO:100. In some embodiments, an anti-α4β7 antibody comprises a heavy chain corresponding in sequence to SEQ ID NO:98; and a light chain corresponding in sequence to SEQ ID NO:100.

Post-translational modifications to the sequences of an anti-α4β7 antibody may occur, such as cleavage of one or more (e.g., 1, 2, 3, or more) amino acid residues on the C-terminal end of the antibody heavy chain, creating a truncated form.

In some embodiments, an anti-α4β7 antibody comprises a heavy chain corresponding in sequence to SEQ ID NO:91; and a light chain corresponding in sequence to SEQ ID NO:100. In some embodiments, an anti-α4β7 antibody comprises a heavy chain corresponding in sequence to SEQ ID NO:93; and a light chain corresponding in sequence to SEQ ID NO:100. In some embodiments, an anti-α4β7 antibody comprises a heavy chain corresponding in sequence to SEQ ID NO:95; and a light chain corresponding in sequence to SEQ ID NO:100. In some embodiments, an anti-α4β7 antibody comprises a heavy chain corresponding in sequence to SEQ ID NO:97; and a light chain corresponding in sequence to SEQ ID NO:100. In some embodiments, an anti-α4β7 antibody comprises a heavy chain corresponding in sequence to SEQ ID NO:99; and a light chain corresponding in sequence to SEQ ID NO:100.

In some embodiments, the anti-α4β7 antibodies compete for binding human α4β7 in in vitro assays with a reference antibody. In some embodiments, the anti-α4β7 antibodies compete for binding human α4β7 on cells expressing human α4β7. The reference antibody may be any of the anti-α4β7 antibodies described herein. In some embodiments, the reference antibody is an antibody provided for in TABLES 4-6. In some embodiments, the reference antibody is an antibody provided for in TABLE 8. In specific embodiments, the reference antibody is selected from a research grade antibody generated using amino acid sequences from an anti-human α4β7 antibody or an antibody having an amino acid sequence equivalent thereto, such as vedolizumab.

In some embodiments, the anti-α4β7 antibodies antagonize, e.g., inhibit, human α4β7 heterodimer of one α4 (SEQ ID NOS:1-2) and one β7 (SEQ ID NOS:3-4). α4β7 receptor antagonism can occur by a number of mechanisms, for example, by inhibiting binding of α4β7 by at least one of its ligands, such as human MAdCAM-1 (SEQ ID NO:5) or human VCAM-1 (SEQ ID NO:6).

The anti-α4β7 antibodies described herein bind to human α4β7. Cross reactivity of the antibodies for binding to α4β7 from other species, for example, from monkey, e.g., cynomolgus monkey, may offer advantages, such as the ability to test in monkey animal models for biological activity. Such animal model testing may be used to screen anti-α4β7 antibodies to select properties related to efficacy, e.g., favorable pharmacokinetics, or those related to safety, e.g., decreased hepatic toxicity. In some embodiments, the anti-α4β7 antibodies bind to cynomolgus α4β7 as well as human α4β7.

Assays for competition include, but are not limited to, a radioactive material labeled immunoassay (RIA), an enzyme-linked immunosorbent assay (ELISA), a sandwich ELISA, fluorescence activated cell sorting (FACS) assays, and surface plasmon resonance assays.

In conducting an antibody competition assay between a reference antibody and a test antibody (irrespective of species or isotype), one may first label the reference with a detectable label, such as a fluorophore, biotin or an enzymatic (or even radioactive) label to enable subsequent identification. In this case, cells expressing human α4β7 are incubated with unlabeled test antibody, labeled reference antibody is added, and the intensity of the bound label is measured. If the test antibody competes with the labeled reference antibody by binding to an overlapping epitope, the intensity will be decreased relative to a control reaction carried out without test antibody.

In a specific embodiment of this assay, the concentration of labeled reference antibody that yields 80% of maximal binding ("conc$_{80\%}$") under the assay conditions (e.g., a specified density of cells) is first determined, and a competition assay carried out with 10×conc$_{80\%}$ of unlabeled test antibody and conc$_{80\%}$ of labeled reference antibody.

The inhibition can be expressed as an inhibition constant, or $K_i$, which is calculated according to the following formula:

$$K_i = IC_{50}/(1+[\text{reference } Ab \text{ concentration}]/K_d),$$

where IC$_{50}$ is the concentration of test antibody that yields a 50% reduction in binding of the reference antibody and $K_d$ is the dissociation constant of the reference antibody, a measure of its affinity for human α4β7. Antibodies that compete with anti-α4β7 antibodies disclosed herein can have a $K_i$ from 10 pM to 10 nM under assay conditions described herein.

In various embodiments, a test antibody is considered to compete with a reference antibody if it decreases binding of the reference antibody by at least about 20% or more, for example, by at least about 20%, 30%, 40%, 50%, 60%, 70%, 80%, 90%, 95% or even more, or by a percentage ranging between any of the foregoing values, at a reference antibody concentration that is 80% of maximal binding under the specific assay conditions used, and a test antibody concentration that is 10-fold higher than the reference antibody concentration.

Another aspect of the present disclosure includes anti-α4β7 antibody binding fragments that are capable of specifically binding human α4β7. In some embodiments, these anti-α4β7 binding fragments comprise at least one and up to all CDRs of the anti-α4β7 antibodies disclosed herein. Examples of antibody binding fragments include by way of example and not limitation, Fab, Fab', F(ab')$_2$, Fv fragments, single chain Fv fragments and single domain fragments.

An anti-α4β7 antibody or binding fragment thereof may have one or more amino acids inserted into one or more of its CDRs, for example as described in Jung and Plückthun, 1997, Protein Engineering 10:9, 959-966; Yazaki et al., 2004, Protein Eng. Des Sel. 17(5):481-9. Epub 2004 Aug. 17; and U.S. Pat. Appl. No. 2007/0280931.

6.4. Polynucleotides Encoding the Anti-α4β7 Antibodies, Expression Systems and Methods of Making the Antibodies The present disclosure encompasses polynucleotide molecules encoding immunoglobulin light and heavy chain genes for anti-α4β7 antibodies, vectors comprising such polynucleotides, and host cells capable of producing the anti-α4β7 antibodies of the disclosure.

An anti-α4β7 antibody of the disclosure can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered.

To generate polynucleotides encoding such anti-α4β7 antibodies, DNA fragments encoding the light and heavy chain variable regions are first obtained. These DNAs can be obtained by amplification and modification of germline DNA or cDNA encoding light and heavy chain variable sequences, for example using the polymerase chain reaction (PCR).

Once DNA fragments encoding anti-α4β7 antibody-related $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions (CH1, CH2, CH3 and, optionally, CH4). The sequences of human heavy chain constant region genes are known in the art (See, e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG$_1$, IgG$_2$, IgG$_3$, IgG$_4$, IgA, IgE, IgM or IgD constant region, but in certain embodiments is an IgG$_1$ or IgG$_4$. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (See, e.g., Kabat, et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but in certain embodiments is a kappa constant region.

To express the anti-α4β7 antibodies of the disclosure, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the anti-α4β7 antibody-related light or heavy chain sequences, the expression vector can already carry antibody constant region sequences. For example, one approach to converting the anti-α4β7 monoclonal antibody-related $V_H$ and $V_L$ sequences to full-length antibody genes is to insert them into expression vectors already encoding heavy chain constant and light chain constant regions, respectively, such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes.

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced. For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE-dextran transfection and the like.

It is possible to express the antibodies of the disclosure in either prokaryotic or eukaryotic host cells. In certain embodiments, expression of antibodies is performed in eukaryotic cells, e.g., mammalian host cells, of optimal secretion of a properly folded and immunologically active antibody. Exemplary mammalian host cells for expressing the recombinant antibodies of the disclosure include Chinese Hamster Ovary (CHO cells) (including DHFR⁻ CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as Fab fragments or scFv molecules. It is understood that variations on the above procedure are within the scope of the present disclosure. For example, it can be desirable to transfect a host cell with DNA encoding either the light chain or the heavy chain (but not both) of an anti-α4β7 antibody of this disclosure.

Recombinant DNA technology can also be used to remove some or all of the DNA encoding either or both of the light and heavy chains that is not necessary for binding to human α4β7. The molecules expressed from such truncated DNA molecules are also encompassed by the antibodies of the disclosure.

For recombinant expression of an anti-α4β7 antibody of the disclosure, the host cell can be co-transfected with two expression vectors of the disclosure, the first vector encoding a heavy chain derived polypeptide and the second vector encoding a light chain derived polypeptide. The two vectors can contain identical selectable markers, or they can each contain a separate selectable marker. Alternatively, a single vector can be used which encodes both heavy and light chain polypeptides.

Once a polynucleotide encoding one or more portions of an anti-α4β7 antibody has been obtained, further alterations or mutations can be introduced into the coding sequence, for example to generate polynucleotides encoding antibodies with different CDR sequences, antibodies with reduced affinity to the Fc receptor, or antibodies of different subclasses.

The anti-α4β7 antibodies of the disclosure can also be produced by chemical synthesis or by using a cell-free platform.

6.5. Purification of Anti-α4β7 Antibodies

Once a polypeptide of the disclosure has been produced by recombinant expression, it can be purified by any method known in the art for purification of a protein.

The polypeptides may be purified as a monomer or as a dimer, e.g., as a anti-α4β7 antibody comprising two polypeptides.

Once isolated, an anti-α4β7 antibody can be further purified.

6.6. Methods of Use

6.6.1. Therapeutic Benefit

Data provided herein demonstrate that the disclosed anti-human α4β7 antibodies demonstrate favorable binding affinity, specificity, and potency towards α4β7, as well as favorable binding profiles on primary immune cells, FcγR binding, and lack of ADCC and ADCP activity on human α4β7+ cells. These anti-human α4β7 antibodies were shown to bind to α4β7 in the virions of different laboratory-grown HIV strains as well as from patients' HIV samples, and subsequently form immune complexes. These immune complexes can bind to different FcγRs and taken up by a human monocytic cell line THP-1 by phagocytosis. These antibodies also block the interaction of α4β7 with its ligands such as MadCAM-1 and HIV gp120 protein. Accordingly, the anti-α4β7 antibodies, binding fragments, and/or pharmaceutical compositions comprising them may be used therapeutically to induce viral suppression of HIV infection or to reduce viral load in an HIV infected subject by Fc-dependent and Fab-dependent mechanisms. In some embodiments, viral suppression of HIV infection involves reducing function of the HIV virus and/or reducing replication of the HIV virus.

The disclosed anti-human α4β7 antibodies may be used in a method of treating HIV infection in a subject in need thereof. In some embodiments, the method involves reducing viral load in the subject. In some embodiments, the viral load in the subject is reduced to undetectable levels. In some embodiments, the subject is a human subject infected with HIV.

In some embodiments, the method involves administering to a human subject having HIV infection an anti-α4β7 antibody that antagonizes α4β7 to provide therapeutic benefit. In some embodiments, the method involves administering to a human subject having HIV infection an anti-α4β7 antibody which binds to HIV virions. In some embodiments, the method involves administering to a human subject having HIV infection an anti-α4β7 antibody which binds to α4β7 in HIV virions to form immune complexes. In some embodiments, the method involves administering to a human subject having HIV infection an anti-α4β7 antibody forming immune complexes with HIV virions. In some embodiments, these immune complexes are taken up by APCs by phagocytosis. In some embodiments, the method involves administering to a human subject having HIV infection an anti-α4β7 antibody which blocks the interaction of α4β7 with its ligands such as MadCAM-1 and with HIV gp120. In some embodiments, the method involves administering to a human subject having HIV infection an anti-α4β7 antibody that blocks the interaction of α4β7 with HIV gp120, inhibiting the cell-to-cell HIV transmission. In some embodiments, the method involves administering to a human subject having HIV infection an anti-α4β7 antibody that blocks CD4 T cell stimulation mediated by MadCAM-1 or HIV gp120. In some embodiments, the method involves administering to a human subject having HIV infection an anti-α4β7 antibody which suppresses HIV replication in the CD4 T cells costimulated by MadCAM-1 or HIV gp120. In some embodiments, the method involves administering to a human subject having HIV infection an anti-α4β7 antibody which induces viral suppression of HIV replication. In some embodiments, the method involves administering to a human subject having HIV infection an anti-α4β7 antibody which induces HIV suppression that is immune-mediated.

6.7. Table of Sequence Descriptions

A correlation of sequences disclosed in the incorporated Sequence Listing and their brief descriptions is shown in TABLE 7.

TABLE 7

Brief Description of the Sequence Listing

| Sequence | Description | Sequence | Description |
| --- | --- | --- | --- |
| SEQ ID NO: 1 | human α4 | SEQ ID NO: 50 | Ab-h1.9b VH |
| SEQ ID NO: 2 | human α4 | SEQ ID NO: 51 | Ab-h1.9b VL |
| SEQ ID NO: 3 | human β7 | SEQ ID NO: 52 | Ab-h1.9b VH-CDR1 |
| SEQ ID NO: 4 | human β7 | SEQ ID NO: 53 | Ab-h1.9b VH-CDR2 |
| SEQ ID NO: 5 | MAdCAM-1 | SEQ ID NO: 54 | Ab-h1.9b VH-CDR3 |
| SEQ ID NO: 6 | VCAM-1 | SEQ ID NO: 55 | Ab-h1.9b VL-CDR1 |
| SEQ ID NO: 7 | gp120-V2 WT | SEQ ID NO: 56 | Ab-h1.9b VL-CDR2 |
| SEQ ID NO: 8 | gp120-V2 control | SEQ ID NO: 57 | Ab-h1.9b VL-CDR3 |
| SEQ ID NO: 10 | Ab-m1 VH | SEQ ID NO: 60 | Ab-h1.9c VH |
| SEQ ID NO: 11 | Ab-m1 VL | SEQ ID NO: 61 | Ab-h1.9c VL |
| SEQ ID NO: 12 | Ab-m1 VH-CDR1 | SEQ ID NO: 62 | Ab-h1.9c VH-CDR1 |
| SEQ ID NO: 13 | Ab-m1 VH-CDR2 | SEQ ID NO: 63 | Ab-h1.9c VH-CDR2 |
| SEQ ID NO: 14 | Ab-m1 VH-CDR3 | SEQ ID NO: 64 | Ab-h1.9c VH-CDR3 |
| SEQ ID NO: 15 | Ab-m1 VL-CDR1 | SEQ ID NO: 65 | Ab-h1.9c VL-CDR1 |
| SEQ ID NO: 16 | Ab-m1 VL-CDR2 | SEQ ID NO: 66 | Ab-h1.9c VL-CDR2 |
| SEQ ID NO: 17 | Ab-m1 VL-CDR3 | SEQ ID NO: 67 | Ab-h1.9c VL-CDR3 |
| SEQ ID NO: 20 | Ab-h1 VH.1 | SEQ ID NO: 70 | Ab-h1.9d VH |
| SEQ ID NO: 21 | Ab-h1 VH.1 variable | SEQ ID NO: 71 | Ab-h1.9d VL |
| SEQ ID NO: 22 | Ab-h1 VH.1.a | SEQ ID NO: 72 | Ab-h1.9d VH-CDR1 |
| SEQ ID NO: 23 | Ab-h1 VH.1b | SEQ ID NO: 73 | Ab-h1.9d VH-CDR2 |
| SEQ ID NO: 25 | Ab-h1 VL.1 | SEQ ID NO: 74 | Ab-h1.9d VH-CDR3 |
| SEQ ID NO: 26 | Ab-h1 VL.1 variable | SEQ ID NO: 75 | Ab-h1.9d VL-CDR1 |
| SEQ ID NO: 27 | Ab-h1 VL.1.a | SEQ ID NO: 76 | Ab-h1.9d VL-CDR2 |
| SEQ ID NO: 28 | Ab-h1 VL.1b | SEQ ID NO: 77 | Ab-h1.9d VL-CDR3 |
| SEQ ID NO: 32 | Ab-h1.9 VH-CDR1 | SEQ ID NO: 80 | Ab-h1.9e VH |
| SEQ ID NO: 33 | Ab-h1.9 VH-CDR2 | SEQ ID NO: 81 | Ab-h1.9e VL |
| SEQ ID NO: 34 | Ab-h1.9 VH-CDR3 | SEQ ID NO: 82 | Ab-h1.9e VH-CDR1 |
| SEQ ID NO: 35 | Ab-h1.9 VL-CDR1 | SEQ ID NO: 83 | Ab-h1.9e VH-CDR2 |
| SEQ ID NO: 36 | Ab-h1.9 VL-CDR2 | SEQ ID NO: 84 | Ab-h1.9e VH-CDR3 |
| SEQ ID NO: 37 | Ab-h1.9 VL-CDR3 | SEQ ID NO: 85 | Ab-h1.9e VL-CDR1 |
| SEQ ID NO: 40 | Ab-h1.9a VH | SEQ ID NO: 86 | Ab-h1.9e VL-CDR2 |
| SEQ ID NO: 41 | Ab-h1.9a VL | SEQ ID NO: 87 | Ab-h1.9e VL-CDR3 |
| SEQ ID NO: 42 | Ab-h1.9a VH-CDR1 | SEQ ID NOS:90, 91* | Ab-h1.9d-hIgG1 (*terminal lysine trunc.) |
| SEQ ID NO: 43 | Ab-h1.9a VH-CDR2 | SEQ ID NOS:92, 93* | Ab-h1.9d-WT HC (*K trunc.) |
| SEQ ID NO: 44 | Ab-h1.9a VH-CDR3 | SEQ ID NOS:94, 95* | Ab-h1.9d-LALA HC (*K trunc.) |
| SEQ ID NO: 45 | Ab-h1.9a VL-CDR1 | SEQ ID NOS:96, 97* | Ab-h1.9d-QL HC (*K trunc.) |
| SEQ ID NO: 46 | Ab-h1.9a VL-CDR2 | SEQ ID NOS:98, 99* | Ab-h1.9d-LALA/QL HC (*K trunc.) |
| SEQ ID NO: 47 | Ab-h1.9a VL-CDR3 | SEQ ID NO: 100 | Ab-h1.9d LC (*K trunc.) |

7. EXAMPLES

The following Examples, which highlight certain features and properties of the exemplary embodiments of the antibodies and binding fragments described herein are provided for purposes of illustration, and not limitation.

Antibodies

Test antibodies used through the examples including Ab-h1.9d-WT, positive controls and isotype controls are listed in TABLE 8.

TABLE 8

Partial List of Prepared Antibodies

| Name | Use | Description |
| --- | --- | --- |
| Ab-h1.9d-WT | Exemplary Ab | Humanized anti-human α4β7, liability engineered [hu IgG1/k; WT] |
| Ab-h1.9(x) series | Exemplary Ab | Humanized anti-human α4β7, liability engineered [hu IgG1/k] |
| Ab-h1.(x) series | Exemplary Ab | Humanized anti-human α4β7 [hu IgG1/k; WT] |
| Ab-h1 | Exemplary Ab | Humanized anti-human α4β7 [hu IgG1/k; WT] |
| Ab-c1 | Exemplary Ab | Chimeric anti-human α4β7 [hu IgG1/k; WT] |
| Ab-m1 | Exemplary Ab | Mouse anti-human α4β7 [mu IgG1/k; WT] |
| Ab-Vedo | Comparator | Humanized anti-human α4β7 mAb [hu IgG1/k; LALA]; In-house version with vedolizumab (Entyvio ®) variable domain |
| Ab-Abri | Comparator | Human anti-human α4β7 mAb; [IgG2/k; WT]; In-house version with abrilumab (AMG181) variable domain |
| Ab-Etro | Comparator | Humanized anti-human β7 mAb [hu IgG1/k; WT]; In-house version with etrolizumab (RG7413) variable domain |
| Ab-Nata | Comparator | Humanized anti-human α4 mAb [hu IgG4/k; WT] Natalizumab (Tysabri ®) |
| Ab-Ritu | Comparator | Chimeric anti-human CD20 mAb [hu IgG1/k; WT] Rituximab (Rituxan ®) |
| Ab-Tras | Comparator | Anti-human HER2 mAb Trastuzumab (HERCEPTIN ®) |
| Ab-Ctet | Isotype control | Anti-tetanus toxoid (*Clostridium tetani*) mAb [hu IgG1/k; WT] |
| Ab-CMV | Isotype control | Anti-CMV gH MSL 109 mAb [hu IgG1/k; WT] |
| Ab-Alem | ADCC control | Anti-human CD52 mAb (Campath-1H) [hu IgG1/k; WT] |

Statistics

Half maximal inhibitory concentration ($IC_{50}$) and half maximal effective concentration (EGO) values were determined by non-linear regression analysis of the concentration response curves using GraphPad Prism. Significance of comparisons were determined by Mann-Whitney two-tailed test. All values were the average or standard deviation of results of at least three independent experiments, excepted noted.

7.1. Example 1: Generation of Anti-Human α4β7 Antibodies

7.1.1. Hybridoma Screening

Hybridoma-based techniques were utilized to generate an initial panel of mouse anti-human α4β7 antibodies. Mice were immunized with HEK293, CHO-K1 or BaF3 recombinant cells expressing human α4β7 in addition to adjuvant. The selection of candidate hybridoma derived antibodies was based on criteria of TABLE 9:

TABLE 9

Candidate Selection Criteria

| | |
| --- | --- |
| Binding | Bind to HuT78 cell, a human T lymphoma cell line expressing endognous cell surface α4β7 |
| | Bind to human and cyno CD4 + and CD8 + T cells |
| Potency | Block the adhesion of HuT78 cells to plate-bound human MAdCAM-1-Fc protein |
| | Block the binding of MAdCAM-1-Fc to human and cyno CD4 + central memory T cells |
| Binding specificicity | Bind to recombinant cells expressing human α4β7 |
| | Do not bind to human α4β1 |
| | Bind minimally or not at all to recombinant cells expressing human and cyno α4β7 |
| Species cross-reactivity | Bind to recombinant cells expressing cyno α4β7 |
| | Bind to recombinant cells expressing rat and mouse α4β7 |

A panel of functional hybridoma mAbs was identified from this screen, with all candidates displaying a favorable profile. However, none had rodent cross-reactivity, which may be explained by 1) human α4/β7 having 96%/97% amino acid sequence homology to cyno monkey α4/β7 but only 84%/85% sequence homology to rat and mouse α4/β7; and 2) all the selected functional hybridoma mAbs are highly selective for α4β7, and may bind to conformational epitope(s) on the α4β7 heterodimer.

7.1.2. Antibody Characterization

Small scale of antibody production by 200-300 ml roller bottle culture and Protein A affinity purification was performed on subcloned stable hybridoma cell lines. Purity of mAbs was verified by SDS-PAGE and mass spectrometry. Purified antibodies were characterized through binding and functional assays to determine isoform and species cross-reactivity.

Binding Screening

Purified antibodies were characterized for isoform and species cross-reactivity by FACS with BaF3-hα4β7, BaF3-hαEβ7, BaF3-cαEβ7, BaF3, CHOK1-cα4β7, CHOK1-mα4β7 and CHOK1-hα4β1 cell lines at a concentration of 1 µg/ml. The FACS profiles, including that of exemplary mAb Ab-m1, is summarized in TABLE 10.

TABLE 10

Isoform and Species Cross-Reactivity

| Antibody | Isotype | BaF3 | BaF3-hα4β7 | BaF3-hαEβ7 | BaF3-cαEβ7 | CHOK1-cα4β7 | CHOK1-mα4β7 | CHOK1-hα4β1 |
|---|---|---|---|---|---|---|---|---|
| | | | FACS MFI | | | | | |
| Ab-m1 | IgG1/k | 3.97 | 453.71 | 17.35 | 54.31 | 45.14 | 3.6 | 3.72 |
| Ab-Vedo | hIgG1/k | 3.53 | 706.72 | 11.60 | 57.21 | 100.88 | 2.91 | 4.23 |
| Ab-Abri | hIgG2/k | 3.54 | 623.52 | 9.81 | 68.35 | 89.85 | 2.87 | 4.25 |
| Ab-Etro | hIgG1/k | 5.78 | 439.75 | 73.21 | 247.12 | 97.21 | 92.16 | 4.53 |

Functional Validation

Purified antibody was characterized by adhesion assay to MadCAM-1 in HuT78 cells. Ab-m1 showed potential blocking potency in the MadCAM-1 assay and was therefore functionally validated. Data from three independent experiments for Ab-m1 is summarized in TABLE 11. Representative data is shown in FIG. 1.

TABLE 11

Functional Assays

| | HutT78 cell adhesion assay | | CHOK1-cα4β7 adhesion assay | |
|---|---|---|---|---|
| Antibody | IC50/MadCAM-1 (pM) | Max inhibition (%) | IC50/MadCAM-1 (pM) | Max inhibition (%) |
| Ab-m1 | 55.5 ± 6.3 | 88.9 ± 3.0 | 201.1 ± 51.2 | 84.6 ± 15.6 |
| Ab-Vedo | 94.9 ± 4.5 | 86.5 ± 13.5 | 562.3 ± 249.5 | 76.0 ± 12.6 |
| Ab-Abri | 12.87 | 103.28 | 99.40 | 95.94 |
| Ab-Etro | 17.83 | 103.5 | 241.5 ± 38.6 | 91.5 ± 7.0 |

Functional Characterization

Further functional characterization of Ab-m1 was performed using an adhesion assay to MadCAM-1 in CHOK1-cα4β7, to check for cyno cross-reactivity. The adhesion assay data in CHOK1-cα4β7 is summarized in TABLE 11 above. Representative data is shown in FIG. 2.

To determine the affinity of Ab-m1 binding to human α4β7, FACS-based titrations were performed in BaF3-hα4β7. EC50 was determined, as summarized in TABLE 12.

TABLE 12

Affinity to Human α4β7

| Antibody | Isotype | BaF3-hα4β7 FACS titration | |
|---|---|---|---|
| | | EC50 (pM) | Max MFI |
| Ab-m1 | IgG1/k | 474 | 255.6 |
| Ab-Vedo | hIgG1/k | 713.2 ± 100.9 | 848.0 ± 289.4 |
| Ab-Abri | hIgG2/k | 679 | 775.3 |
| Ab-Etro | hIgG1/k | 704.8 ± 66.8 | 950.7 ± 202.0 |

Epitope binning was performed by competitive FACS using comparator antibodies conjugated with Alexa488 fluorophore in the presence of 50× excess of non-labeled Abs indicated in the TABLE 13. Ab-m1 was characterized as belonging to a vedolizumab (Ab-Vedo) like group based on the percentage of binding inhibition of Alexa488-labeled Abs by the non-labeled Abs (TABLE 13).

TABLE 13

Epitope Binning

| Antibody | Ab-m1 | Ab-Vedo | Ab-Abri | Ab-Etro |
|---|---|---|---|---|
| Ab-Vedo-Alexa488 | 76 | 88 | 89 | 18 |
| Ab-Abri-Alexa488 | 73 | 88 | 89 | 80 |
| Ab-Etro-Alexa488 | −1 | 6 | 60 | 93 |
| IC50 (pM) HuT78 | 44.7 ± 19.3 | 89 ± 10.7 | 12.9 | 17.8 |

Candidate Profiling

Figure 3:
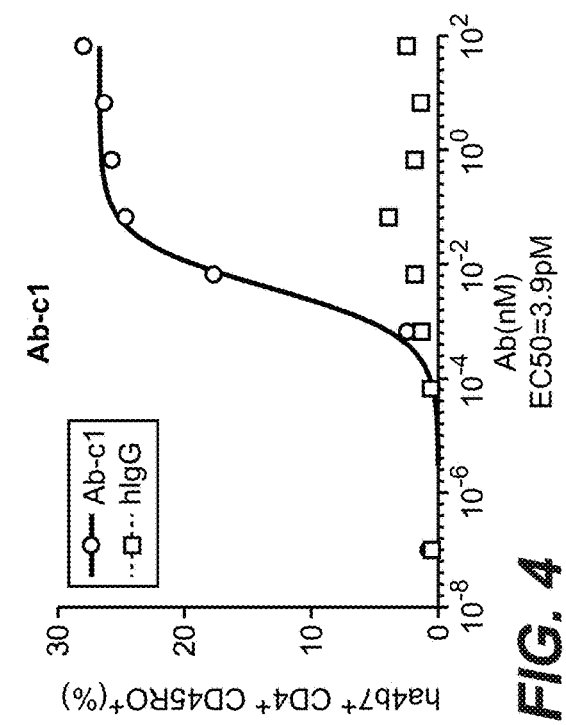
FIG. 3 shows Ab-m1 blocking of human MAdCAM-1 binding to primary human CD4+ memory T cells.

The affinity of mAbs binding to human α4β7 was confirmed in primary human CD4+ memory T cells. Ab-m1 was also capable of blocking human MadCAM-1 binding to primary human CD4+ memory T cells with high potency (IC50=63.7 pM, max inhibition 100%; FIG. 3).

7.1.3. VH/VL Sequencing, Chimeric Antibody Generation and Characterization

Hybridoma clones were recovered and expanded in complete hybridoma culture medium (DMEM with 10% FBS). Cells were harvested by centrifuging at 1000 rpm for 5 minutes at room temperature and washed twice with PBS, pH 7.4. RNA was extracted from the cell pellets (approximately 1×10$^7$ cells) with Trizol.

Antibody VH and VL fragments were separately amplified from their hybridoma total RNA by RT-PCR using mouse Ig primer set (Novagen, 69831-3). Positive PCR products of appropriate size were inserted to T-vector for sequencing and identification of VH and VL regions (TABLE 14). Full length antibody sequences were built using combinations of VH/VL sequences together with theoretical constant region sequences.

After primer designing, VL/VHs were individually amplified and cloned into expression vectors to make chimeric antibody constructs via homologous recombination. The amino acid sequences of CDRs in VH and VL are shown in TABLE 14.

TABLE 14

Exemplary Murine Variable Chains

| Ab-m1 | Heavy Chain | | | |
|---|---|---|---|---|
| | CDR1 | CDR2 | CDR3 | VH |
| | NTYMH | RIDPANGHTEYAPVDS | | SEQ ID NO: 10 |
| | SEQ ID NO: 12 | SEQ ID NO: 13 | SEQ ID NO: 14 | |

| | Light Chain | | | |
|---|---|---|---|---|
| | CDR1 | CDR2 | CDR3 | VL |
| | HASQGISDNIG | HGTNLED | VQYAQFPWT | SEQ ID NO: 11 |
| | SEQ ID NO: 15 | SEQ ID NO: 16 | SEQ ID NO: 17 | |

Chimeric antibodies were produced by transient transfection in HEK293 cells. After expression, proteins were purified. A high percentage monomer for the chimeric antibodies was confirmed by SEC-HPLC.

Figure 4:
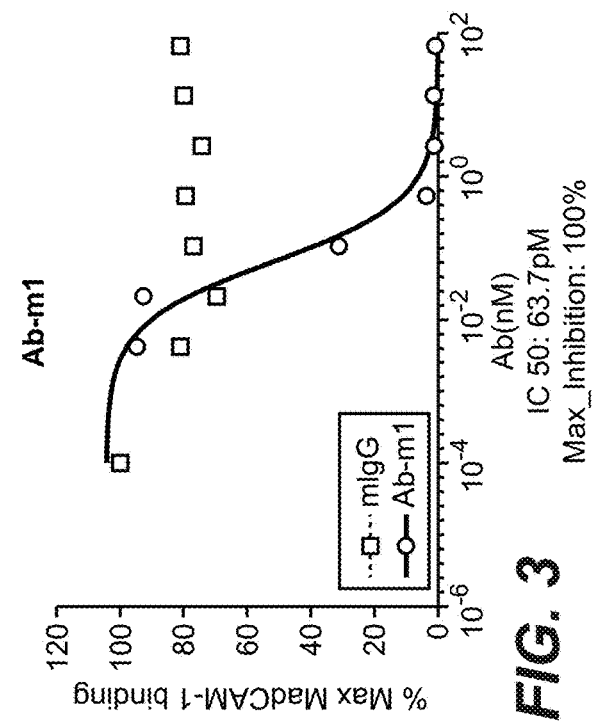
FIG. 4 shows binding of murine-human chimera Ab-c1 to human primary CD4+ memory T cells (hα4β7+CD4+CD45RO+).

Ab-c1 is a chimeric antibody having Ab-m1's variable regions and human IgG1/k constant regions. The affinity of Ab-c1 binding to human primary CD4+CD45RO+ T cells was determined by FACS with the binding EC50 value of 3.9 pM from one representative human whole blood (shown in FIG. 4 and TABLE 15). The ability of Ab-c1 to block α4β7 integrin binding to MadCAM-1 was also evaluated in HuT78 cells and CHOK1-cα4β7 cells (TABLE 15).

| Antibody | Primary CD4+ memory T cell mAb binding EC50 (pM) |
|---|---|
| Ab-m1 | 9.8 |
| Ab-c1 | 3.9 |
| Ab-Vedo | 43.2 ± 4.5 |
| Ab-Etro | 5.4 ± 0.2 |
| Ab-Abri | 4.9 ± 1.6 |

Purified chimeric antibody Ab-c1 was further characterized by FACS with BaF3-hα4β7, BaF3-hαEβ7, BaF3-cαEβ7, BaF3, CHOK1-cα4β7 and CHOK1-hα4β1 cell lines at one concentration (1 μg/ml) to confirm its binding specificity and cynomolgus cross-reactivity. The FACS profile of tested chimera is summarized in TABLE 16.

TABLE 16

FACS Profiles

| Antibody code | Isotype | FACS MFI | | | | | |
|---|---|---|---|---|---|---|---|
| | | BaF3 | BaF3-hα4β7 | BaF3-hαEβ7 | BaF3-cαEβ7 | CHOK1-cα4β7 | CHOK1-hα4β1 |
| Ab-m1 | mIgG1/k | 1.37 | 153.69 | 7.35 | 38.09 | 34.36 | 2.96 |
| Ab-c1 | hIgG1/k | 2.85 | 357.77 | 20.65 | 67.81 | 49.40 | 2.95 |
| Ab-Vedo | hIgG1/k | 2.78 | 153.43 | 19.5 | 60.87 | 46.47 | 2.87 |

HuT78 was used to investigate whether chimeric Ab-c1 was capable of blocking MadCAM-1 mediated adhesion to hα4β7 integrin. As shown in TABLE 17, Ab-c1 demonstrates the capacity to inhibit HuT78 cell adhesion to MadCAM-1.

CHOK1-cα4β7 was used to investigate whether chimeric antibodies could inhibit MadCAM-1 mediated adhesion to cα4β7. As shown in TABLE 17, the Ab-c1 demonstrates the capacity to inhibit CHOK1-cα4β7 cell adhesion to MadCAM-1.

TABLE 17

Adhesion Assays

| Antibody code | MadCAM-1/HuT78 (hα4β7) | | MadCAM-1/CHOK1 (cα4β7) | |
| --- | --- | --- | --- | --- |
| | IC50 (pM) | Max Inhibition (%) | IC50 (pM) | Max Inhibition (%) |
| Ab-m1 | 22.8 | 99.44% | 65.8 | 92.78% |
| Ab-c1 | 13.7 | 98.06% | 86.4 | 85.54% |
| Ab-Vedo | 57.4 | 94.67% | 540.8 ± 336.5 | 94.41% |

7.1.4. Humanization

Antibody Ab-m1 was selected based on binding and potency on both HuT78 cells and human primary CD4+ T memory cells, cyno cross-reactivity, CDR sequence diversity, binding selectivity, sequence liability (i.e. glycosylation), and epitope group. See TABLE 18 for specified characteristics.

TABLE 18

Ab-m1 Characterization

| Antibody | MadCAM-1/HuT78 Potency (pM) | MadCAM-1/cα4β7 Potency (pM) | Cyno x-reactivity | Human CD4+ CD45RO+ | |
| --- | --- | --- | --- | --- | --- |
| | | | | binding EC50 (pM) | MadCAM-1 inh. IC50 (pM) |
| Ab-m1 | 55.5 ± 6.3 | 201.1 ± 51.2 | 4x | 9.8 | 63.7 |

Humanized antibodies were designed from assembling VH and VL fragments in accordance with TABLE 19, and incorporating human IgG1 and kappa constant regions.

TABLE 19

VH and VL Chains of Humanized Ab-h1

| Rodent Parental | Humanized Ab | VH | VL |
| --- | --- | --- | --- |
| Ab-m1 | Ab-h1.1 | Ab-h1VH.1 (SEQ ID NO: 20) | Ab-h1VL.1 (SEQ ID NO: 25) |
| | Ab-h1.2 | Ab-h1VH.1 (SEQ ID NO: 20) | Ab-h1VL.1a (SEQ ID NO: 27) |
| | Ab-h1.3 | Ab-h1VH.1 (SEQ ID NO: 20) | Ab-h1VL.1b (SEQ ID NO: 28) |
| | Ab-h1.4 | Ab-h1VH.1a (SEQ ID NO: 22) | Ab-h1VL.1 (SEQ ID NO: 25) |
| | Ab-h1.5 | Ab-h1VH.1a (SEQ ID NO: 22) | Ab-h1VL.1a (SEQ ID NO: 27) |
| | Ab-h1.6 | Ab-h1VH.1a (SEQ ID NO: 22) | Ab-h1VL.1b (SEQ ID NO: 28) |
| | Ab-h1.7 | Ab-h1VH.1b (SEQ ID NO: 23) | Ab-h1VL.1 (SEQ ID NO: 25) |
| | Ab-h1.8 | Ab-h1VH.1b (SEQ ID NO: 23) | Ab-h1VL.1a (SEQ ID NO: 27) |
| | Ab-h1.9 | Ab-h1VH.1b (SEQ ID NO: 23) | Ab-h1VL.1b (SEQ ID NO: 28) |

These humanized anti-α4β7 mAbs were produced, having good expression, showing >95% monomers by SEC. Identity was confirmed by MS, and stability of the humanized anti-α4β7 was measured by DSC. Four of the humanized Ab-h1 were evaluated for their ability to block MAdCAM-1 mediated HuT78 cell adhesion and they all displayed strong potency with IC50 values of single digit or low double-digit pM range (TABLE 20).

TABLE 20

Humanized α4β7 mAb properties

| Humanized Ab | HuT78 cell adhesion potency IC50 (pM) | Cyno X-reactivity CHOK1/cα4β7 adhesion to MAdCAM-1 IC50 (pM) |
|---|---|---|
| Ab-h1.5 | 9.1 | |
| Ab-h1.6 | 8.1 | |
| Ab-h1.8 | 13.8 | |
| Ab-h1.9 | 11.4 | 36.5 |
| Ab-Vedo | 31; 60 | 120 |
| Ab-Abri | | 50.9 |
| Ab-Etro | | 49.9 |

7.1.5. Liability Engineering of Ab-h1.9

Antibody Ab-h1.9 was selected for generating variant VH and VL chains having reduced chemical liability with respect to deamidation, isomerization, oxidation, glycosylation, hydrolysis and cleavage.

The sequence of Ab-h1.9 $V_H$ is:

(SEQ ID NO: 23)
EVQLVQSGAEVKKPGSSVKVSCKASGFNIKNTYMHWVRQAPGQGLEWIG

RIDPANGHTEYAPKFQGRVTITADESTNTAYMELSSLRSEDTAVYYCYY

VDS**WGQGTTVTVSS and the sequence of Ab-h1.9 $V_L$ is:

(SEQ ID NO: 28)
DIQMTQSPSSLSASVGDRVTITCHASQGISDNIGWLQQKPGKSFKLLI

YHGTNLEDGVPSRFSGSGSGTDYTLTISSLQPEDFATYYCVQYAQFPW

TFGGGTKVEIKR wherein selected liability mutation sites are underlined and CDRs bolded. Liabilities are present in VH-CDR2, VH-CDR3, and VL-CDR1.

Two rounds of liability free anti-α4β7 clone selection using biotinylated human α4β7 extracellular domain protein were performed. Colonies from each library were sequenced, and those having additional liabilities in any CDR were removed. Clones from each library were screened for binding to surface α4β7 antigen on yeast by FACS, in comparison to parental Ab-h1.9.

Figure 5:
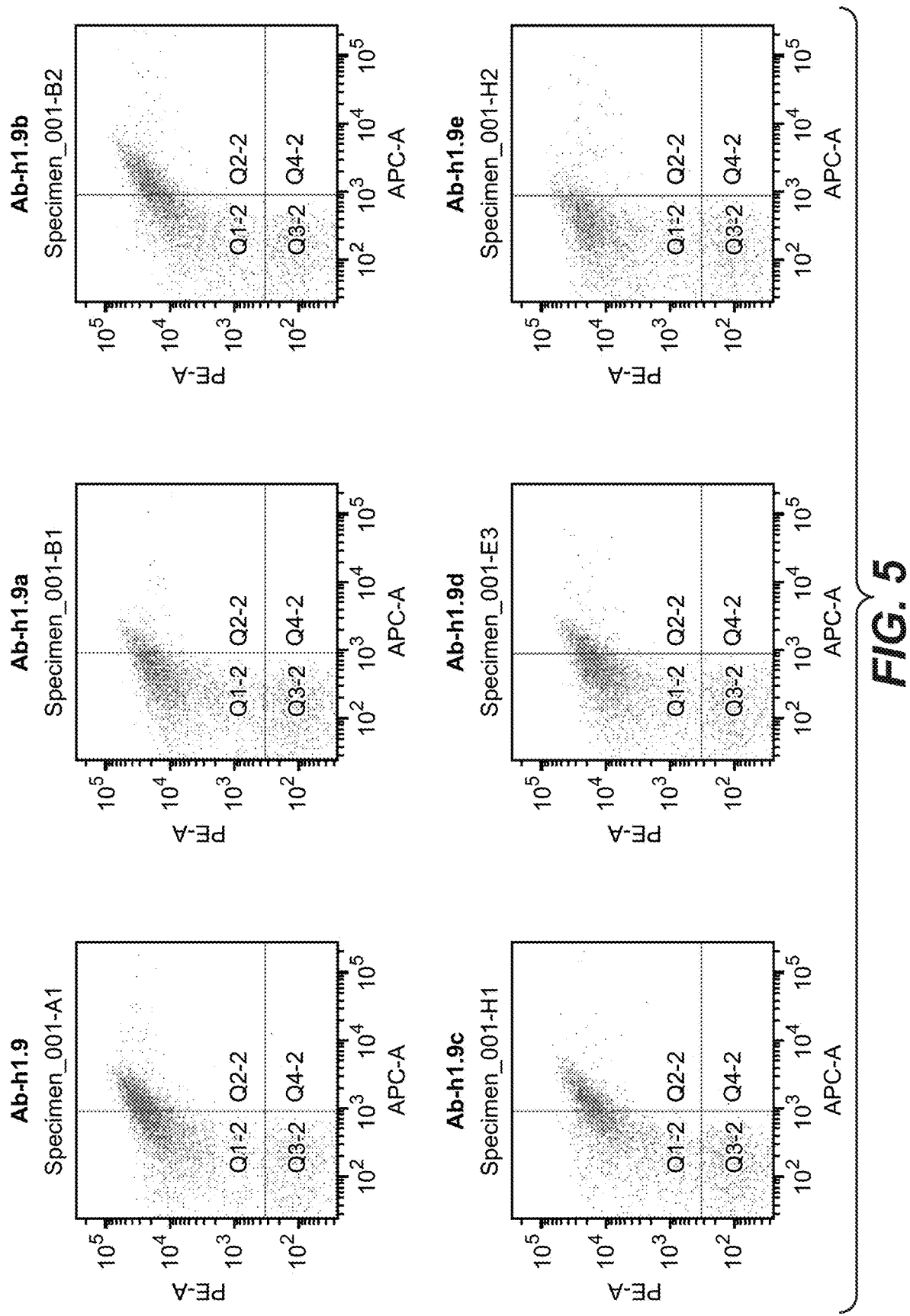
FIG. 5 shows the binding of liability engineered humanized anti-α4β7 Ab-h1.9 scFv clones against human α4β7 antigen displayed on yeast by flow cytometry. Clones Ab-h1.9 (a-e) had similar binding as parental Ab-h1.9.
Figure 6B:
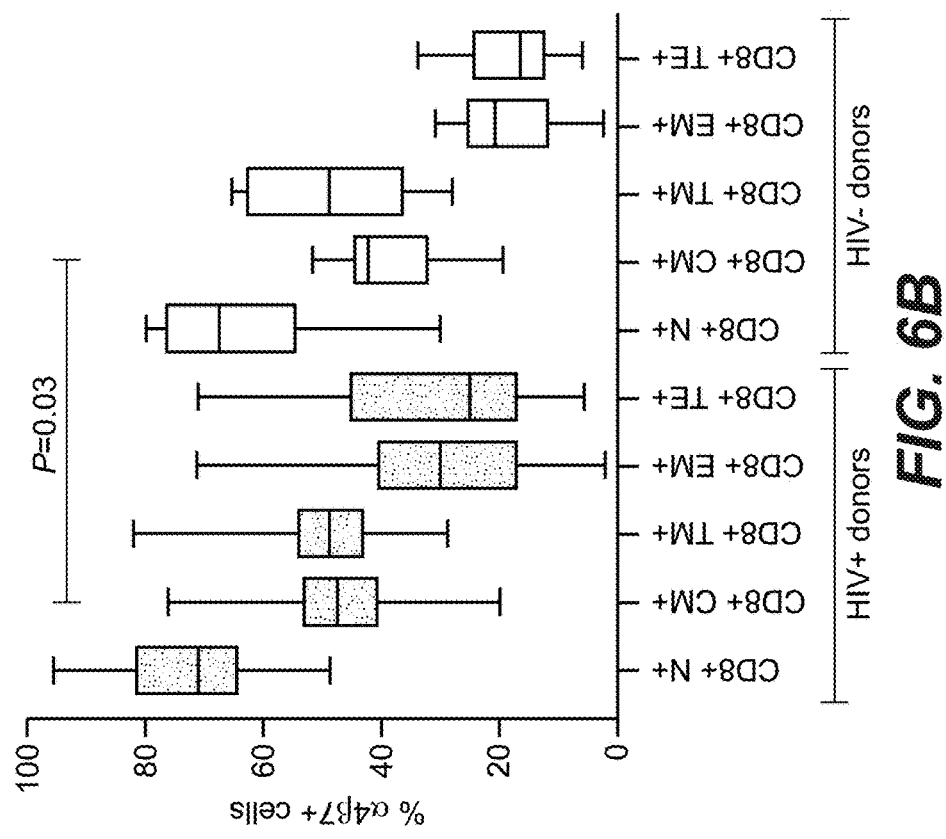
Figure 6A:
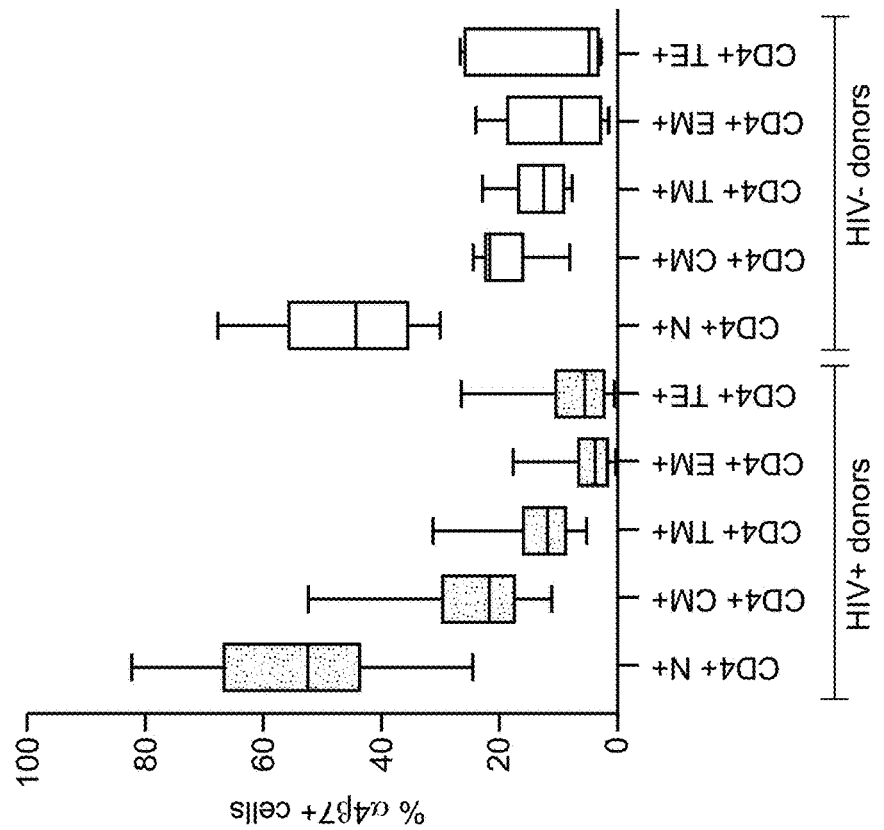
Figures 6C, 6D:
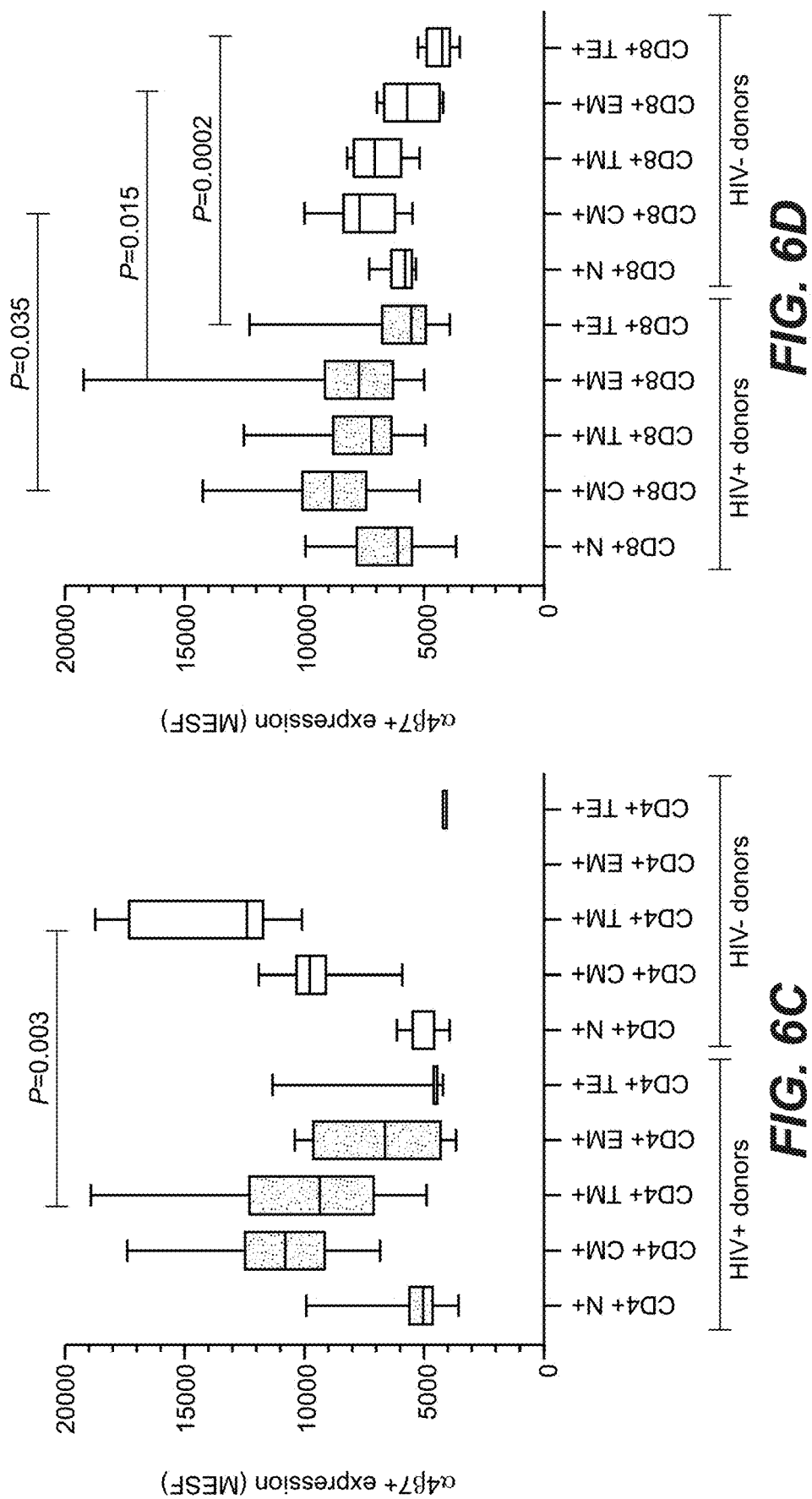
Figures 6E, 6F:
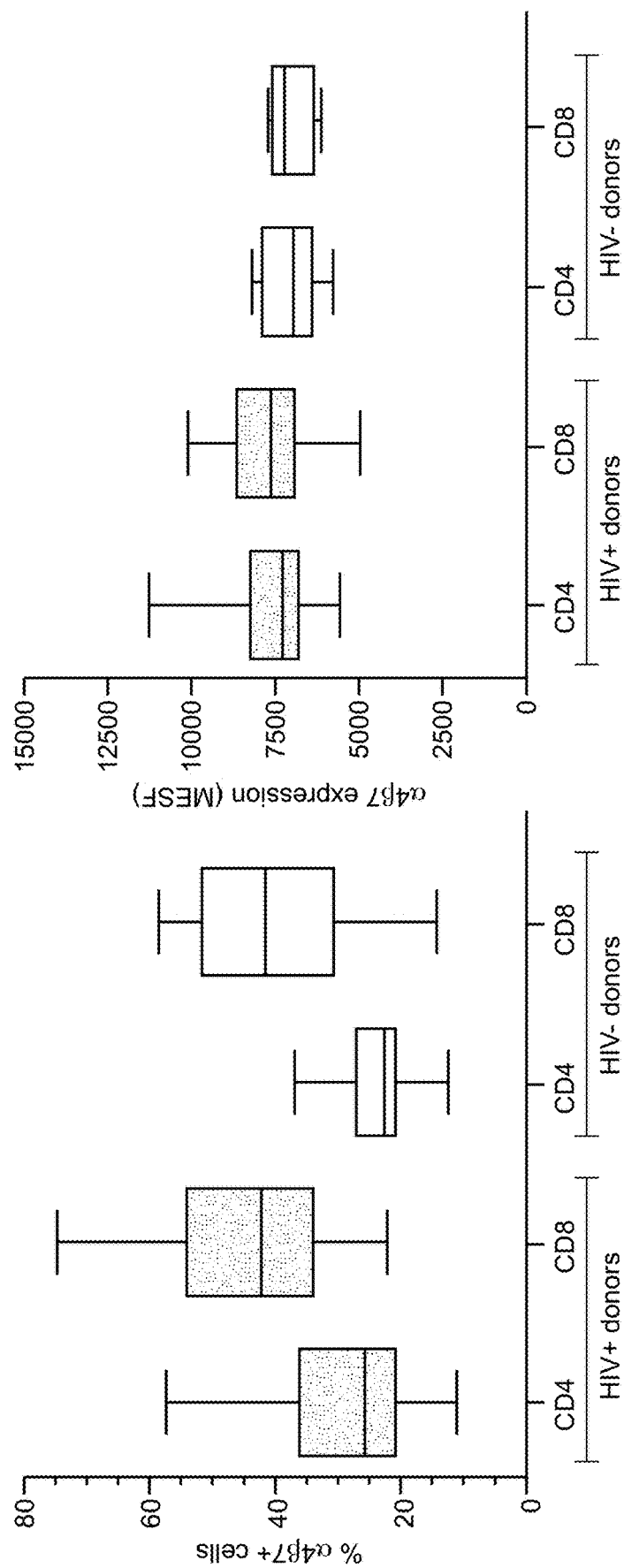

Liability-engineered clones that were identified as binding similarly as parental (FIG. 5) are presented in TABLE 21. These liability-engineered clones along with their variable regions were converted to IgG format.

TABLE 21

Sequences of Selected Clones from Liability Engineering of Ab-H1.9

Heavy Chain

| Antibody | CDR1 | CDR2 | CDR3 | VH |
|---|---|---|---|---|
| Ab-H1.9 (parental) | GFNEKNTYMH SEQ ID NO: 32 | REDPANGHTEYAPKFQG SEQ ID NO: 33 | VDS SEQ ID NO: 34 | SEQ ID NO: 30 |
| Ab-h1.9a | GFNEKNTYMH SEQ ID NO: 42 | REDPANKHTEYAPKFLG SEQ ID NO: 43 | VAS SEQ ID NO: 44 | SEQ ID NO: 40 |
| Ab-h1.9b | GFNEKNTYMH SEQ ID NO: 52 | REDPARGHTEYAPKFSG SEQ ID NO: 53 | VDQ SEQ ID NO: 54 | SEQ ID NO: 50 |
| Ab-h1.9c | GFNEKNTYMH SEQ ID NO: 62 | REDPARGHTEYAPKFEG SEQ ID NO: 63 | VAS SEQ ID NO: 64 | SEQ ID NO: 60 |
| Ab-h1.9d | GFNEKNTYMH SEQ ID NO: 72 | REDPAKGHTEYAPKFLG SEQ ID NO: 73 | VDV SEQ ID NO: 74 | SEQ ID NO: 70 |
| Ab-h1.9e | GFNEKNTYMH SEQ ID NO: 82 | REDPAGGHTEYAPKFIG SEQ ID NO: 83 | VAS SEQ ID NO: 84 | SEQ ID NO: 80 |

Light Chain

| Antibody | CDR1 | CDR2 | CDR3 | VL |
|---|---|---|---|---|
| Ab-H1.9 (parental) | HASQGISDNIG SEQ ID NO: 35 | HGTNLED SEQ ID NO: 36 | VQYAQFPWT SEQ ID NO: 37 | SEQ ID NO: 31 |
| Ab-h1.9a | HASQEISDNIG SEQ ID NO: 45 | HGTNLED SEQ ID NO: 46 | VQYAQFPWT SEQ ID NO: 47 | SEQ ID NO: 41 |
| Ab-h1.9b | HASQDISDNIG SEQ ID NO: 55 | HGTNLED SEQ ID NO: 56 | VQYAQFPWT SEQ ID NO: 57 | SEQ ID NO: 51 |
| Ab-h1.9c | HASQDISDNIG SEQ ID NO: 65 | HGTNLED SEQ ID NO: 66 | VQYAQFPWT SEQ ID NO: 67 | SEQ ID NO: 61 |

TABLE 21-continued

Sequences of Selected Clones from Liability Engineering of Ab-H1.9

| Ab-h1.9d | HASQDISDNIG SEQ ID NO:75 | HGTNLED SEQ ID NO: 76 | VQYAQFPWT SEQ ID NO: 77 | SEQ ID NO: 71 |
|---|---|---|---|---|
| Ab-h1.9e | HASQEISDNIG SEQ ID NO: 85 | HGTNLED SEQ ID NO: 86 | VQYAQFPWT SEQ ID NO: 87 | SEQ ID NO: 81 |

Liability-engineered mAbs Ab-h1.9a through Ab-h1.9e were tested for binding to α4β7-expressing HuT78 cells by FACS. These antibodies retained binding activity, having EC50 values ranging from 253 pM to 702 pM. This retention of α4β7 binding was surprising, given that a large portion of VH-CDR3 (e.g., one third of the amino acid residues in the CDR) was mutated in the liability-engineered mAbs. Ab-h1.9d showed the strongest binding affinity (253 pM) and exhibited good drug-like properties.

Protein production properties of antibodies Ab-h1.9(a)-(e) in human IgG1 Fc LALA format were also tested, and Ab-h1.9d demonstrated superior properties.

7.1.6. Antibodies

Exemplary Ab-h1.9d derived IgG1 antibody conversions are shown in TABLE 22. Ab-h1.9d-HuIgG1 is human IgG1/kappa type antibody having a HC of SEQ ID NO:90 featuring a canonical human heavy chain constant region, and a LC of SEQ ID NO:100 featuring a canonical human kappa light chain constant region. Ab-h1.9d-HuIgG1 may also have a C-terminal lysine truncated HC of SEQ ID NO:91. Ab-h1.9d-WT is an IgG1/kappa type antibody having a HC of SEQ ID NO:92 featuring variant CH3 substitutions D356E and L358M, and a LC of SEQ ID NO:100. Ab-h1.9d-WT may also have a C-terminal lysine truncated HC of SEQ ID NO:93. Ab-h1.9d-LALA is an IgG1/kappa type antibody having a HC of SEQ ID NO:94 featuring variant CH2 substitutions L234A and L235A, and variant CH3 substitutions D356E and L358M, and a LC of SEQ ID NO:100. Ab-h1.9d-LALA may also have a C-terminal lysine truncated HC of SEQ ID NO:95. Ab-h1.9d-QL is an IgG1/kappa type antibody having a HC of SEQ ID NO:96 featuring variant CH2 substitution T250Q, and variant CH3 substitutions D356E, L358M, and M428L, and a LC of SEQ ID NO:100. Ab-h1.9d-QL may also have a C-terminal lysine truncated HC of SEQ ID NO:97. Ab-h1.9d-LALA/QL is an IgG1/kappa type antibody having a HC of SEQ ID NO:98 featuring variant CH2 substitution T250Q, and variant CH3 substitutions L234A, L235A, D356E, L358M, and M428L, and a LC of SEQ ID NO:100. Ab-h1.9d-LALA/QL may also have a C-terminal lysine truncated HC of SEQ ID NO:99. As will be understood by those skilled in the art, numbering of antibody amino acid residues in this paragraph and TABLE 22 is done according to the EU numbering scheme, and therefore differs from the sequential numbering used in the sequence listing.

TABLE 22

Exemplary Selected Antibodies

| Antibody | Features | HC | LC (kappa) |
|---|---|---|---|
| Ab-h1.9d-hIgG1 | IgG1/k | 90 or 91 | 100 |
| Ab-h1.9d-WT | IgG1/k with D356E and L358M | 92 or 93 | 100 |
| Ab-h1.9d-LALA | IgG1/k with L234A, L235A, D356E, and L358M | 94 or 95 | 100 |
| Ab-h1.9d-QL | IgG1/k with T250Q, D356E, L358M, and M428L | 96 or 97 | 100 |
| Ab-h1.9d-LALA/QL | IgG1/k with L234A, L235A, T250Q, D356E, L358M, and M428L M428L | 98 or 99 | 100 |

(SEQ ID NO: 90)
EVQLVQSGAEVKKPGSSVKVSCKASGFNIKNTYMHWVRQAPGQGLEWIGRIDPAKGHTEYAPKFLGRVTITADESTNTAYMELSSLRSEDTAVYYCYYV
DVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK (SEQ ID NO: 91)
EVQLVQSGAEVKKPGSSVKVSCKASGFNIKNTYMHWVRQAPGQGLEWIGRIDPAKGHTEYAPKFLGRVTITADESTNTAYMELSSLRSEDTAVYYCYYV
DVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPG (SEQ ID NO: 92)
EVQLVQSGAEVKKPGSSVKVSCKASGFNIKNTYMHWVRQAPGQGLEWIGRIDPAKGHTEYAPKFLGRVTITADESTNTAYMELSSLRSEDTAVYYCYYV
DVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRV

TABLE 22-continued

Exemplary Selected Antibodies

| Antibody | Features | HC | LC (kappa) |
|---|---|---|---|

VSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK (SEQ ID NO: 93)
EVQLVQSGAEVKKPGSSVKVSCKASGFNIKNTYMHWVRQAPGQGLEWIGRIDPAKGHTEYAPKFLGRVTITADESTNTAYMELSSLRSEDTAVYYCYYV
DVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPG (SEQ ID NO: 94)
EVQLVQSGAEVKKPGSSVKVSCKASGFNIKNTYMHWVRQAPGQGLEWIGRIDPAKGHTEYAPKFLGRVTITADESTNTAYMELSSLRSEDTAVYYCYYV
DVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK (SEQ ID NO: 95)
EVQLVQSGAEVKKPGSSVKVSCKASGFNIKNTYMHWVRQAPGQGLEWIGRIDPAKGHTEYAPKFLGRVTITADESTNTAYMELSSLRSEDTAVYYCYYV
DVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPG (SEQ ID NO: 96)
EVQLVQSGAEVKKPGSSVKVSCKASGFNIKNTYMHWVRQAPGQGLEWIGRIDPAKGHTEYAPKFLGRVTITADESTNTAYMELSSLRSEDTAVYYCYYV
DVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAPELLGGPSVFLFPPKPKDQLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSD
GSFFLYSKLTVDKSRWQQGNVFSCSVLHEALHNHYTQKSLSLSPGK (SEQ ID NO: 97)
EVQLVQSGAEVKKPGSSVKVSCKASGFNIKNTYMHWVRQAPGQGLEWIGRIDPAKGHTEYAPKFLGRVTITADESTNTAYMELSSLRSEDTAVYYCYYV
DVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAPELLGGPSVFLFPPKPKDQLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSD
GSFFLYSKLTVDKSRWQQGNVFSCSVLHEALHNHYTQKSLSLSPG (SEQ ID NO: 98)
EVQLVQSGAEVKKPGSSVKVSCKASGFNIKNTYMHWVRQAPGQGLEWIGRIDPAKGHTEYAPKFLGRVTITADESTNTAYMELSSLRSEDTAVYYCYYV
DVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAPEAAGGPSVFLFPPKPKDQLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSD
GSFFLYSKLTVDKSRWQQGNVFSCSVLHEALHNHYTQKSLSLSPGK (SEQ ID NO: 99)
EVQLVQSGAEVKKPGSSVKVSCKASGFNIKNTYMHWVRQAPGQGLEWIGRIDPAKGHTEYAPKFLGRVTITADESTNTAYMELSSLRSEDTAVYYCYYV
DVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAPEAAGGPSVFLFPPKPKDQLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSD
GSFFLYSKLTVDKSRWQQGNVFSCSVLHEALHNHYTQKSLSLSPG (SEQ ID NO: 100)
DIQMTQSPSSLSASVGDRVTITCHASQDISDNIGWLQQKPGKSFKLLIYHGTNLEDGVPSRFSGSGSGTDYTLTISSLQPEDFATYYCVQYAQFPWTFG
GGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTH
QGLSSPVTKSFNRGEC

After production, Ab-h1.9d-WT showed superior properties for an anti-human α4β7 antibody, demonstrating high specificity (low binding to αEβ7), and desirable PK/PD (low ADA titers and high plasma exposure).

7.2. Example 2: α4β7 Expression on CD4+ and CD8+ T Cell Subsets from Healthy Donors or HIV+ Individuals

7.2.1. Materials and Methods

During acute HIV infection, α4β7 expressing CD4+ T cells are preferentially infected and therefore depleted (Sivro et al., Sci Transl Med 2018). To investigate whether peripheral α4β7-expressing cells recover over time in HIV+ individuals receiving cART, the percentage and expression levels of α4β7 on CD4+ and CD8+ T cell subsets from PBMCs of 10 healthy (HIV−) donors and 45 HIV+ individuals receiving cART (age: 26 to 66 years, median 42 years; duration of HIV infection: 1 to 36 years, median 12 years) were compared by flow cytometry analysis using a cocktail of antibodies for CD3, CD4, CD8, CD28, CD45RO, CCR7, and α4β7. Both percentage (%) and expression level (MESF) of α4β7 in CD4+ and CD8+ T cell populations were analyzed. CD4+ and CD8+ T cell subsets were defined as: CD28+CD45RO− naïve cells, CD28−CD45RO− terminal effector cells, CD28−CD45RO+ effector memory cells, CD28+CD45RO+CCR7+ central memory cells, and CD28+CD45RO+CCR7− transient memory cells.

7.2.2. Results

For both HIV− and HIV+ individuals receiving cART, the percentage of cells expressing α4β7 is higher for naïve CD4+ or CD8+ T cells as compared with memory T cell subsets, while α4β7 expression level (as measured by MESF) was higher on central memory, transient memory, and effector memory cells than naïve cells (FIGS. 6A-6F). Both peripheral CD4+ and CD8+ T cells expressed similar levels of α4β7 in HIV− and HIV+ individuals (MESF measurement). This analysis demonstrated that α4β7 expression on peripheral CD4+ or CD8+ T cells among HIV+ individuals receiving cART, though highly variable, was not different with that from the uninfected individuals. These results suggested that the α4β7 expression in peripheral CD4+ T cells in HIV+ individuals could support the incorporation of α4β7 into the budding HIV virions.

7.3. Example 3: HIV Virion Capture with Ab-h1.9d-WT

7.3.1. Materials and Methods

To confirm α4β7 is present in the envelope of HIV virions, and to test if Ab-h1.9d-WT can bind to α4β7 incorporated into the envelope of HIV virions to form immune complexes, Ab-h1.9d-WT was first tested in a virion capture assay (bead format) using laboratory-grown HIV-1 strains or samples from viremic HIV+ individuals according to a published method (Guzzo et al., Sci Immunol 2017). For laboratory-grown HIV-1 strains, a panel of six strains (BCF06, CMU08, NL4-3, RU507, YBF30, and IIIB) representing different groups, genetic subtypes, and co-receptor usage (TABLE 23), were produced in activated primary human PBMCs [e.g. activated by OKT3 antibody or phytohemagglutinin (PHA)] in the presence of retinoic acid (RA) to induce the expression of α4β in the cells. Protein G-conjugated immunomagnetic beads (Dynabeads, Thermo Fisher) were armed with the appropriate antibody and then incubated with virus stock of each HIV strain (~2 ng p24 gag/reaction). After incubation, the armed beads were washed to remove unbound virus particles, and subsequently treated with Triton X-100 to lyse the captured virions for p24 gag quantification. For HIV patients' samples, the viral titer (copies/mL) of the samples were determined by the COBAS Taqman 2.0 assay. Protein G-conjugated immunomagnetic beads armed with 10 μg of the appropriate antibody were incubated with 400 μL of patient sera for 2 hours. Beads were then washed to remove unbound virus particles, and RNA of the bound virions was subsequently extracted using Qiagen's viral RNA extraction kit per manufacturer's instructions. Copy number of the captured virions from patients' samples was subsequently quantified by digital droplet PCR using primers and probe targeting conserved region in LTR-gag for HIV subtype B.

To determine the $EC_{50}$ values of antibody for capturing HIV virions, Ab-h1.9d-WT was tested in a virion capture assay modified to a 96-well plate format. Serially diluted antibody was added to a prewashed Pierce™ Protein G coated plate (Thermo Fisher). After incubation, the plates were washed to remove unbound antibodies. Viral stock of each HIV strain (approximately 2 ng p24 gag) was added to each well and incubated. Plates were washed to remove unbound viral particles, and then treated with Triton X-100 to lyse the captured virions for p24 gag quantification. HIV p24 gag was detected by high-sensitivity AlphaLISA p24 gag detection kit (Perkin Elmer).

7.3.2. Results

Ab-h1.9d-WT was able to capture virions from all of the six laboratory-grown HIV strains tested, whether they were clinical or laboratory-adapted strains, as indicated by the viral p24 gag protein in the virions captured (FIGS. 7A-7F). The amount of p24 gag protein from captured virions demonstrated a dose response to the antibody concentrations (5 and 15 nM) used in the assay. Ab-h1.9d-WT was also able to capture virions from HIV-1 patients' samples (viral input shown in FIG. 7G-1), as indicated by the higher number of HIV RNA copy number in samples reacted with Ab-h1.9d-WT compared to those with the negative control antibody (FIG. 7G-2).

Ab-h1.9d-WT was next tested in a virion capture assay modified to a 96-well plate format to determine its $EC_{50}$ values for capturing HIV virions. The $EC_{50}$ values were similar for all the viruses tested and ranged from 0.12 nM (0.019 μg/mL) to 0.25 nM (0.038 μg/mL) (TABLE 23). When tested against the same panel of viruses, Ab-Vedo was less potent than Ab-h1.9d-WT in capturing HIV virions, with $EC_{50}$ values ~2-3-fold higher than those of Ab-h1.9d-WT for each individual virus (TABLE 23). HIV IIIB strain could be captured by Ab-h1.9d-WT (FIG. 7F) and Ab-Vedo (data not shown) using the bead format assay, but its EC50 values could not be determined by the plate format assay due to the low titer of the viral stock.

TABLE 23

HIV Virion Capture and Neutralization with Ab-h1.9d-WT In Vitro

| HIV Strain | Group | Sub-type | Co-Receptor | Virion Capture, $EC_{50}$ | | | | Viral Neutralization, $IC_{50}$ |
|---|---|---|---|---|---|---|---|---|
| | | | | Ab-h1.9d-WT | | Ab-Vedo | | Ab-h1.9d-WT |
| | | | | nM | μg/mL | nM | μg/mL | μg/mL |
| BCF06 | O | — | X4/R5 | 0.18 ± 0.03 | 0.027 ± 0.005 | 0.37 ± 0.07 | 0.056 ± 0.010 | >50 |
| CMU08 | M | AE | X4 | 0.25 ± 0.02 | 0.038 ± 0.003 | 0.50 ± 0.08 | 0.075 ± 0.012 | >50 |
| NL4-3 | M | B | X4 | 0.16 ± 0.03 | 0.024 ± 0.005 | 0.34 ± 0.02 | 0.050 ± 0.002 | >50 |
| RU570 | M | G | R5 | 0.12 ± 0.06 | 0.019 ± 0.010 | 0.32 ± 0.03 | 0.048 ± 0.005 | >50 |
| YBF30 | N | — | R5 | 0.14 ± 0.06 | 0.021 ± 0.009 | 0.48 ± 0.15 | 0.072 ± 0.022 | >50 |
| IIIB | M | B | X4 | ND[a] | ND[a] | ND[a] | ND[a] | ND |

$EC_{50}$ = half maximal effective concentration;
$IC_{50}$ = half maximal inhibitory concentration;
ND = not determined
[a] IIIB strain could be captured by Ab-h1.9d-WT and Ab-Vedo in bead assay format, but its EC50 values could not be determined in plate assay format due to the low titer of the viral stock.

Taken together, these data confirmed that α4β7 was present in virions of all laboratory-grown HIV strains and HIV-1 patients' samples tested, and demonstrated that Ab-h1.9d-WT was more potent than Ab-Vedo in binding to α4β7 on HIV virions forming immune complexes, the first of a series of steps required for the induction of the proposed "vaccination effect" for durable HIV viral control.

Ab-h1.9d-WT is a potent anti-α4β7 antibody that can bind to α4β7 on the envelope of virions of all the HIV strains and HIV-1 patients' samples tested.

7.4. Example 4: Binding of Immune Complexes of Ab-h1.9d-WT and HIV Virions to FcγRs

7.4.1. Materials and Methods

To test if the immune complexes formed by Ab-h1.9d-WT and HIV virions could bind to FcγRs in vitro, the appropriate antibody was first mixed with HIV NL4-3 virus (prepared in activated human PBMC in the presence of RA to induce the expression of α4β7) to form immune complexes, which were subsequently incubated with His-tagged FcγRs immobilized on nickel coated plates [for FcγRI and FcγRIIIa (V158), which have relatively higher affinity to Ab-h1.9d-WT, as shown in TABLE 32], or biotinylated FcγRs immobilized on neutravidin coated plates to increase the sensitivity of the detection [for FcγRIIa (H131 or R131) and FcγRIIIa (F158), which have relatively lower affinity to Ab-h1.9d-WT, as shown in TABLE 32]. After incubation, plates were washed to remove immune complexes not bound to FcγRs, and then treated with lysis buffer to lyse the captured immune complexes to release viral proteins for p24 gag quantification.

7.4.2. Results

The immune complexes formed by HIV virions and Ab-h1.9d-WT, which has a WT Fc domain, were able to bind to different FcγRs as shown by the presence of HIV p24 capsid protein in the protein complex bound to the FcγRs (FIGS. 8A-8E). HIV virion by itself did not bind to the FcγRs (data not shown), nor immune complexes formed by HIV virions and Ab-h1.9d-LALA, an antibody identical to Ab-h1.9d-WT except it has engineered LALA mutations in its Fc domain to significantly reduce its binding to FcγRs (FIGS. 8A-8E). In addition, the immune complexes formed by HIV virions and Ab-Vedo demonstrated minimal binding to FcγRs (FIGS. 8A-8E). This is consistent with the significantly lower binding affinity of Ab-Vedo to different FcγRs than Ab-h1.9d-WT due to the engineered mutations in the Fc domain of Ab-Vedo. Due to the lower binding affinity of Ab-h1.9d-WT to human FcγRIIa (H131 or R131) and FcγRIIIa (F158, also known as F176) than FcγRI and FcγRIIIa (V158, also known as V176) (FIG. 19A), biotinylated FcγRIIa (H131 or R131) and FcγRIIIa (F158) were immobilized on neutravidin coated plates to enhance the capture of the immune complexes of Ab-h1.9d-WT by these FcγRs instead of using the corresponding His-tagged FcγRs immobilized on nickel plates.

The immune complexes formed by Ab-h1.9d-WT and HIV virions could bind to different FcγRs including FcγRIIa (responsible for ADCP), a step that could enable the complexes to be taken up by APCs to induce the proposed "vaccination effect" for HIV control.

7.5. Example 5: Ab-h1.9d-WT Mediates Fc-Dependent Uptake of α4β7-Coated Beads in THP-1 Cells

7.5.1. Materials and Methods

Cell Culture

THP-1 cells were cultured at 37° C., 5% $CO_2$ in RPMI media (Gibco) supplemented with 10% FBS (Sigma). Cells were passaged every two to three days and maintained at a density of 500,000-1,000,000 cells/ml.

Bead Preparation

Recombinant human α4β7 protein (R & D systems) was dialyzed overnight at 4° C. in 1×PBS using a 3.5 kDa MWCO dialysis device (Thermo Fisher Scientific Inc.). The resulting α4β7 was then biotinylated at 100× molar excess NHS-Biotin (Thermo Fisher Scientific Inc.) for 2 h at 4° C. Excess biotin was removed by overnight dialysis at 4° C. For α4β7 coated beads, NeutrAvidin-labeled fluorescent beads (Thermo Fisher Scientific Inc.) were incubated with biotinylated α4β7 for 1-24 h at 4° C. Bead-protein conjugation reactions occurred at a ratio of 2 mg α4β7 protein per 1 ml of stock beads, unless otherwise stated. Protein conjugated beads were washed twice with 1×PBS containing 1% BSA (Sigma), then diluted 100× prior to use. Successful conjugation of protein to beads was confirmed in phagocytosis assays comparing anti-α4β7 with isotype control conditions.

Phagocytosis Assay

Phagocytosis assays using protein coated beads and THP-1 cells were adapted from a previously described study (Ackerman et al 2011). Assays were performed in 96 well plates. Immune complexes were formed by combining 10 ul of prepared α4β7 coated beads with 10 ul of the indicated antibody (10 μg/ml). These were incubated for 1-2 h at 37° C., 5% $CO_2$. THP-1 cells (100,000/well) were then incubated with immune complexes for the indicated amount of time in a final volume of 200 ul. Following incubation, cells were stained with a fixable live/dead stain (ThermoFisher), followed by washing with FACS buffer and fixation. Data on resulting cells were collected using a LSR Fortessa X20 from BD. Fluorescent beads and live/dead stain fluorescence were detected with the PE-CF594 and BV510 settings, respectively. Data were then analyzed using FlowJo software. Phagocytosis score was calculated as follows: phagocytosis score=(MFI×percent bead positive cells)/1000. Normalization: Data from 3 independent experiments were normalized and plotted on one graph. To normalize, one replicate in the "beads only" condition was set to 1 by dividing this value by the same value (done for each experiment). All other values were divided by this normalization value to display the normalized phagocytosis score, which represents fold change from the "beads only" condition.

Imaging Flow Cytometry

Internalization of beads were confirmed using imaging flow cytometry. Fixed cells were analyzed on ImagestreamX Mark II imaging flow cytometer (Luminex Corp.) at 40× magnification and medium sensitivity and medium speed setting. Fluorescent beads were imaged using 488 nm (5 mW)/560-595 nm (excitation/emission). Live/dead stain was imaged using 405 nm (5 mW)/430-480 nm (excitation/emission). Brightfield image was collected in channel 2 (camera 1). Data was analyzed using IDEAS analysis software v6.1 (Luminex Corp.). Standard gating strategy was used to find appropriate cell populations. Briefly, focused cells were identified using high (>40) gradient RMS (root mean square) for brightfield image sharpness. Single cells were identified by high aspect ratio and low object area of brightfield image. Cellular object area was identified in the brightfield image and 4 pixels were eroded from the cell boundary to define an 'intracellular mask'. Cells with positive fluorescence signal in the intracellular mask were identified as true internalization events. Spot count feature was used to count the number of internalized beads in cells with true internalization events. At least 2000 cells with true internalization events were analyzed per sample.

Statistical Analysis

Data were plotted using GraphPad Prism. Significance was determined using one-way ANOVA coupled to Tukey's multiple comparisons test. **$p<0.0001$, *$p=0.0001$-0.001, **$p=0.001$-0.01, *$p=0.01$-0.05.

7.5.2. Results

Uptake of immune complexes by antigen presenting cells is critical to initiate downstream cellular and humoral immunity. THP-1 cells have been reported to phagocytose antibody-fluorescent bead immune complexes in an Fc/FcγR-dependent manner (Ackerman et al., 2011). Therefore, THP-1 cells were used to investigate whether Ab-h1.9d-WT mediates phagocytosis of α4β7-coated fluorescent beads. Cells treated for 3 h with α4β7-beads/Ab-h1.9d-WT antibody immune complexes displayed significant uptake of fluorescent beads relevant to Ab-h1.9d-LALA and Ab-Vedo (featuring LALA) by flow cytometry (FIGS. 9A-9B). LALA mutations are known to drastically reduce IgG Fc binding to FcγRs. These data suggest that Ab-h1.9d-WT mediates robust Fc/FcγR-dependent phagocytosis of immune complexes containing α4β7-coated fluorescent beads.

Imaging flow cytometry with the Amnis Imagestream was performed to confirm that Ab-h1.9d-WT/α4β7-bead immune complexes were internalized in THP-1 cells. As expected, fluorescent beads were localized within THP-1 cells after Ab-h1.9d-WT immune complex treatment (FIG. 9C

7.6. Example 6: Ab-h1.9d-WT-Induced Uptake of α4β7+GFP+VLPs/Ab Immune Complex in THP-1 Cells is α4β7- and Fc-Dependent

7.6.1. Materials and Methods

Antibody binding to α4β7-expressing GFP+ viral like particles (VLPs) by ELISA

α4β7+GFP+VLPs were generated from HEK293 cells sequentially transfected with α4β7 cDNA construct and HIV gag-GFP DNA construct, followed by the purification of VLPs from the cell culture supernatants. ELISA was performed to confirm the expression of α4β7 on the GFP+ VLP surface and the binding specificity by various testing Abs. Briefly, each well of a high binding flat-bottomed 96-well plate was coated with 50 µL of α4β7+GFP+VLPs at a concentration of 7.5×107 particles/mL in PBS and incubated overnight at 4° C. The wells were washed with PBS+1% FBS and blocked with 100 µL of a superblock solution for 30 min at room temperature (RT). After three washes, each well was incubated with 50 µL of 4-fold serially diluted primary antibody in PBS+1% FBS for 1 h at RT, followed by washing and incubation with 50 µL of an HRP-conjugated donkey anti-human IgG-Fcγ-specific secondary antibody in PBS+1% FBS for 1 h at RT. After final washes, TMB substrate was added to each well for color development, and the reaction was stopped by adding 2N H2SO4. The optical density (OD) for each well was measured by a plate reader at 450 nm.

Internalization of α4β7+GFP+VLPs/Anti-α4b7 Immunocomplex in THP-1 Cells

For α4β7+GFP+VLP uptake experiments, $5 \times 10^4$ THP-1 cells were mixed in a flat-bottomed 96-well plate without or with an antibody at the final concentration of 1 µg/ml and α4β7+GFP+VLPs at the cell-to-particle ratio of 1:100 in 100 µL volume of RPMI, 10% FBS. The plate was incubated for 16 h at 37° C. in a $CO_2$ incubator. Cells were then resuspended and transferred to a V-bottom 96-well plate to wash once with 200 µL of PBS, 2% FBS through centrifugation. Cell pellet was resuspended in 200 µL of PBS, 0.5% paraformaldehyde and subjected to the determination of percent GFP+ cells by flow cytometry.

For the inhibition of VLP uptake, THP-1 cells (0.5×106/mL) were pretreated with or without Latrunculin A (Lat A) at a final concentration of 240 nM or with 0.1% DMSO (control) for 2 h at 37° C. in a $CO_2$ incubator, followed by the incubation with or without antibody and α4β7+GFP+VLPs, as indicated above.

7.6.2. Results

Ab-h1.9d-WT-Induced Uptake of α4β7+GFP+VLPs/Ab Immune Complex in THP-1 Cells is α4β7- and Fc-Dependent Recombinant viral like particles (VLPs) generated from mammalian cells have dynamic sizes ranging from 0.1 to 0.2 microns. Thus, they are more similar in size to virions than the fluorescence-labeled beads used in the previous experiments and were utilized as a tool to model the internalization/uptake of α4β7+ virions/Ab immune complex by THP-1 cells. The purified α4β7-expressing GFP+VLPs was evaluated for their ability to bind anti-α4β7 Abs via ELISA. As shown in FIG. 10, Ab-h1.9d-WT, Ab-h1.9d-LALA and Ab-Vedo bound to the α4β7+GFP+VLPs comparably with the similar binding EC50 values (0.050 nM, 0.048 nM and 0.058 nM, respectively), while an isotype control Ab (anti-CMV IgG) did not bind at all to the α4β7+GFP+VLPs. This data suggests that various anti-α4β7 Abs can bind α4β7+GFP+VLPs with good binding affinity and specificity.

Next, the uptake of α4β7+GFP+VLPs by THP-1 cells was evaluated in the presence of various anti-α4β7 Abs with or without the functional Fc. As shown in FIG. 11A, Ab-h1.9d-WT treatment induced the detection of more than 60% GFP+ THP-1 cells compared to 1.2% GFP+ cells by an isotype Ab control treatment representing a 50-fold induction of GFP+ cells. This suggests that α4β7+GFP+VLP uptake by THP-1 cells is Ab-h1.9d-WT-specific and depends on α4β7 expression. However, Ab-h1.9d-LALA or Ab-Vedo (LALA) showed only minimal levels of VLP uptake in THP-1 cells, suggesting that anti-α4β7 Ab-induced α4β7+GFP+VLP uptake by these cells requires functional Fc domain of the antibody to enable Fc/FcγR mediated internalization of immune complex, in addition to its α4β7-binding Fab domain.

To confirm that Ab-h1.9d-WT mediated uptake of α4β7+GFP+VLPs is truly due to the internalization, not merely binding to the cell surface FcγRs, a known internalization inhibitor, Latrunculin A (Lat-A), was used to pre-treat THP-1 cells prior to their incubation with Ab/VLP immune complex. Shown in FIG. 11B, there was a 40% reduction of GFP+ cells in Lat A-treated cells compared to untreated cells. This suggests that at least 40% of the total GFP signals observed in untreated (mock) or DMSO-treated control resulted from Ab-h1.9d-WT dependent VLP internalization in THP-1 cells.

7.7. Example 7: Ab-h1.9d-WT Demonstrated No Neutralization Activity Against HIV

7.7.1. Materials and Methods

Some Abs that can bind to HIV virions, e.g. HIV broad neutralizing antibodies, are capable of blocking viral infection. To test if the binding of Ab-h1.9d-WT to α4β7 on HIV virions could block HIV infection of the host cells, it was evaluated in a viral neutralization assay using the TZM-b1 indicator cell line (Arrildt et al., J Virol 2015).

HIV Neutralization Assay

HIV virus (prepared with PHA and RA) corresponding to approximately 150,000 RLU (previously determined by viral titration on TZM-b1 cells) was preincubated with serially diluted antibodies. TZM-b1 cells containing DEAE-dextran were added to the mixture containing pre-incubated HIV and antibodies, and then incubated for 48 hours at 37° C. The cells were treated with Bright-Glo (Promega), and luciferase signal was measured.

7.7.2. Results

When tested against the panel of HIV strains shown in TABLE 23, Ab-h1.9d-WT did not demonstrate any neutralization activity at a concentration up to 50 µg/mL, whereas a HIV broad neutralizing antibody targeting the CD4+ binding site had neutralization $IC_{50}$ values of approximately 0.1 µg/mL against all of the Group M HIV strains tested (i.e., CMU08, NL4-3, and RU570) (data not shown).

Although Ab-h1.9d-WT binds HIV virions, it does not neutralize HIV infection, which is consistent with the notion that α4β7 is not a viral receptor on host cells. This observation supports the hypothesis that targeting α4β7 and not a virally encoded glycoprotein may avoid viral resistance mechanisms.

7.8. Example 8: Inhibition of the Interaction of α4β7 with HIV Gp120 by Different Antibodies

7.8.1. Materials and Methods

The interaction between α4β7 and HIV gp120 has been reported to activate LFA-1, potentially facilitating cell-to-cell transmission of HIV (Arthos et al. Nat Immunol 2008). To test if Ab-h1.9d-WT could disrupt this interaction, an α4β7/gp120 binding assay was set up using α4β7-expressing RPMI 8866 cells binding to a HIV gp120-V2 peptide immobilized on a plate according to a published method (Peachman et al., PloS One). NeutrAvidin coated high capacity 96-well plate (Thermo Fisher) was coated with biotinylated HIV gp120-V2 WT or gp120-V2 control peptide (TABLE 24). The sequences of the two biotinylated peptides were identical except four amino acids reported to mediate binding between α4β7 and gp120 were mutated in the control peptide.

TABLE 24

Biotinylated HIV gp120-V2 Peptides

| Peptide | Amino Acid Sequence* |
|---|---|
| gp120-V2 WT | Biotin-Ttds-CSFNMTTELRDKKQKVHALFYKLDIVPIEDNTSSSEYRLINC-NH2 (SEQ ED NO: 7) |
| gp120-V2 control | Biotin-Ttds-CSFNMTTELRDKKQKVHALFYKAAAAPIEDNTSSSEYRLINC-NH2 (SEQ ED NO: 8) |

*Amino acids different between the two peptides are shown in bold.

Before adding the antibody-cell mixture, the peptide-coated plates were washed to remove the unbound peptides. To generate the antibody-cell mixture stock, RPMI 8866 cells ($8 \times 10^6$ cells/mL) were resuspended in a cold blocking buffer supplemented with $MnCl_2$ at a final concentration of 2 mM to activate the conformation of α4β7. Serially diluted Ab-h1.9d-WT, Ab-Vedo, or isotype negative control antibody was mixed with the $MnCl_2$-treated cells, and the mixture was incubated. The antibody-cell mixture ($2 \times 10^5$ cells in 50 µL per well) was added to each well of the plate coated with the gp120 peptides and incubated. The plate was washed, and viable cells attached to the peptide-coated plate were determined by CellTiter-Glo 2.0 reagent (Promega).

7.8.2. Results

The specificity of this assay was demonstrated by the binding of α4β7-expressing RPMI 8866 cells to a HIV gp120-V2 WT peptide immobilized on a plate, but not to an immobilized gp120-V2 control peptide (FIG. 12A) which harbored mutations at 4 amino acids reported to mediate the binding of gp120 to α4β7 (TABLE 24). When tested in this assay format, Ab-h1.9d-WT blocked the binding of RPMI 8866 cells to the HIV gp120-V2 WT peptide with an $IC_{50}$ value of 0.022±0.016 µg/mL (FIG. 12B). Ab-Vedo had an $IC_{50}$ value (0.042±0.023 µg/mL) higher than that of Ab-h1.9d-WT when tested in the same assay, indicating that it was less potent than Ab-h1.9d-WT in blocking this interaction (FIG. 12B). Taken together, these results indicate that Ab-h1.9d-WT can effectively disrupt the interaction of α4β7 with gp120, potentially inhibiting the cell-to-cell viral spread.

When tested in this assay format, Ab-h1.9d-WT blocked the binding of RPMI 8866 cells to the HIV gp120-V2 WT peptide with an $IC_{50}$ value of 0.022±0.016 µg/mL (FIG. 12B). These results indicate that Ab-h1.9d-WT can effectively disrupt the interaction of α4β7 with gp120, potentially inhibiting the cell-to-cell viral spread.

7.9. Example 9: Binding of Ab-h1.9d-WT to Human and Cynomolgus Monkey Cells Expressing α4β7 Integrin

7.9.1. Materials and Methods

The binding of Ab-h1.9d-WT was evaluated on HuT78 cells (human T lymphoma cells expressing endogenous α4β7) using ECL binding assay and on human and cynomolgus monkey peripheral lymphocytes using flow cytometry.

Additionally, the binding $EC_{50}$ values of Ab-h1.9d-WT were determined and compared for both human and cynomolgus blood-derived total, naive, and memory CD4+ and CD8+ T cells.

ECL Cell Binding Assay

HuT78 cells expressing endogenous α4β7 were cultured in IMDM media containing 20% FBS, Penicillin (50 units/mL)/Streptomycin (50 µg/mL). HuT78 cells were harvested, washed 1× and resuspended in DPBS at $1.5 \times 10^6$ cells/mL. Cells ($7.5 \times 10^4$ in 50 µL) were added to each well of MSD high binding plate(s). Fetal bovine serum at 6.7% (diluted in DPBS) was added and plate(s) were incubated at 37° C. for one hour. Supernatant was removed and 25 µL of titrated Ab-h1.9d-WT antibody or isotype control prepared through 1:4 fold 8-point dilutions ranging from 1.5 µg/mL to 0.000091 µg/mL (in DPBS buffer containing 5% FBS, and 1 mM $MnCl_2$) were added to each well and then plates were incubated at 37° C. for one hour. Plates were washed 2× with DPBS and 25 µL of goat anti-human Ab sulfo tag at a 1:500 dilution in 5% FBS/DPBS/1 mM $MnCl_2$ was added to each well, followed by incubation at 37° C. for 30 minutes. Cells were washed twice with DPBS and then 150 µL of 2×MSD read buffer T was added to each well. Plate(s) were read on Sector Imager 6000 reader and binding curves and binding $EC_{50}$ values were generated using GraphPad Prism 7.0 software.

Human and Cynomolgus Monkey Peripheral T Cell Binding Assay

Frozen human or cynomolgus PBMCs (isolated from blood donors using standard Ficoll Paque isolation method) were thawed in RPMI1640/10% FBS media, washed 1× with FACS buffer (DPBS, w/o $Ca^{+2}/Mg^{+2}$, 1% BSA) and resuspended in FACS buffer containing 5% goat serum. Cells at $\sim 1$-$2 \times 10^5$ (in 100 µL) were added to a 96-well U-bottom plate and incubated on ice for 30 minutes. Plate was centrifuged and supernatants were removed. Titrated Ab-h1.9d-WT or isotype control (25 µL) prepared through 1:5 fold dilution with final concentrations ranging from 5 to 0.000016 µg/mL diluted in FACS buffer containing 5% goat serum and fluorochrome-labeled antibody cocktail (25 µL) were added to each well and then plate was incubated on ice for one hour. At the same time, compensation and FMO controls were also prepared. Following incubation, cells were centrifuged and washed 2× with FACS buffer. Secondary antibody (PE-conjugated) was diluted 1:2,000 in FACS buffer containing 5% goat serum and 50 µL was added to each well. Plate was incubated on ice for one hour. Following incubation, cells were washed 2× with FACS buffer, resuspended in 200 µL of 0.5% PFA in PBS. The plate was read on FACS (Canto II, BD) and live cells were gated based on forward and side scatters. Flow data (FCS 3.0 files) was analyzed using FlowJo Version 10 software and binding curves and binding $EC_{50}$ values were generated using GraphPad Prism 7.0 software.

7.9.2. Results

ECL Cell Binding

As summarized in TABLE 25, Ab-h1.9d-WT displayed binding $EC_{50}$ values of 26 pM, 130 pM, 62 pM for HuT78 cells, human and cynomolgous monkey blood derived lymphocytes, respectively.

TABLE 25

| Binding of Ab-h1.9d-WT to HuT78 Cells and Lymphocytes *EC50 (pM) (Mean ± SD) | | |
|---|---|---|
| ECL | FACS | |
| HuT78 | Human Lymphocytes | Cynomolgus lymphocytes |
| 26 ± 2 | 130 ± 85 | 62 ± 46 |

*Average ± SD; N = 3 (Human) or N = 5 (Cynomolgus)

Human and Cynomolgus Monkey Peripheral T Cell Binding Assay

The binding $EC_{50}$ values of Ab-h1.9d-WT for both human and cynomolgus blood-derived total, naive, and memory CD4+ and CD8+ T cells are shown in TABLE 26.

TABLE 26

| | Binding $EC_{50}$ of Ab-h1.9d-WT to Human and Cynomolgus Monkey T Cell Subsets | | | | | |
|---|---|---|---|---|---|---|
| | EC50 (pM) (Mean ± SD) | | | | | |
| Species | Total CD4+ T Cells | CD4+ Naïve T Cells | CD4+ Memory T Cells | Total CD8+ T Cells | CD8+ Naïve T Cells | CD8+ Memory T Cells |
| Human[a] | 63 ± 38 | 84 ± 32 | 20 ± 12 | 165 ± 121 | 144 ± 120 | 52 ± 51 |
| Cyno monkey[b] | 30 ± 16 | 45 ± 27 | 10 ± 12 | 35 ± 25 | 42 ± 26 | 36 ± 30 |

CD4+ naïve = CD4+CD45RA+CCR7+ cells,
CD4+ memory = CD4+CD45RA− cells

CD8+ naïve = CD8+CD45RA+CCR7+ cells,
CD8+ memory = CD8+CD45RA− cells

[a]Human PBMC = 3 donors

[b]Cynomolgus PBMC = 5 donors

The average binding EC$_{50}$ values range from 10 to 165 pM on all the T cell subsets evaluated. Ab-h1.9d-WT binds very similarly to human and cynomolgus CD4+ and CD8+ T cells or their subsets, since the mean EC$_{50}$ values for each corresponding cell-type vary only by 2- to 3-fold between these two species.

The binding of Ab-h1.9d-WT to human and cynomolgus monkey CD4+ and CD8+ T subsets was also analyzed to compare percentage of Ab-h1.9d-WT bound T cell subsets, shown in FIG. 13. Overall, the percentage of Ab-h1.9d-WT bound cells in each T cell subset are comparable between human and cynomolgus monkey. These findings were not surprising due to the fact that both α4 and β7 from human and cynomolgus are highly homologous (97% amino acid identity, see TABLE 27).

TABLE 27

Amino Acid Identity (%) of α4 and β7 Amongst Species

| Integrin | Cynomolgus Monkey | Rabbit | Rat | Mouse |
|---|---|---|---|---|
| Human α4 | 97 | 89 | 84 | 84 |
| Human β7 | 97 | 88 | 86 | 86 |

Furthermore, functional cross-reactivity of Ab-h1.9d-WT to cynomolgus monkey was confirmed in an in vivo study. Repeated dosing of Ab-h1.9d-WT in cynomolgus monkeys resulted in increased peripheral blood CD4+ T cell counts when the α4β7 receptors were fully occupied. These data demonstrated the on-target functional pharmacodynamic effect of Ab-h1.9d-WT and supported cynomolgus monkey as a pharmacologically relevant species for toxicological evaluation of Ab-h1.9d-WT.

In summary, Ab-h1.9d-WT binds strongly to both human and cynomolgus monkey CD4+ and CD8+ T subsets, demonstrating excellent cynomolgus binding cross-reactivity.

7.10. Example 10: Integrin Binding Specificity of Ab-h1.9d-WT

7.10.1. Materials and Methods

Recombinant cells expressing individual human and cynomolgus monkey heterodimeric integrin α4β7, α4β1 and αEβ7 enabled the evaluation of binding specificity of Ab-h1.9d-WT.

Ab-h1.9d-WT was also evaluated for non-specific binding to human epithelial HEK293 cells.

Integrin Binding Specificity Assay

Various human and cynomolgus integrins (α4β7, α4β1 or αEβ7) expressing CHO-K1 or BAF3 cells, except for cynomolgus α4β1 were harvested, counted and prepared in FACS buffer (DPBS, w/o Ca$^{+2}$/Mg$^{+2}$, 1% BSA) at a density of 1.5×10$^6$ cells per milliliter. A 100 μL containing 1.5×10$^5$ cells was added to each well of a 96-well U-bottom plate and centrifuged to remove supernatant. Titrated Ab-h1.9d-WT, assay control or isotype control (100 μL each) in FACS buffer were added to reconstitute cell pellets. Well contents were mixed, followed by a one-hour incubation on ice. Cells were washed 2× with FACS buffer and then 100 μL of 1:600 diluted secondary antibody (goat anti-hu IgG Fcγ specific Alexa Fluor 488) in FACS buffer was added to each well and mixed. Plate was incubated for 45 minutes on ice. Subsequently, cells were washed 2× with FACS buffer and resuspended in 200 μL of 0.5% PFA in PBS. The plate was read on FACS (Canto-II, BD) and live cells were determined based on forward and side scatters. Median fluorescence intensities for cell-bound antibodies were generated using GraphPad Prism 7.0 software.

For CHO-K1 cells expressing cynomolgus α4β1, an antibody staining cocktail containing 25 μL of CD29-APC and CD49d-BV421 mixture each at 1:25 dilution, and 25 μL of Ab-h1.9d-WT, assay control or isotype control prepared by 1:5 fold serial dilutions in FACS buffer were added to each well of a 96-well U-bottom to reconstitute cynomolgus α4β1 cell pellets. Well contents were mixed, followed by a 45 minute incubation on ice. In conjunction, staining controls were also prepared. Cells were washed 2× with FACS buffer and then 50 μL of 1:600 diluted secondary antibody (goat anti-hu IgG Fcγ specific PE) in FACS buffer was added to each well and mixed. Plate was incubated for another 45 minutes on ice. Subsequently, cells were washed 2× with FACS buffer and resuspended in 200 μL of 0.5% PFA in PBS. The plate was read on FACS (Canto-II, BD) and live cells were gated based on forward and side scatters. CD29+ CD49d+ cells were then gated to determine median fluorescence intensities for cell-bound test antibodies using FlowJo Version 10 software. The data were plotted using GraphPad Prism 7.0 software.

Non-Specific HEK293 Cell Binding Assay

HEK293G cells were cultured in complete DMEM (DMEM+10% FBS+1% Na Pyruvate). Cells were harvested using non-enzymatic dissociation buffer (Gibco, Cat 13151-014), counted and resuspended at 1.5×10$^6$ cells/mL in FACS buffer (2% BSA/PBS). To each well of a 96-well U-bottom plate, 7.5×10$^4$ cells were dispersed. Ab-h1.9d-WT, positive control antibody or isotype control antibody was added to each well at 100 μg/mL and incubated on ice for one hour. Following incubation, cells were washed 2× with FACS buffer and further incubated with 100 μL of 1:100 diluted goat anti-huIgG Fc-PE (Jackson, Cat 109-116-098) in FACS buffer for 30 minutes on ice. Subsequently, cells were washed 2× with FACS buffer and resuspended in 200 μL FACS buffer. The plate was read by FACS (Canto II, BD). Binding data was analyzed using GraphPad Prism 7.0 software.

7.10.2. Results

Integrin Binding Specificity

Figure 14A:
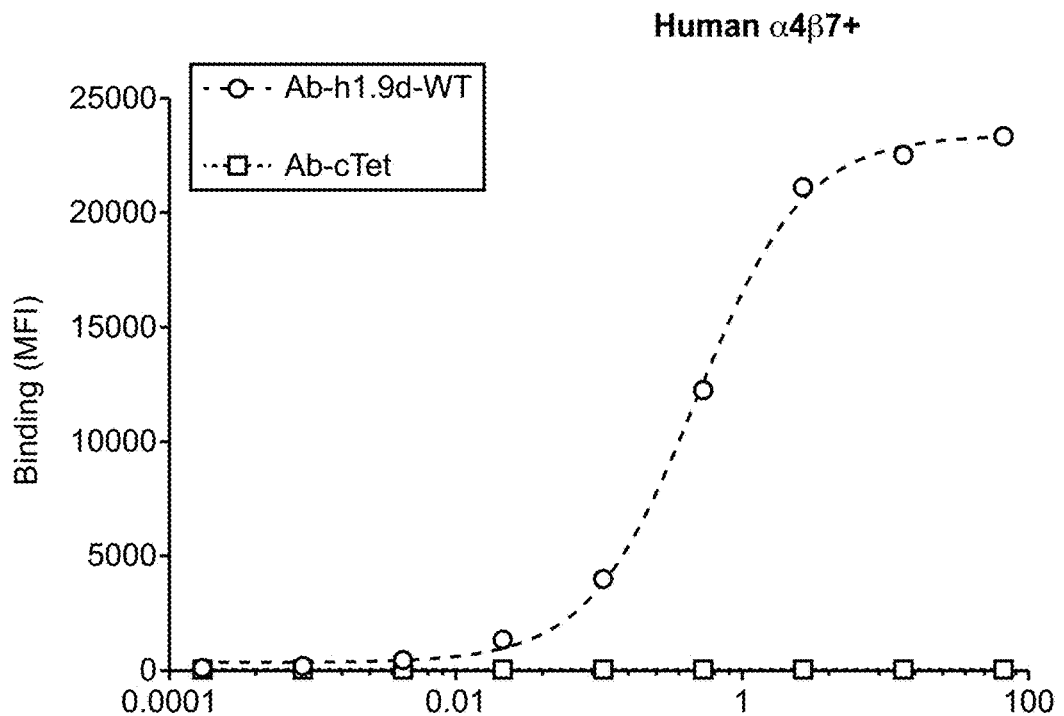
Figure 14B:
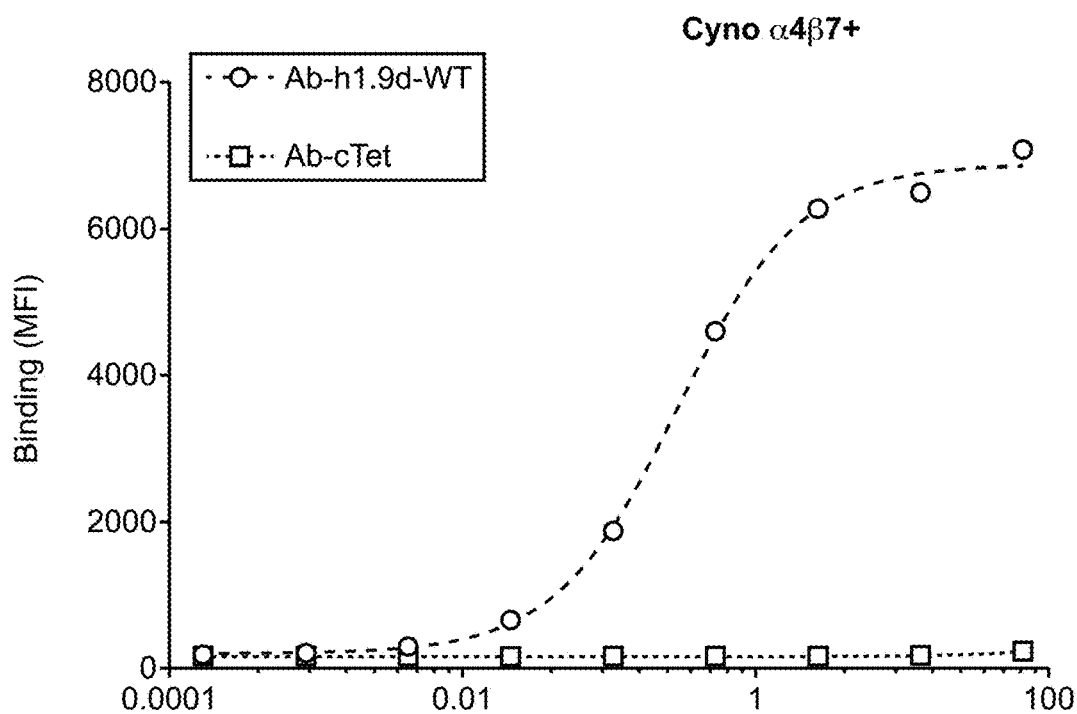
Figure 14C:
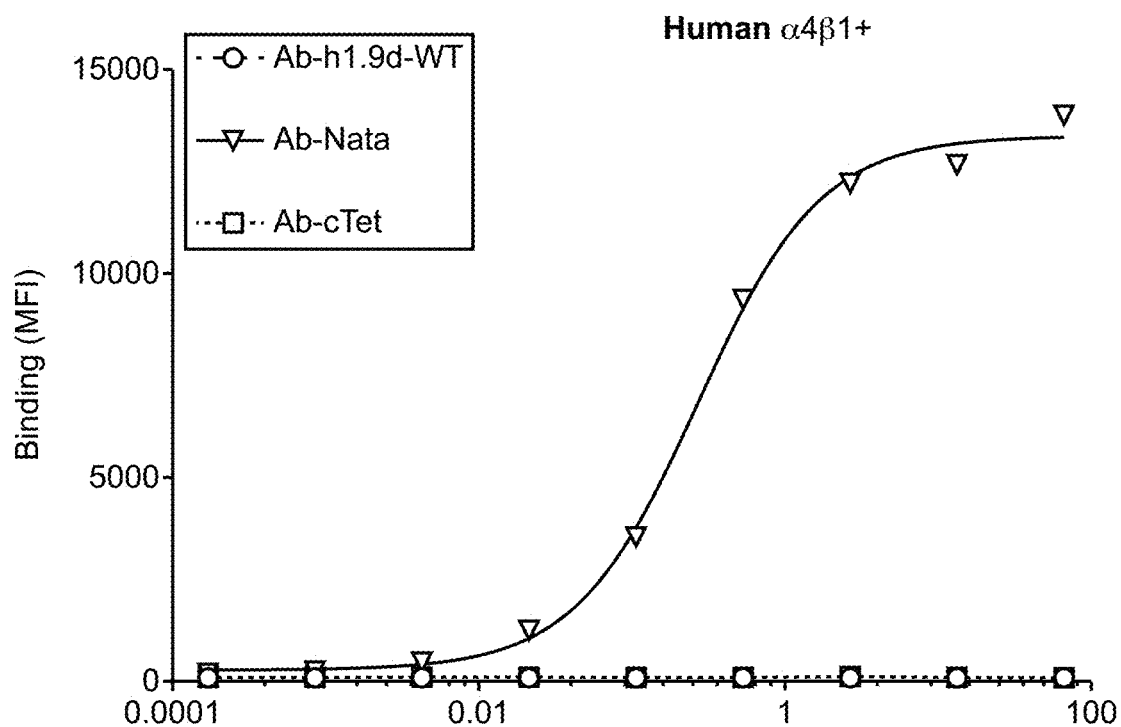
Figure 14D:
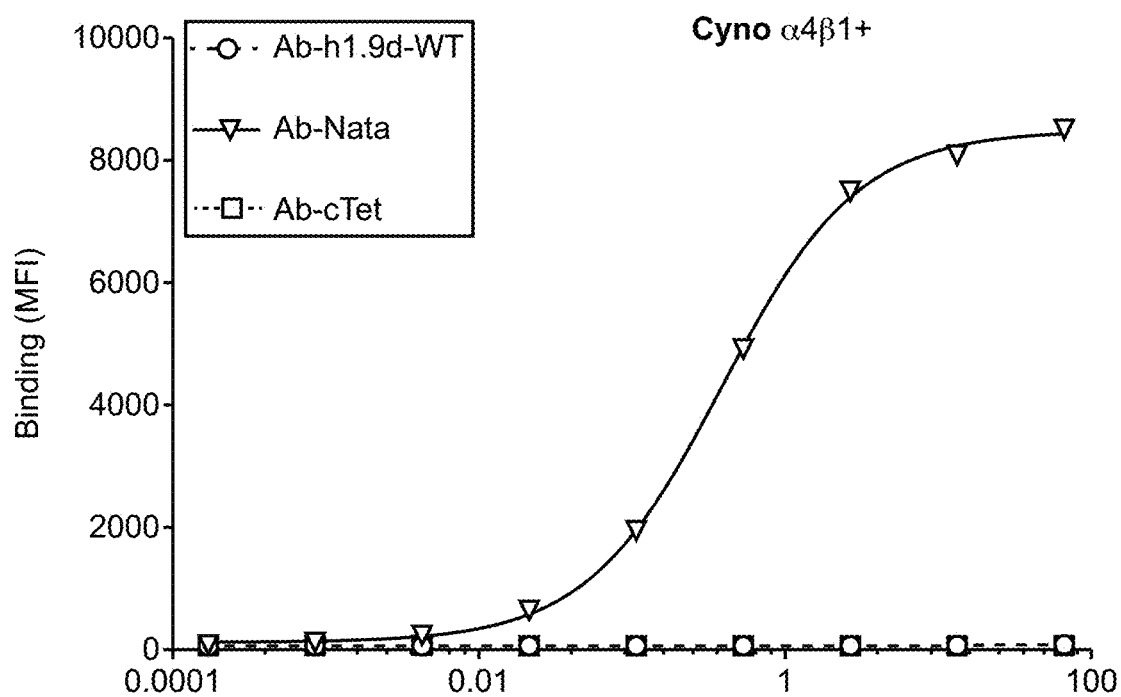
Figure 14E:
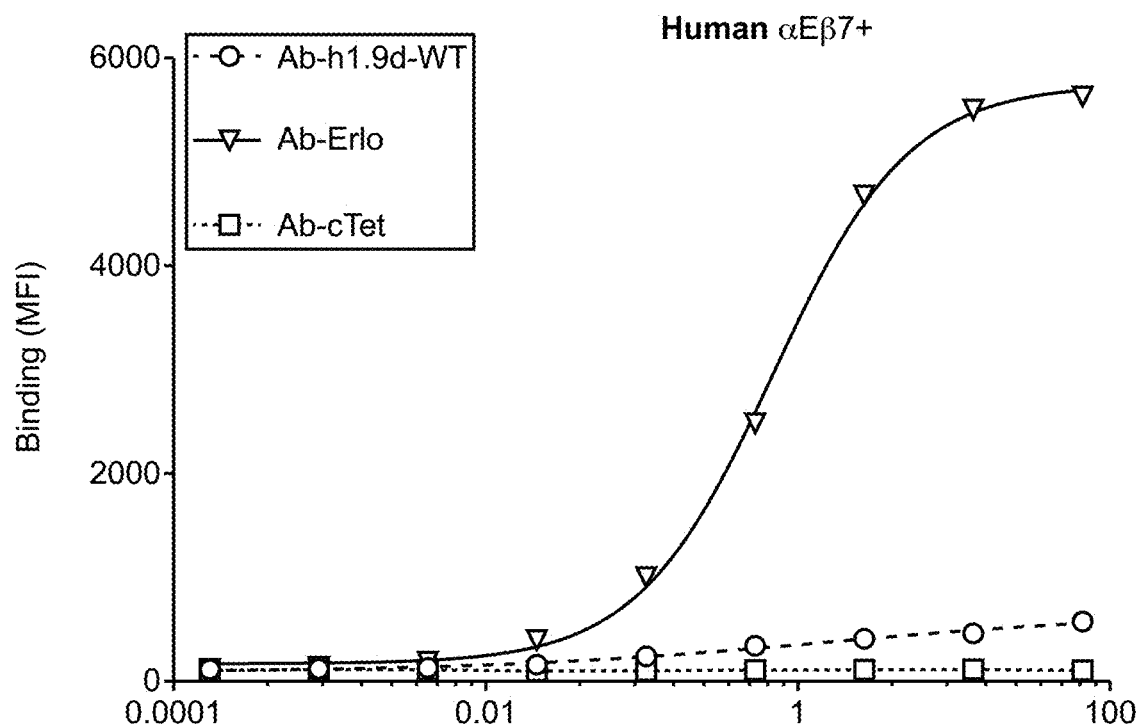
Figure 14F:
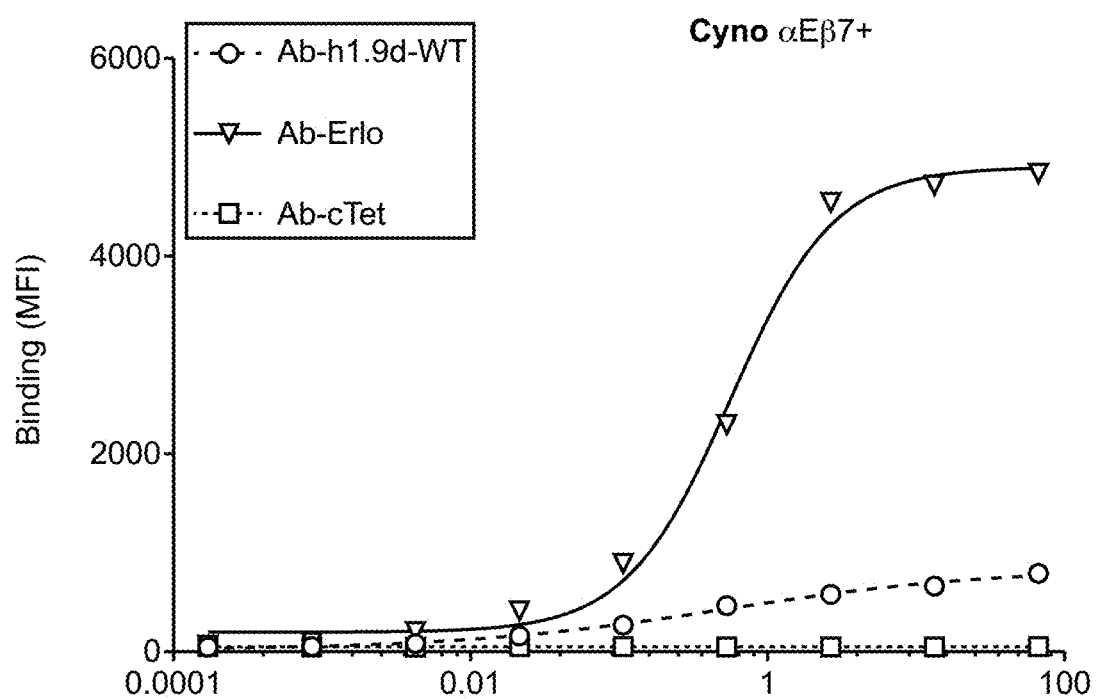

As shown in FIGS. 14A-14C Ab-h1.9d-WT bound specifically to human α4β7-expressing cells and did not bind to human α4β1 expressing cells, whereas an anti-α4 mAb, Ab-nata, did bind to both integrins. Ab-h1.9d-WT bound minimally to human αEβ7 expressing cells in comparison to the much stronger binding observed for an anti-β7 mAb, research grade Etrolizumab. Ab-h1.9d-WT displayed a similar binding specificity profile to cynomolgus integrins. These data demonstrated that Ab-h1.9d-WT has binding specificity for both human and cynomolgus α4β7.

Non-Specific HEK293 Cell Binding

Ab-h1.9d-WT was also evaluated for non-specific binding to human epithelial HEK293 cells. As demonstrated in FIG. 15, Ab-h1.9d-WT did not exhibit any non-specific binding to HEK293 cells at high concentration (100 μg/mL), comparable to a control antibody, while a positive control mAb displayed strong non-specific binding to these cells.

7.11. Example 11: Rabbit and Rodent Binding Cross-Reactivity of Ab-h1.9d-WT

7.11.1. Materials and Methods

The binding of Ab-h1.9d-WT to PBMCs isolated from rabbit, rat and mouse was evaluated via flow cytometry.
Rabbit and Rodent Cross-Reactivity Binding Assay Rabbit PBMCs were thawed, placed in RPMI1640/10% FBS media, washed 1× with FACS buffer (DPBS, w/o $Ca^{+2}/Mg^{+2}$, 1% BSA) and resuspended in FACS buffer containing 5% goat serum. Cells ($1 \times 10^5$ in 100 µL) were dispensed into a 96-well U-bottom plate and incubated on ice for 30 minutes. Plates were centrifuged to remove supernatant and 25 µL of titrated Ab-h1.9d-WT or isotype control plus 25 µL of 1:10 diluted CD4-FITC antibody (all Abs diluted in FACS buffer) were added to each well to reconstitute cell pellets. Well contents were mixed, followed by a 45 minute incubation on ice. In conjunction, appropriate staining controls were also prepared. Subsequently, cells were washed 2× with FACS buffer and 50 µL of a secondary antibody-PE was added to cell pellets at 1:2000 dilutions in FACS buffer containing 5% goat serum. Plate was further incubated on ice for 45 minutes. Cells were washed 2× with FACS buffer and resuspended in 200 µL of 0.5% PFA in PBS. The plate was read on FACS (Canto II, BD) and live cells were gated based on forward and side scatters. Percentage antibody-bound cells were determined by using FlowJo version 10 software, binding curves and binding $EC_{50}$ values were generated using GraphPad Prism 7.0 software.

Female C57BL/6N mice and female Lewis rats were received from Taconic Laboratories and Charles River Laboratories, respectively. PBMCs were isolated from pooled mouse and rat blood from the animals. Red blood cells were lysed using RBC lysis buffer (eBioscience). Cells were washed 1× in PBS and resuspended in FACS buffer (DPBS, w/o $Ca^{+2}/Mg^{+2}$, 1% BSA) containing 5% goat serum. Approximately $2.5 \times 10^5$ cells (100 µL) were added to a 96-well U-bottom plate then incubated on ice for 30 minutes. Appropriate fluorochrome-conjugated antibodies were added to mouse cells (CD3-APC, α4β7-PE or IgG2a-FITC control) or rat cells (CD3-APC, α4-FITC or IgG2a-PE control) at a 1:50 dilution in addition to Ab-h1.9d-WT or isotype control. Well contents were mixed thoroughly, and plate was incubated on ice for one hour. Final concentrations were 10 and 1 µg/mL for isotype controls and Ab-h1.9d-WT. Subsequently, cells were washed 2× with FACS buffer and 100 µL of secondary antibody-PE or secondary antibody-AF488 was added at 1:800 dilution to wells and plate was incubated on ice for 45 minutes. Following incubation, cells were washed 2× with FACS buffer, resuspended in 200 µL of 0.5% PFA in PBS. The plate was read on FACS (Canto II, BD) and live cells were gated based on forward and side scatters. Percentage CD3+ cells bound to test antibody or isotype control were determined by using FlowJo version 10 software and graphed using GraphPad Prism 7.0 software.

7.11.2. Results

As summarized in TABLE 28, Ab-h1.9d-WT displayed similar binding EC50 values for rabbit lymphocytes and CD4+ T cells in comparison to the human and cynomolgus counterparts, whereas Ab-h1.9d-WT did not show any measurable binding to rat or mouse PBMCs (lymphocytes and CD4+ T cells).

TABLE 28

Binding of Ab-h1.9d-WT to Rabbit and Rodent Blood Lymphocytes and CD4+ T Cells in Comparison to Human and Cynomolgus

| Species | $EC_{50}$ (pM) (Mean ± SD) | |
|---|---|---|
| | Lymphocytes | CD4+ T Cells |
| Human[a] | 130 ± 85 | 63 ± 38 |
| Cynomolgus[b] | 62 ± 45 | 30 ± 16 |
| Rabbit[a] | 89 ± 34 | 97 ± 11 |
| Rat[c] | No binding | No binding |
| Mouse[c] | No binding | No binding |

EC50 values determined using % of lymphocytes and CD4+ cells expressing α4β7
[a]Human/Rabbit PBMC = 3 donors
[b]Cynomolgus PBMC = 5 donors
[c]Rodent PBMC from pooled blood

7.12. Example 12: Ab-h1.9d-WT-Induced α4β7 Internalization

7.12.1. Materials and Methods

Ab-h1.9d-WT was investigated for its ability to induce internalization of cell surface α4β7 on human primary CD4+ and CD8+ naïve T cells from two PBMC donors.
Internalization Assay Ab-h1.9d-WT internalization was investigated and quantified using a similar FACS protocol used to determine cellular mechanisms of Etrolizumab (Lichnog et al., Front Pharmacol). Peripheral blood mononuclear cells (PBMCs) were isolated from two healthy blood donors (RBC, Donor KP58219 and KP58239) using Ficoll Paque (GE 17-1440-03) and SepMate tubes (StemCell 85450), resuspended in FBS (Gibco 10438-026) containing 5% DMSO and cryopreserved in liquid nitrogen. Frozen PBMCs were thawed, counted and reconstituted at $1 \times 10^6$ cells/mL in RPMI media+10% FBS and 100 µL of cells were plated at $1 \times 10^5$ cells per well. The plated cells were then incubated at 4° C. or placed in 37° C., 5% $CO_2$ incubator for 30 minutes to acclimate plate temperature. Human PBMCs were pre-incubated with 100 µL of 2× conc. unlabeled Ab-h1.9d-WT antibody at 1.25 µg/mL (final 0.625 µg/mL) for one hour at 4° C. Cells were centrifuged, washed and resuspended in 200 µL of RPMI+10% FBS and incubated at 4° C. or 37° C., 5% $CO_2$ for 18 hours. Following incubation, cells were washed 2× with FACS buffer (PBS+1% FBS), and then stained with CD4+ (Biolegend 317410), CD8+ (Biolegend 344710), and CD45RA (Biolegend 304130) with or without the AF647 labeled noncompeting anti-β7 antibody for 30 minutes. Cell fluorescence was acquired by flow cytometry (LSR-Fortessa). The data was analyzed using FlowJo 10 software and percentage internalization was calculated by 100×[Total cell surface α4β7 expression before internalization (MFI at 4° C.)—Remaining cell surface α4β7 expression after internalization (MFI at 37° C.)/Total cell surface α4β7 expression before internalization (MFI at 4° C.)].

7.12.2. Results

As shown in FIG. 16A, when evaluated 18 hours after Ab-h1.9d-WT bound to human PBMCs at 4° C. to minimize internalization, 73% of CD4+ naïve T cells (CD4+ CD45RA+) and 49% of CD8+ naïve T cells (CD8+ CD45RA+) from donor 1 remained β7-positive. However, after Ab-h1.9d-WT incubation under the same protocol but at 37° C. to promote internalization, only 17% of CD4+ naïve T cells and 7% of CD8+ naïve T cells were found to be β7-positive. These data indicate that significant internalization of surface α4β7 bound to Ab-h1.9d-WT occurred at 37° C. Similar results were observed with PBMCs from donor 2. Based on the quantification of α4β7 internalization at 37° C. (reduced surface α4β7 expression relative to the expression observed after treatment at 4° C.) in FIG. 16B, Ab-h1.9d-WT was able to induce α4β7 internalization by ~80% on both α4β7$^+$ naïve CD4+ and CD8+ T cells.

Ab-h1.9d-WT is more potent in inducing α4β7 internalization in comparison to Ab-Vedo.

7.13. Example 13: MAdCAM-1 Ligand Blockade by Ab-h1.9d-WT

7.13.1. Materials and Methods

MAdCAM-1 Ligand Blockade Assay

For FACS-based assay, HuT78 cells or human PBMCs were harvested, washed 1× with DPBS, adjusted to a density of 1.5×10$^6$ cells/mL and resuspended in FACS buffer (DPBS, w/o Ca$^{+2}$/Mg$^{+2}$, 1% BSA/1 mM MnCl$_2$). Cells at 1×10$^5$ (100 μL)/well were dispensed into a 96-well U-bottom plate and centrifuged to remove supernatant. Titrated Ab-h1.9d-WT or isotype control (50 μL) plus 50 μL mixture containing 0.3 μg/mL MAdCAM-1-mFc, 2 mM MnCl$_2$, and 1:50 diluted (30 μg/mL) Alexa488 conjugated detection Ab in FACS buffer were added to each well. The plate was incubated on ice for one hour then centrifuged. The plate was gently washed 1× with 200 μL FACS buffer and cells were reconstituted in same buffer. The plate was read by FACS (Canto II) and live cells were determined by forward and side scatter gating. Flow data (FCS 3.0 files) was analyzed using FlowJo Version 10 software, binding curves and inhibition IC$_{50}$ values were generated using GraphPad Prism 7.0 software.

For plate-based assay, 96-well flat-bottom plates (Greiner, Cat 655077) were coated with 100 μL of 20 μg/mL MAdCAM-1 hFc or isotype control (final concentration 2 μg/well) using coating buffer (PBS w/o Ca$^{+2}$/Mg$^{+2}$, 0.1% BSA) at 4° C. for overnight. Next day, plate(s) were washed 2× with 200 μL of wash buffer (PBS w/Ca$^{+2}$/Mg$^{+2}$, 0.1% BSA) then blocked at 37° C. for one hour using blocking buffer (PBS w/Ca$^{+2}$/Mg$^{+2}$, 1% BSA). During blocking incubation, dilutions of Ab-h1.9d-WT and isotype control were prepared and HuT78 cells harvested. A 2× initial concentration was prepared at 5 μg/mL and then serial 1:4.5 7-point dilutions (final concentrations ranging from 2.5 to 0.0003 μg/mL) were performed in duplicate or triplicate. The cells were counted, washed and resuspended at a 2×10$^6$ cells/mL in assay media (IMDM, 1% BSA) to which a final concentration of 2 mM MnCl$_2$ was added and 100,000 cells were dispensed to each well of 96-well plates. The diluted antibodies were then added to the cells and the mixture was incubated at 37° C., 5% CO$_2$ for 30 minutes. The blocking solution from MAdCAM-1 hFc coated plates was decanted and 100 μL/well of pre-incubated HuT78 cells and mAb mixture was distributed into each well of MAdCAM-1 hFc coated plates. Plate(s) were spun at 1,000 rpm for one minute and incubated at 37° C., 5% CO$_2$ for 30 minutes. Adhesion plates were decanted and washed gently 4× with 150 μL of wash buffer. Post-washing, 100 μL/well of a mixture (containing 50 μL of CellTiter-Glo reagent and 50 μL assay medium) was added to each well. Plate(s) were placed on orbital shaker for two minutes then incubated at RT for 10 minutes. Plate luminescence was read on a luminescence plate reader (Topcount, Perkin Elmer). Luminescence signal was plotted and IC$_{50}$ values were determined in GraphPad Prism 7.0 using 4-parameter curve fit analysis.

7.13.2. Results

Ab-h1.9d-WT was tested for its ability to block the binding of recombinant extracellular domain of MAdCAM-1 protein to α4β7-expressing HuT78 cells and human lymphocytes (PBMCs) using both plate-based and FACS-based assays.

IC$_{50}$ values of 50 pM and 25 pM were obtained by using FACS- and plate-based assays, respectively.

In addition, the blockade of MAdCAM-1 binding to human blood-derived lymphocytes by Ab-h1.9d-WT was observed at IC$_{50}$ of 223 pM (TABLE 29).

TABLE 29

| MAdCAM-1 Blockade Potency IC$_{50}$ of Ab-h1.9d-WT *IC$_{50}$ (pM) | | |
|---|---|---|
| FACS | | Luminescence |
| HuT78 | Human Lymphocytes | HuT78 |
| 50 ± 11 | 223 ± 86 | 25 ± 4 |

*Average ± SD; N = 3

These data demonstrated the strong inhibitory effect of Ab-h1.9d-WT on MAdCAM-1/α4β7 interaction.

7.14. Example 14: Ab-h1.9d-WT Blocks MAdCAM-1 Co-Stimulation on Human Primary CD4+ T Cells

7.14.1. Materials and Methods

Human PBMCs and CD4+ T Cell Isolation

Human peripheral blood mononuclear cells (PBMCs) were isolated from fresh blood collected from healthy donors. Human CD4+ T cells were then isolated from PBMCs using a CD4 negative selection kit (Stem Cell Technologies).

CD4+ T Cell Activation and Proliferation Assay 96-well flat bottom tissue culture plates were coated with 200 ng/well anti-CD3 antibody (Biolegend) in HBSS at 4° C. overnight. On the following day, the anti-CD3 coated plates were washed once with HBSS and incubated with 200 ng/well MAdCAM-1 (R&D systems) for 1 hour at 37° C. Following the incubation, the plates were washed once with 200 ul of HBSS and 50,000 CD4+ T cells were added to each well in the presence or absence of 1 μg/ml testing antibodies. After culturing the cells at 37° C., 5% CO2 for 96 hours, the cells were washed and stained with Live-Dead Aqua viability dye (Thermofisher) and subsequently stained with the cell activation markers anti-CD25 FITC (Clone MA0251 BD bioscience) and anti-Ki67 APC (Biolegend). Cells were analyzed on a flow cytometer and the data were analyzed with FlowJo software. Data from multiple donors were plotted and the statistical analysis was performed using GraphPad Prism. Significance was determined using one-way ANOVA coupled to Tukey's multiple comparisons test. **p<0.0001, p=0.001-0.01.

7.14.2. Results

Ab-h1.9d-WT Blocks MAdCAM-1 Co-Stimulation on Human Primary CD4+ T Cells

MAdCAM-1-mediated gut-homing of α4β7+CD4+ T cells plays a central role in HIV infection of GALT (gut-associated lymphoid tissues). In addition to this role, MAdCAM-1 has also been reported to deliver a co-stimulation signal to human primary CD4+ T cells and promote HIV replication (Nawaz et. al., Mucosal Immunology 2018). Given that HIV infection and replication require metabolic activation of these cells and Ab-h1.9d-WT can block MAdCAM-1 binding to human lymphocytes at IC50 value of 223 pM (TABLE 35), we evaluated whether Ab-h1.9d-WT is capable of blocking MAdCAM-1 co-stimulation signal on human primary CD4+ T cells, which would in turn inhibit the MAdCAM-1-mediated viral replication in these cells.

When human primary CD4+ T cells from one representative healthy donor were incubated with plate bound anti-CD3 alone for 96 hours, 22.6% of the cells were activated displaying Ki67+CD25+ phenotype (FIG. 17A). When the cells were incubated with the plate bound anti-CD3 and MAdCAM-1 together, 56.6% of the CD4+ T cells were activated. This indicates that MAdCAM-1 delivered a co-stimulation signal to CD4+ T cells mediated by interacting to the cell surface α4β7. Addition of Ab-h1.9d-WT to the cells during the 96-hour incubation reduced the cell activation to 20.8%, a level comparable to the anti-CD3 alone, while an isotype control Ab did not have any inhibitory effect on the cell activation. The data suggest that Ab-h1.9d-WT effectively and completely blocked the co-stimulation signal exerted by MAdCAM-1. The assay was repeated with the primary CD4 T cells from five additional individual donors and the data is summarized in FIG. 17B. Consistent with the data obtained from one representative donor in FIG. 17A, Ab-h1.9d-WT almost completely blocked MAdCAM-1/α4β7 mediated co-stimulation of CD4+ T cells while the isotype control Ab did not have any inhibitory effect.

7.15. Example 15: VCAM-1 Ligand Blockade Specificity of Ab-h1.9d-WT

7.15.1. Materials and Methods

The effect Ab-h1.9d-WT on the α4β7/VCAM-1 interaction in a VCAM-1 mediated cell adhesion assay was assessed.

VCAM-1 Ligand Blockade Assay

Plates (96-well flat-bottom, Greiner, Cat 655077) were coated on Day 1 with 100 μL of 20 μg/mL VCAM-1 hFc or isotype control (final concentration 2 μg/well) using coating buffer (PBS w/o $Ca^{+2}$/$Mg^{+2}$, 0.1% BSA) at 4° C. overnight. On Day 2, plate(s) were washed 3× with 200 μL of wash buffer (PBS w/$Ca^{+2}$/$Mg^{+2}$, 0.1% BSA) then blocked at 37° C. for 1 h or longer using blocking buffer (PBS w/$Ca^{+2}$/$Mg^{+2}$, 1% BSA). During blocking incubation, dilutions of Ab-h1.9d-WT, Ab-nata and isotype control were prepared and HuT78 cells were harvested. A 2× initial concentration of antibody was prepared at 4 μg/mL and then 1:4 fold serial dilutions in assay medium (IMDM, 1% BSA) were made. HuT78 cells were counted, washed and resuspended at a $2 \times 10^6$ cells/mL in assay medium to which a final concentration of 2 mM $MnCl_2$ was added and 100,000 cells were dispensed to each well of 96-well plates. The diluted antibodies were then added to the cells and the mixture was incubated at 37° C., 5% $CO_2$ for 30 minutes. The blocking solution from VCAM-1 hFc coated plates was decanted, and 100 μL of pre-incubated HuT78 cells and mAb mixture were distributed into each well of VCAM-1 hFc coated plates. Plate(s) were incubated at 37° C., 5% $CO_2$ for 30 minutes and then were washed gently 3× using washing buffer. Post-washing, 100 μL/well of a mixture (containing 50 μL of CellTiter-Glo reagent and 50 μL assay medium) was added to each well. Plate(s) were placed on orbital shaker for two minutes then incubated at RT for 10 minutes. Plate luminescence was read on luminescence plate reader (Topcount, Perkin Elmer). Luminescence signals were plotted to determine $IC_{50}$ values in GraphPad Prism 7.0 using 4-parameter curve fit analysis.

7.15.2. Results

In addition to α4β7 binding to MAdCAM-1 enabling gut homing of blood lymphocytes, α4β7 can also bind to VCAM-1 expressed on endothelial cells (TABLE 30).

TABLE 30

| | VCAM-1 Blockade Selectivity of Ab-h1.9d-WT | | | |
|---|---|---|---|---|
| mAb | Experiment 1 | Experiment 2 | Experiment 3 | Average (N = 3) $IC_{50}$ (pM) ± SD |
| | IC50 (pM) | | | |
| Ab-h1.9d-WT | no inhibition | no inhibition | no inhibition | no inhibition |
| Ab-nata | 38 | 54 | 77 | 56 ± 20 |

Natalizumab, Ab-nata an anti-α4 mAb, capable of blocking α4β7 and α4β1 binding to VCAM-1 caused progressive multifocal leukoencephalopathy (PML) due to its blockade of trafficking of circulating lymphocytes to the brain. Therefore, assessment of the effect Ab-h1.9d-WT on the α4β7/VCAM-1 interaction in a VCAM-1 mediated cell adhesion assay was an essential safety parameter to investigate using Ab-nata as a positive control. As expected, Ab-nata blocked VCAM-1-mediated HuT78 cell adhesion with mean $IC_{50}$ value of 56 pM. In contrast, Ab-h1.9d-WT showed no detectable blockade of HuT78 cell adhesion mediated by VCAM-1 (FIG. 18).

Despite Ab-h1.9d-WT selectively blocking α4β7/MAdCAM-1 interaction with high potency, it shows no inhibition of α4β7/VCAM-1 interaction.

7.16. Example 16: Ab-h1.9d-WT Binding Affinity to Human and Cynomolgus Monkey FcγRI, FcγRIIa, FcγRIIb, FcγRIIIa and FcRn

7.16.1. Materials and Methods

Ab-h1.9d-WT was evaluated by BIAcore for its binding affinity to a panel of recombinant human and cynomolgus monkey FcγR extracellular domain (ECD) proteins in comparison to antibody IgG1 control, Trastuzumab.

Ab-h1.9d-WT binding to human FcγRs was also evaluated via flow cytometry by using CHO-K1 cells engineered to express various cell surface human FcγRs.

Binding of Ab-h1.9d-WT to human and cynomolgus FcRn was evaluated by BIAcore at pH 6.0 and pH 7.4 using recombinant human and cynomolgus FcRn ECD protein (TABLE 31).

TABLE 31

Binding Affinity of Ab-h1.9d-WT to Human and Cynomolgus FcRn via BIAcore

| Antibody | Human FcRn $K_D$ (M) (Mean ± SD) | | Cynomolgus FcRn $K_D$ (M) (Mean ± SD) | |
|---|---|---|---|---|
| | pH 6.0 | pH 7.4 | pH 6.0 | pH 7.4 |
| Ab-h1.9d-WT | $3.3 \times 10^{-6} \pm 0.2 \times 10^{-6}$ | No significant binding | $2.2 \times 10^{-6} \pm 0.3 \times 10^{-6}$ | No significant binding |
| Trastuzumab | $3.2 \times 10^{-6} \pm 0.1 \times 10^{-6}$ | No significant binding | $2.2 \times 10^{-6} \pm 0.4 \times 10^{-6}$ | No significant binding |

N = 3

Human and Cynomolgus Monkey FcγR1, FcγRIIa, FcγRIIb, and FcγRIIIa Surface Plasmon Resonance (SPR) Binding Assay Binding kinetics of Ab-h1.9d-WT for His tagged human FcγRs were determined by SPR measurements made on Biacore T200 instrument (GE Healthcare) at 25° C. using anti-His capture. Approximately 10000 RU of mouse anti-His antibody (R&D) diluted to 25 μg/mL in 10 mM sodium acetate (pH 4.5) was immobilized across a CM5 biosensor chip using a standard amine coupling kit according to manufacturer's instructions. Unreacted moieties on the biosensor surface were blocked with 1M ethanolamine. Activated and deactivated surface on flow cell 1 were used as a reference. Chip preparation and binding kinetic measurements were made in assay running buffer, HBS-EP+(10 mM Hepes, pH 7.4, 150 mM NaCl, 3 mM EDTA, 0.05% Tween 20). Human and cynomolgus FcγRs were then captured on flow cells 2 to achieve capture level of 250 to 500 RU. Ab-h1.9d-WT samples were injected over all flow cells at a flow rate of 50 μL/min for one to five minutes (one minute for hu and cynomolgus FcγRIIb and FcγRIIa, two minutes for hu FcγRIIIa and five minutes for hu and cynomolgus FcγRI & cynomolgus FcγRIII). Analyte concentrations ranged from 0.78 to 200 nM for hu and cynomolgus FcγRI cynomolgus FcγRIII, 46.9 to 12000 nM for hu and cynomolgus FcγRII and 7.8 to 4000 nM for FcγRIII (2-fold serial dilution). A buffer only injection was included for double referencing. Bound FcγRs dissociation was monitored for one to five minutes (one minute for FcγRIIb, FcγRIIa, three minutes for FcγRIIIa and five minutes for FcγRI). The chip surface was regenerated with injected 100 mM HCl at a flow rate of 100 μL/min for two seconds across all eight channels. Three experiments using the same CM5 chip were run for each sample. The results of these three experiments were averaged.

Human FcγR1, FcγRIIa, FcγRIIb, FcγRIIIa Cell Binding Assay

CHO-K1 expressing hFcγR cells were grown in 150 cm² culture flasks and loaded with a specific amount of fluorophore, CellTrace CFSE™ and CellTrace Violet™ (Molecular Probes) according to manufacturer instructions to establish a unique fluorescence footprint (barcoding method) for each line. Lines were mixed and incubated at 4° C. for one hour with monomeric Ab-h1.9d-WT at different concentrations (0, 0.01, 0.1, 1, 10, 50, 100, and 250 μg/mL) in RPMI1640/2 mM L-glutamine/10% Ultra Low IgG heat inactivated FBS (binding media). Following incubation, cells were washed 2× in PBS, pH7.4 (w/o $Ca^{+2}/Mg^{+2}$) and incubated for 15 minutes at 4° C. with secondary antibody (F(ab')$_2$ goat anti-human IgG (H+L) coupled to AF647 in binding media to detect cell bound Ab-h1.9d-WT. Following incubation, cells were further washed 2× with PBS, pH7.4 (w/o $Ca^{+2}/Mg^{+2}$). Cell surface fluorescence was detected and recorded using a flow cytometry analyzer (LSR-Fortessa). The recorded fluorescence data were analyzed using FlowJo software Version 10 (Tristar) and Ab-h1.9d-WT binding to CHO-K1 hFcγR cells was reported as the geometric mean of fluorescence of AF647 (binding curves of gMFI as a function of Ab-h1.9d-WT concentration were generated).

Human and Cynomolgus Monkey FcRn Surface Plasmon Binding Assay

For FcRn binding analysis, Ab-h1.9d-WT was directly immobilized on a CM5 chip amine coupling according to manufacturer's protocol to a density of 750 RU. Human and cynomolgus FcRn recombinant proteins were injected across all flow cells at a flow rate of 50 μL/min for one minute at concentrations ranging from 5.5 to 12000 nM (3-fold serial dilution), followed by a one minute dissociation. The surface was regenerated with an injection of HBS-EP+pH 7.4 for 15 seconds. Samples were prepared and run in two running buffers, MES EP+pH 6.0 and HBS-EP+pH 7.4. Three experiments with the use of the different CM5 chips were run for each sample (each in duplicate). The results of these three experiments were averaged. Data from human FcγR1, FcγRIIIa (F158), FcγRIIIa (V158) and cynomolgus FcγRI, FcγRIII binding to all samples were fitted to a 1:1 global kinetics model with fixed $R_{max}$. Data from human, FcγRIIb, FcγRIIa (H131), FcγRIIa (R131), cynomolgus FcγRIIa, FcγRIIb and FcRn binding to all samples were fitted to a steady state affinity model. Biacore T200 Evaluation Software Version 2.0 was used to fit FcγR and FcRn data.

7.16.2. Results

Human and Cynomolgus Monkey FcγR1, FcγRIIa, FcγRIIb, and FcγRIIIa Binding

The binding kinetic parameters are summarized in TABLE 32 (for human) and TABLE 33 (for cynomolgus).

TABLE 32

Binding Affinity of Ab-h1.9d-WT to Human FcγRs via BIAcore

Captured FcγRs $K_D$(M) (Mean ± SD)

| Antibody | hFcγRI | hFcγRIIa (H131) | hFcγRIIa (R131) | hFcγRIIb | hFcγRIIIa (F158) | hFcγRIIIa (V158) |
|---|---|---|---|---|---|---|
| Ab-h1.9d-WT | $1.6 \times 10^{-8} \pm 0.2 \times 10^{-8}$ | $5.6 \times 10^{-6} \pm 0.8 \times 10^{-6}$ | binds but too weak to determine | binds but too weak to determine | $4.6 \times 10^{-6} \pm 2.1 \times 10^{-6}$ | $4.8 \times 10^{-7} \pm 3.1 \times 10^{-7}$ |
| Trastuzumab | $1.5 \times 10^{-8} \pm 0.3 \times 10^{-8}$ | $6.1 \times 10^{-6} \pm 0.3 \times 10^{-6}$ | $8.9 \times 10^{-6} \pm 0.3 \times 10^{-6}$ | binds but too weak to determine | $9.5 \times 10^{-7} \pm 0.3 \times 10^{-7}$ | $9.4 \times 10^{-8} \pm 0.1 \times 10^{-8}$ |

N = 3

Ab-h1.9d-WT and Trastuzumab had similar measurable binding affinities to both hFcγRI and hFcγRII (H131), weaker binding to hFcγRII (R131) and hFcγRIIb receptors. Ab-h1.9d-WT and Trastuzumab had measurable binding affinities to hFcγRIIIa (F158/V158) with higher affinity for the V158 polymorphic variant as expected.

TABLE 33

Binding Affinity of Ab-h1.9d-WT to Cynomolgus FcγRs via BIAcore

Captured FcγRs
$K_D$ (M) (Mean ± SD)

| Antibody | Cynomolgus FcγRI | Cynomolgus FcγRIIa | Cynomolgus FcγRIIb | Cynomolgus FcγRIII |
|---|---|---|---|---|
| Ab-h1.9d-WT | $1.2 \times 10^{-8} \pm 0.1 \times 10^{-8}$ | binds but too weak to determine | binds but too weak to determine | $2.8 \times 10^{-7} \pm 4.6 \times 10^{-7}$ |
| Trastuzumab | $1.3 \times 10^{-8} \pm 0.2 \times 10^{-8}$ | binds but too weak to determine | binds but too weak to determine | $8.0 \times 10^{-8} \pm 4.6 \times 10^{-8}$ |

N = 3

While both Ab-h1.9d-WT and trastuzumab exhibited binding to both cynomolgus FcγRI and cynomolgus FcγRIII, no measurable binding parameters could be determined for cynomolgus FcγRIIa and cynomolgus FcγRII receptors likely due to their weak binding to these receptors.

Human FcγR1, FcγRIIa, FcγRIIb, FcγRIIIa Cell Binding Assay

Ab-h1.9d-WT displayed the highest binding to human FcγRI and FcγRIIIa (V176) polymorphic variant, but relatively low binding to other human FcγRs [FcγRIIa, FcγRIIb, FcγRIIc, FcγRIIIa (F176) and FcγRIIIb] (FIGS. 19A-19B).

Human and Cynomolgus Monkey FcRn Surface Plasmon Binding Assay

Ab-h1.9d-WT exhibited measurable binding to human and cynomolgus FcRn under acidic conditions (pH 6.0), but no measurable binding at neutral pH (pH 7.4) (TABLE 34). FcRn binding properties were comparable to control (Trastuzumab).

TABLE 34

Binding Affinity of Ab-h1.9d-WT to Human and Cynomolgus FcRn via BIAcore

| | Human FcRn $K_D$ (M) (Mean ± SD) | | Cynomolgus FcRn $K_D$ (M) (Mean ± SD) | |
|---|---|---|---|---|
| Antibody | pH 6.0 | pH 7.4 | pH 6.0 | pH 7.4 |
| Ab-h1.9d-WT | $3.3 \times 10^{-6} \pm 0.2 \times 10^{-6}$ | No significant binding | $2.2 \times 10^{-6} \pm 0.3 \times 10^{-6}$ | No significant binding |
| Trastuzumab | $3.2 \times 10^{-6} \pm 0.1 \times 10^{-6}$ | No significant binding | $2.2 \times 10^{-6} \pm 0.4 \times 10^{-6}$ | No significant binding |

N = 3

7.17. Example 17: Ab-h1.9d-WT In Vitro ADCC, ADCP and CDC Activity

7.17.1. Materials and Methods

Ab-h1.9d-WT was evaluated for in vitro ADCC and ADCP activities using native α4β7/CD20-expressing RPMI8866 cells as target cells and the reporter Jurkat cells expressing either hFcγRIIIa (V158) or hFcγRIIa (H131) as effector cells. This Jurkat cell line had an NFAT response element that drives the expression of firefly luciferase as reporter. Ab-Ritu, an anti-CD20 mAb was used as a positive control in these assays.

Furthermore, Ab-h1.9d-WT was evaluated in a cell cytotoxicity-based ADCC assay using α4β7/CD52 expressing HuT78 cells as targets, human primary NK cells as effectors and Campath (anti-CD52) as a positive control antibody.

ADCC Reporter Assay

Target α4β7 expressing RPMI8866 cells were grown and maintained in culture media (RPMI1640, 2 mM L-glutamine and 10% FBS). Log phase cells were harvested, counted, washed and resuspended at a $6\times10^5$ cells/mL stock in assay medium (RPMI1640 containing low IgG serum) and placed at 37° C., 5% $CO_2$ until ready for use. Ab-h1.9d-WT and control mAbs were prepared at a 3× initial concentration of 30 µg/mL then serially (2 pt.) diluted at 1:100 in Costar 3956 dilution plates. Antibodies (25 µL) were mixed with an equal volume of target RPMI8866 cells (25 µL) in duplicate according to plate layout(s). Effector Jurkat cells (stably expressing the human FcγRIIIa V158 variant and an NFAT response element driving expression of firefly luciferase from Promega™) were thawed rapidly and adjusted to $3\times10^6$ cells/mL in assay media. Jurkat effectors (25 µL) were then added to the 96-well assay plates containing RPMI8866 targets and antibody. Control wells included media alone, Effector (E) and Target (T) alone, E+T, E+mAb (30 µg/mL) or T+mAb (30 µg/mL). All wells were adjusted to 75 µL per well according to plate layout(s). The final cell numbers were 75,000 Jurkat effector cells/well and 15,000 RPMI8866 target cells/well corresponding to an E:T ratio of 5:1. The final antibody concentrations per well were 67 nM (10 µg/mL), 0.67 nM (0.1 µg/mL) and 0.0067 nM (0.001 µg/mL). Plates were incubated at 37° C., 5% $CO_2$ for six hours during which Bio-Glo™ buffer and substrate (Cat 7110) was equilibrated to RT prior to use. At the end of the incubation, Bio-Glo substrate was reconstituted with buffer to form enzyme/substrate solution (Bio-Glo reagent). An equal volume of 75 µL/well Bio-Glo was added to all wells. Plates were then incubated at RT for 10 minutes. Plate luminescence was read on a luminescence plate reader (Topcount, Perkin Elmer). Luminescence signal was plotted as RLU using GraphPad Prism 7.0 software.

ADCP Reporter Assay

Target α4β7 expressing RPMI8866 cells were grown and maintained in culture media (RPMI1640, 2 mM L-glutamine and 10% FBS). Log phase cells were harvested, counted, washed and resuspended at a $2\times10^5$ cells/mL stock in assay medium (RPMI1640 containing low IgG serum) and placed at 37° C., 5% $CO_2$ until ready for use. Ab-h1.9d-WT and control mAbs, were prepared at a 3× initial concentration of 30 µg/mL then serially (2 pt.) diluted at 1:100 in Costar 3956 dilution plates. Antibodies (25 µL) were mixed with an equal volume of target cells (25 µL) in duplicate according to plate layout(s). Effector Jurkat cells (stably expressing the human FcγRIIa H131 variant and an NFAT response element driving expression of firefly luciferase from Promega™) were thawed rapidly and adjusted to $1\times10^6$ cells/mL in assay media. Jurkat effectors (25 µL) were then added to the 96-well assay plates containing RPMI8866 targets and antibody. Control wells included media alone, Effector (E) and Target (T) alone, E+T, E+mAb (30 µg/mL) or T+mAb (30 µg/mL). All wells were adjusted to 75 µL per well according to plate layout(s). The final cell numbers were 25,000 Jurkat effector cells/well and 5,000 target cells/well corresponding to an E:T ratio of 5:1. The final antibody concentrations per well were 67 nM (10 µg/mL), 0.67 nM (0.1 µg/mL) and 0.0067 nM (0.001 µg/mL). Plates were incubated at 37° C., 5% $CO_2$ for six hours during which Bio-Glo™ buffer and substrate (Cat 7110) was equilibrated to RT prior to use. At the end of the incubation, Bio-Glo substrate was reconstituted with buffer to form enzyme/substrate solution (Bio-Glo reagent). An equal volume of 75 µL/well Bio-Glo was added to all wells. Plates were then incubated at RT for 10 minutes. Plate luminescence was read on a luminescence plate reader (Topcount, Perkin Elmer). Luminescence signal was plotted as RLU using GraphPad Prism 7.0 software.

CDC Assay

RPMI8866 cells were grown and maintained in culture media (RPMI1640, 2 mM L-glutamine and 10% FBS). Log phase cells were harvested, counted, washed and resuspended in assay medium (RPMI1640 minus phenol red, Cat 11835-030) at a $4\times10^6$ cells/mL stock and placed at 37° C., 5% $CO_2$ until ready for use. Ab-h1.9d-WT and control mAbs were prepared at a 3× initial concentration of 45 µg/mL and 0.45 µg/mL in Costar 3956 dilution plates. Human donor serum (HMN19169 and HMN19170) was thawed using cold running water and immediately placed on ice. Antibodies, controls (25 µL) and media were added to assay plates (Costar 3599). Donor serum (25 µL each), the target cells (25 µL) and diluted mAbs (25 µL) were mixed at the final volume of 75 4 per well containing 33% serum complement, $1\times10^5$ cells and 15 µg/mL mAb. Plate(s) were then incubated at 37° C., 5% $CO_2$ for two hours. After the incubation cell permeable dye (Sigma; Resazurin Sodium Salt) at a 5× stock solution of 1.5 mg/mL was diluted 1:5 in DPBS and 25 µL of dye was added to each well. Plates were incubated for additional 16 hours and then absorbance (545/600) was read using Clariostar plate reader. Percentage target-specific cell lysis was calculated in Excel using formula: 100–100×[(absorbance with mAb incubation)/(control absorbance)]; and the results were plotted using GraphPad Prism 7.0 software.

ADCC Cytotoxicity Assay

Target α4β7 expressing HuT78 cells were harvested, washed 2× with PBS (w/o $Ca^{+2}/Mg^{+2}$, 1% BSA) and resuspended in PBS at $1\times10^7$ cells/mL then labeled with CFSE at RT for eight minutes at a final concentration of 2 µM. After incubation, FBS was added at a 10% final concentration to quench labeling. Cells were washed 2× with RPMI+10% FBS media and then CFSE labeled HuT78 cells were incubated with 100 µL of a 2× conc. of Ab-h1.9d-WT or control antibodies at 10 µg/mL for 30 minutes at 37° C., 5% $CO_2$ in a 96-well V-bottom plate. Subsequently, 100 µL of $2.5\times10^5$NK (FcγRIIIa V158+) effector cells (preincubated with IL-2 at 200 U/mL) were added to target cells at a 5:1 ratio. Well contents were mixed thoroughly, followed by a five hour incubation at 37° C. in $CO_2$ incubator. NK and HuT78 cell mixtures were washed 2× with PBS and resuspended at $1\times10^6$ cells/mL with azide-free and protein-free PBS containing 1 µL of FVD dye/mL and incubated at RT for 20 minutes. Cells were washed 2× with FACS buffer, resuspended in 200 µL of 0.5% PFA in PBS and plate was read on FACS (Canto II, BD). Flow data (FCS 3.0 files) was analyzed by using FlowJo Version 10 software. All HuT78 target cells (live and dead) were gated to determine % dead targets within the total target cell population. The formula used for % ADCC calculation was % ADCC=100×[% dead targets in (E+T+Ab) mix−% dead targets in (E+T) mix]/[100−% dead targets in (E+T) mix]. Percentage ADCC was graphed using GraphPad Prism 7.0 software.

7.17.2. Results

ADCC Reporter Activity, ADCP Reporter Activity, and CDC

As expected, Ab-Ritu demonstrated strong concentration-dependent in vitro ADCC and ADCP activity; however, Ab-h1.9d-WT and isotype control did not show any of these activities at three concentrations (10, 0.1, 0.001 µg/mL) tested (FIGS. 20A and 20B). Only minimal signals were detected for three negative control assay conditions namely targets and effectors alone, targets plus antibody, and effectors plus antibody (data not shown). Ab-Ritu also demonstrated strong in vitro CDC activity on RPMI8866 cells at 0.15 and 15 µg/mL (100 nM) whereas Ab-h1.9d-WT and isotype control showed no CDC signal at corresponding concentrations using two human serum donors (FIG. 21).

ADCC Cytotoxicity

In this in vitro assay, Campath (Ab-Alem) displayed strong cell cytotoxicity against the target cells. In contrast, Ab-h1.9d-WT did not induce any in vitro cell cytotoxicity at 10 µg/mL (67 nM) concentration when the assay was performed using NK effector cells isolated from two different donors with FcγRIIIa V158 genotype (FIG. 22). Thus, although Ab-h1.9d-WT binds to human FcγRs as shown above (Example 12), it does not induce undesired Fc-mediated ADCC, ADCP and CDC activities against uninfected α4β7+ cells in vitro.

7.18. Example 18: Homology Modeling of Ab-h1.9d-WT Binding Site on the Target

7.18.1. Materials and Methods

The binding mode of Ab-h1.9d-WT to α4β7 was explored by homology modeling. The crystal structure of recombinant human α4β7 extracellular domain protein in complex with another anti-α4β7 antibody, vedolizumab, has been published (Yu et al., J Cell Biol 2012). Based on that data and the unique sequence of the Fab region of Ab-h1.9d-WT, modeling of the binding modes of the candidate antibody in comparison to benchmark antibodies vedolizumab and AMG181 was undertaken.

7.18.2. Results

In agreement with the in vitro characterization data, Ab-h1.9 which is a humanized variant of hybridoma Ab-m1 and the parent of Ab-h1.9d-WT, and the two benchmark mAbs bind to α4β7 primarily through interactions with β7 subunit but also interacting, albeit slightly, with the α4 subunit. This model explains their lack of binding to α4β1 and very low binding to αEβ7. Interestingly, the model suggests a subtle difference between Ab-h1.9 and the two benchmark mAbs in that Ab-h1.9 binds slightly more residues on the α4 subunit. The overlapping epitopes evident in the model predicts that Ab-h1.9 and vedolizumab should compete for binding to their target. Indeed, in a FACS-based binding competition study, Ab-m1 was able to compete with Ab-Vedo binding to α4β7+ cells, indicating they bind to a similar binding epitope (TABLE 13).

7.19. Discussion

The expression levels of α4β7 on peripheral human CD4+ and CD8+ T cell subsets from HIV+ and HIV− individuals are comparable, suggesting that the α4β7 expression in CD4+ T cells from HIV+ individuals could support the incorporation of α4β7 into the budding HIV virions.

Ab-h1.9d-WT is a potent anti-α4β7 antibody that can bind to α4β7 on the envelope of virions of all laboratory grown HIV strains and HIV patients' samples tested. The immune complexes formed by Ab-h1.9d-WT and HIV virions could bind to different FcγRs through its Fc domain, a step that could enable it to be taken up by APCs by phagocytosis to induce the proposed "vaccination effect" for HIV control.

Although Ab-h1.9d-WT binds HIV virions, it does not neutralize HIV infection, which is consistent with the notion that α4β7 is not a viral receptor on host cells. By targeting α4β7 integrin, a host protein, on the HIV viral envelope, Ab-h1.9d-WT may exhibit a higher barrier to resistance compared to other antibodies targeting the HIV virally encoded gp120/41 glycoprotein in the viral envelope such as HIV broadly neutralizing antibodies.

Ab-h1.9d-WT can disrupt the interaction between α4β7 and its ligands such as MadCAM-1 or HIV gp120 through an Fab-dependent mechanism, inhibiting the CD4 T cell co-stimulation mediated by MadCAM-1 and gp120, and potentially inhibiting HIV replication in these stimulated cells.

Ab-h1.9d-WT can potentially inhibit cell-to-cell HIV viral transmission by an Fab-mediated mechanism through its ability to disrupt the interaction between α4β7 and HIV gp120.

When compared with Ab-h1.9d-WT, Ab-Vedo demonstrated lower activity in capturing HIV virions and disruption of the interaction between α4β7 and HIV gp120. Furthermore, although Ab-Vedo was capable of binding HIV virions to form immune complexes, these immune complexes bound to FcγRs with a much lower affinity than complexes formed by Ab-h1.9d-WT due to the engineered mutations in Ab-Vedo Fc domain to reduce Fc functions.

Vedolizumab demonstrated modest efficacy in two clinical studies for HIV studies. This efficacy can be attributable to Fab-dependent (e.g., antibody binding to α4β7 disrupting its interactions with its ligands such as MAdCAM-1and HIV gp120, thus inhibiting the CD4 T cell co-stimulation and the HIV replication in these stimulated cells, and cell-to-cell viral transmission), but not Fc-dependent mechanism of actions. The reduced binding affinity of vedolizumab to FcγRs renders it deficient in mediating Fc-dependent mechanisms. In contrast, Ab-h1.9d-WT, which has intact Fc functionality, may be positively differentiated from vedolizumab for its ability to induce sustained HIV viral suppression through its Fc-dependent mechanisms of action. The binding of the immune complexes formed by HIV virions and anti-α4β7 antibodies (with intact Fc domain) to FcγRs on APCs is required to induce new and durable HIV-specific immune responses (vaccination effect). Indeed, Ab-h1.9d-WT can mediate the uptake of α4β7-coated beads or α4β7-expressing GFP+VLPs (viral like particles) in an α4β7- and Fc-dependent manner in THP-1 cells. In summary, Ab-h1.9d-WT demonstrates activity in several proposed mechanisms of action for HIV control, including those that are Fc-dependent or Fab-dependent. Therefore, Ab-h1.9d-

WT is predicted to be a more potent agent than vedolizumab for sustained reduction of HIV viral load due to its higher affinity to α4β7 and its intact Fc functionality to induce "vaccination effect".

Key attributes of Ab-h1.9d-WT from a comprehensive in vitro characterization are summarized in TABLE 35.

TABLE 35

Ab-h1.9d-WT In Vitro Characterization Summary

| Binding EC$_{50}$ (pM) | |
|---|---|
| HuT78 T cells | 26 |
| Human/Cynomolgus lymphocytes | 130/62 |
| Human/Cynomolgus CD4+ memory T cells | 20/10 |
| Human/Cynomolgus CD8+ memory T cells | 52/36 |
| MAdCAM-1 Blockade Potency IC$_{50}$ (pM) | |
| HuT78 T cells | 50 |
| Human lymphocytes | 223 |
| Binding Specificity | |
| α4β7 | Yes |
| α4β1 | No |
| Non-specific Binding | |
| HEK293 | No |
| Human and Cynomolgus FcγR Binding | |
| Expected WT IgG1 binding | |
| Human and Cynomolgus FcRn Binding | |
| Expected binding at pH 6.0, no binding at pH 7.4 | |
| In Vitro Fc Mediated Effector Activities | |
| ADCC | No |
| ADCC | No |
| CDC | No |

Ab-h1.9d-WT is an antagonistic anti-α4β7 human IgG1/k monoclonal antibody that binds to α4β7 but not to α4β1 and minimally to αEβ7. Ab-h1.9d-WT binds strongly to both human and cynomolgus monkey CD4+ and CD8+ T subsets, demonstrating excellent cynomolgus binding cross-reactivity. However, Ab-h1.9d-WT does not bind to rodent PBMCs. Ab-h1.9d-WT selectively blocks α4β7/MAdCAM-1 interaction with high potency without inhibiting α4β7/VCAM-1 interaction. Ab-h1.9d-WT is capable of blocking MAdCAM-1-mediated co-stimulation of human primary CD4+ T cells. As expected for a human IgG1, Ab-h1.9d-WT binds to human FcγRs (a necessary prerequisite for Fc-mediated "vaccination effect" in vivo) without triggering ADCC, ADCP and CDC activities against uninfected α4β7+ cells in vitro. Lack of in vitro Fc effector activities by Ab-h1.9d-WT may be partly explained by the reduced cell surface α4β7 expression due to antibody-induced target internalization. Additionally, Ab-h1.9d-WT can mediate the uptake of α4β7-coated beads or α4β7-expressing VLPs (viral like particles) in an α4β7-dependent and Fc-dependent manner in THP-1 cells. Ab-h1.9d-WT exhibits the intended in vitro pharmacological properties necessary for clinical candidacy.

As provided in the disclosure, Ab-h1.9d-WT is a potent α4β7-selective antagonist that is differentiated and improved from vedolizumab. The key attributes of Ab-h1.9d-WT in comparison to Ab-Vedo are shown in TABLES 36-40 and summarized in Table 41.

TABLE 36

Ab-h1.9d-WT binding EC$_{50}$ to human and cynomolgus monkey blood derived CD4+ and CD8+ T subsets in comparison to Ab-Vedo

| | | CD4+ Binding EC50 pM* | | | CD8+ Binding EC50 pM* | | |
|---|---|---|---|---|---|---|---|
| | | CD4+ total | CD4+ naïve | CD4+ memory | CD8+ total | CD8+ naïve | CD8+ memory |
| Ab-h1.9d-WT | Human | 63 ± 38 | 84 ± 32 | 20 ± 12 | 165 ± 121 | 144 ± 120 | 52 ± 51 |
| | Cyno | 30 ± 16 | 45 ± 27 | 10 ± 12 | 35 ± 25 | 42 ± 26 | 36 ± 30 |
| Ab-Vedo | Human | 381 ± 61 | 381 ± 101 | 270 ± 209 | 658 ± 438 | 727 ± 725 | 258 ± 203 |
| | Cyno | 202 ± 149 | 228 ± 229 | 148 ± 229 | 199 ± 101 | 256 ± 189 | 204 ± 125 |

TABLE 37

Ab-h1.9d-WT binding EC$_{50}$ to human blood derived CD4+ and CD8+ T subsets in comparison to Ab-Vedo

| | | CD4+ Binding EC50 pM* | | | CD8+ Binding EC50 pM* | | |
|---|---|---|---|---|---|---|---|
| | | CD4+ total | CD4+ naïve | CD4+ memory | CD8+ total | CD8+ naïve | CD8+ memory |
| Ab-h1.9d-WT | Human | 63 ± 38 | 84 ± 32 | 20 ± 12 | 165 ± 121 | 144 ± 120 | 52 ± 51 |
| Ab-Vedo | Human | 381 ± 61 | 381 ± 101 | 270 ± 209 | 658 ± 438 | 727 ± 725 | 258 ± 203 |

Human PBMC = 3 donors

TABLE 38

Ab-h1.9d-WT binding EC$_{50}$ to cynomolgus monkey blood derived CD4+ and CD8+ T subsets in comparison to Ab-Vedo

|  |  | CD4+ Binding EC50 pM* | | | CD8+ Binding EC50 pM* | | |
| --- | --- | --- | --- | --- | --- | --- | --- |
|  |  | CD4+ total | CD4+ naïve | CD4+ memory | CD8+ total | CD8+ naïve | CD8+ memory |
| Ab-h1.9d-WT | Cyno | 30 ± 16 | 45 ± 27 | 10 ± 12 | 35 ± 25 | 42 ± 26 | 36 ± 30 |
| Ab-Vedo | Cyno | 202 ± 149 | 228 ± 229 | 148 ± 229 | 199 ± 101 | 256 ± 189 | 204 ± 125 |

Cynomolgus PBMC = 5 donors
CD4+ naïve = CD4+CD45RA+CCR7+ cells,
CD4+ memory = CD4+CD45RA–cells
CD8+ naïve = CD8+CD45RA+CCR7+ cells,
CD8+ memory = CD8+CD45RA–cells TABLE 39—Binding Affinity of Ab-h1.9d-WT to Human FcγRs in comparison to Ab-Vedo via BIAcore.

TABLE 39

Binding Affinity of Ab-h1.9d-WT to Human FcγRs in comparison to Ab-Vedo via BIAcore

|  | FcγRI | FcγRIIb | FcγRIIa 131R | FcγRIIa 131H | FcγRIIIa158F | FcγRIIIa158V |
| --- | --- | --- | --- | --- | --- | --- |
| Ab-h1.9d-WT | 7.0E−09 | 1.2E−05 | 5.2E−06 | 4.0E−06 | 3.1E−06 | 1.0E−07 |
| Ab-Vedo | | | No significant binding | | | |

N = 1

TABLE 40—Binding Affinity of Ab-h1.9d-WT to cynomolgus monkey FcγRs in comparison to Ab-Vedo via BIAcore.

TABLE 40

Binding Affinity of Ab-h1.9d-WT to cynomolgus monkey FcγRs in comparison to Ab-Vedo via BIAcore

|  | Cyno FcγRI | Cyno FcγRIIa | Cyno FcγRIIb | Cyno FcγRIII |
| --- | --- | --- | --- | --- |
| Ab-h1.9d-WT | 1.4E−09 | 8.2E−06 | 7.1E−06 | 1.6E−07 |
| Ab-Vedo | | Binds but too weak to measure | | |

N = 1

TABLE 41—Key attributes of Ab-h1.9d-WT in comparison to Ab-Vedo.

TABLE 41

Key attributes of Ab-h1.9d-WT in comparison to Ab-Vedo

|  | Ab-h1.9d-WT | Ab-Vedo |
| --- | --- | --- |
| CDR sequences | Unique | |
| [1]Binding EC50 to HuT78 cells (Flow cytometry) | 199 pM | 911 pM |
| [2]Binding EC50 to human lymphocytes | 130 ± 85 pM | 502 ± 212 pM |
| [2]Binding EC50 to human CD4+ Tm cells | 20 ± 12 pM | 270 ± 209 pM |
| [2]Binding EC50 to cyno CD4+ Tm cells | 10 ± 12 pM | 148 ± 229 pM |
| [1]Potency IC50 on HuT 78 cells (FACS-based blockade of MAdCAM-1 binding) | 50 ± 11 pM | 193 ± 46 pM |
| [2]Potency IC50 on human lymphocytes (Plate-based cell adhesion blockade to MAdCAM-1) | 223 ± 86 pM | 630 ± 193 pM |
| Binding specificity | Binds to α4β7 No binding to α4β1 | Binds to α4β7 No binding to α4β1 |
| Human and cyno FcγR binding | Binds as expected for human IgG1 | No significant binding |
| In vitro Fc mediated ADCC, ADCP and CDC activities | No activity | No activity |
| Human and cyno FcRn binding | Binds at pH 6 | Binds at pH 6 |

[1]EC50 and IC50 values are based on ≥3 independent experiments
[2]Binding EC50 values are based on the PBMC isolated from ≥3 donors The major parameters of Ab-h1.9d-WT, such as its better binding affinity to α4β7 and its ability to bind human FcγRs without triggering Fc mediated effector functions, are the key differentiation factors from vedolizumab and these characteristics are anticipated to drive the improved efficacy over vedolizumab. Ab-h1.9d-WT also possesses the in vitro pharmacological attributes required for an anti-α4β7 clinical candidate.

8. EXEMPLARY EMBODIMENTS

While various specific embodiments have been illustrated and described, and some are represented below, it will be appreciated that various changes can be made without departing from the spirit and scope of the inventions(s).

1. An anti-human α4β7 antibody which comprises (i) a VH chain region comprising three CDRs; and (ii) a VL chain region comprising three CDRs, wherein:

VH CDR #1 is GFNIKNTYMH; (SEQ ID NO: 72)

VH CDR #2 is RIDPAKGHTEYAPKFLG; (SEQ ID NO: 73)

VH CDR #3 is VDV; (SEQ ID NO: 74)

VL CDR #1 is HASQDISDNIG; (SEQ ID NO: 75)

VL CDR #2 is HGTNLED; and (SEQ ID NO: 76)

VL CDR #3 is VQYAQFPWT. (SEQ ID NO: 77)

2. The anti-human α4β7 antibody of embodiment 1, which comprises
    a VH chain region of:

(SEQ ID NO: 70)
    EVQLVQSGAEVKKPGSSVKVSCKASGFNIKNTYMHWVRQAPGQGLEWI
    GRIDPAKGHTEYAPKFLGRVTITADESTNTAYMELSSLRSEDTAVYYC
    YYVDVWGQGTTVTVSS;

and
    a VL chain region of:

(SEQ ID NO: 71)
    DIQMTQSPSSLSASVGDRVTITCHASQDISDNIGWLQQKPGKSFKLLI
    YHGTNLEDGVPSRFSGSGSGTDYTLTISSLQPEDFATYYCVQYAQFPW
    TFGGGTKVEIK.

3. The anti-human α4β7 antibody of embodiment 1 or 2, which is humanized.
4. The anti-human α4β7 antibody of any of embodiments 1-3, which is an IgG.
5. The anti-human α4β7 antibody of any of embodiments 1-4, comprising a kappa light constant region.
6. The anti-human α4β7 antibody of any one of embodiments 1-5, which is an IgG$_1$.
7. The anti-human α4β7 antibody of any one of embodiments 1-6, comprising a variant CH3 domain having amino acid substitutions D356E and L358M.
8. The anti-human α4β7 antibody of any one of embodiments 1-7, which comprises a heavy chain having an amino acid sequence of SEQ ID NO:92 or SEQ ID NO:93, and a light chain having an amino acid sequence of SEQ ID NO:100.
9. The anti-human α4β7 antibody of any one of embodiments 1-8, comprising a variant CH2 domain having amino acid substitutions L234A and/or L235A.
10. The anti-human α4β7 antibody of any one of embodiments 1-9, comprising a variant CH2 domain having an amino acid substitution T250Q, and/or a variant CH3 domain having an amino acid substitution M428L.
11. A polynucleotide comprising a nucleotide sequence encoding an anti-human α4β7 antibody, wherein the antibody comprises (i) a VH chain region comprising three CDRs; and (ii) a VL chain region comprising three CDRs, wherein:

VH CDR #1 is GFNIKNTYMH; (SEQ ID NO: 72)

VH CDR #2 is RIDPAKGHTEYAPKFLG; (SEQ ID NO: 73)

VH CDR #3 is VDV; (SEQ ID NO: 74)

VL CDR #1 is HASQDISDNIG; (SEQ ID NO: 75)

VL CDR #2 is HGTNLED; and (SEQ ID NO: 76)

VL CDR #3 is VQYAQFPWT. (SEQ ID NO: 77)

12. An expression vector comprising the polynucleotide of embodiment 11.
13. A eukaryotic host cell transfected with the vector of embodiment 12.
14. A eukaryotic host cell engineered to express the polynucleotide of embodiment 11.
15. The eukaryotic host cell of embodiment 13 or 14, which is a mammalian host cell.
16. A method of producing an anti-human α4β7 antibody, comprising: (a) culturing the eukaryotic host cell of embodiment 15 and (b) recovering the anti-human α4β7 antibody.
17. A prokaryotic host cell transformed with the vector of embodiment 12.
18. A prokaryotic host cell engineered to express the polynucleotide of embodiment 17.
19. The prokaryotic host cell of embodiment 18, which is a bacterial host cell.
20. A method of producing an anti-human α4β7 antibody, comprising: (a) culturing the prokaryotic host cell of embodiment 19 and (b) recovering the anti-human α4β7 antibody.
21. A method of inducing viral suppression of HIV infection in an HIV-infected subject, comprising administering to the subject an amount of the anti-human α4β7 antibody of any one of embodiments 1-10.
22. The method of embodiment 21, wherein the viral suppression is immune-mediated.
23. A method of treating HIV infection in an HIV-infected subject, comprising administering to the subject an amount of the anti-human α4β7 antibody of any one of embodiments 1-10.

24. An anti-human α4β7 antibody, which suppresses HIV.
25. The anti-human α4β7 antibody of embodiment 24, which inhibits HIV replication and/or HIV infection.
26. The anti-human α4β7 antibody of embodiment 24, which inactivates and/or reduces activation of human α4β7 on cells expressing human α4β7.
27. The anti-human α4β7 antibody of embodiment 24, which induces internalization of human α4β7 on cells expressing human α4β7.
28. The anti-human α4β7 antibody of embodiment 24, which inhibits CD4 T cell co-stimulation.
29. The anti-human α4β7 antibody of embodiment 28, wherein CD4 T cell co-stimulation is mediated by MAdCAM-1 or HIV gp120.
30. The anti-human α4β7 antibody of embodiment 25, which inhibits HIV replication in CD4 T cells.
31. The anti-human α4β7 antibody of embodiment 30, wherein the CD4 T cells are MAdCAM-1 stimulated CD4 T cells or HIV gp120 stimulated CD4 T cells.
32. The anti-human α4β7 antibody of embodiment 24, which disrupts interaction of α4β7 with at least one of its ligands.
33. The anti-human α4β7 antibody of embodiment 32, wherein the α4β7 ligand is MAdCAM-1.
34. The anti-human α4β7 antibody of embodiment 32, wherein the α4β7 ligand is HIV gp120.
35. The anti-human α4β7 antibody of embodiment 34, which inhibits gp120-mediated cell-to-cell transmission of HIV.
36. The anti-human α4β7 antibody of embodiment 24, which binds to an HIV virion.
37. The anti-human α4β7 antibody of embodiment 36, wherein the antibody binding to the HIV virion forms an immune complex.
38. The anti-human α4β7 antibody of embodiment 37, wherein the immune complex binds to a FcγR on a cell.
39. The anti-human α4β7 antibody of embodiment 37, wherein the immune complex binds to a FcγR on an antigen presenting cell (APC).
40. The anti-human α4β7 antibody of embodiment 39, wherein the immune complex is taken up by the APC by phagocytosis.
41. The anti-human α4β7 antibody of embodiment 40, which induces an HIV-specific immune response.
42. The anti-human α4β7 antibody of embodiment 40 or 41, which induces a vaccination effect against HIV.
43. The anti-human α4β7 antibody of embodiment 41, wherein the HIV-specific immune response results in viral control of HIV in a HIV-infected individual.
44. The anti-human α4β7 antibody of embodiment 43, wherein the viral control results in reduced viral load
45. The anti-human α4β7 antibody of embodiment 43, wherein the viral control results in lower viral setpoint.
46. The anti-human α4β7 antibody of embodiment 43, wherein the viral control results in delay in viral rebound after an antiretroviral treatment interruption (ATI).
47. The anti-human α4β7 antibody of any one of embodiments 24-46, having a set of six complementary determining regions (CDRs) or the variable heavy chain region and variable light chain region from an antibody selected from Ab-m1, Ab-c1, Ab-h1.1, Ab-h1.2, Ab-h1.3, Ab-h1.4, Ab-h1.5, Ab-h1.6, Ab-h1.7, Ab-h1.8, Ab-h1.9, Ab-h1.9a, Ab-h1.9b, Ab-h1.9c, Ab-h1.9d, or Ab-h1.9e.
48. The anti-human α4β7 antibody of any one of embodiments 1-10, which suppresses HIV.
49. The anti-human α4β7 antibody of embodiment 48, which inhibits HIV replication and/or HIV infection.
50. The anti-human α4β7 antibody of embodiment 48, which inactivates and/or reduces activation of human α4β7 on cells expressing human α4β7.
51. The anti-human α4β7 antibody of embodiment 48, which induces internalization of human α4β7 on cells expressing human α4β7.
52. The anti-human α4β7 antibody of embodiment 48, which inhibits CD4 T cell co-stimulation.
53. The anti-human α4β7 antibody of embodiment 52, wherein CD4 T cell co-stimulation is mediated by MAdCAM-1 or HIV gp120.
54. The anti-human α4β7 antibody of embodiment 49, which inhibits HIV replication in CD4 T cells.
55. The anti-human α4β7 antibody of embodiment 54, wherein the CD4 T cells are MAdCAM-1 stimulated CD4 T cells or HIV gp120 stimulated CD4 T cells.
56. The anti-human α4β7 antibody of embodiment 48, which disrupts interaction of α4β7 with at least one of its ligands.
57. The anti-human α4β7 antibody of embodiment 56, wherein the α4β7 ligand is MAdCAM-1.
58. The anti-human α4β7 antibody of embodiment 56, wherein the α4β7 ligand is HIV gp120.
59. The anti-human α4β7 antibody of embodiment 58, which inhibits gp120-mediated cell-to-cell transmission of HIV.
60. The anti-human α4β7 antibody of embodiment 48, which binds to an HIV virion.
61. The anti-human α4β7 antibody of embodiment 60, wherein the antibody binding to the HIV virion forms an immune complex.
62. The anti-human α4β7 antibody of embodiment 61, wherein the immune complex binds to a FcγR on a cell.
63. The anti-human α4β7 antibody of embodiment 61, wherein the immune complex binds to a FcγR on an antigen presenting cell (APC).
64. The anti-human α4β7 antibody of embodiment 63, wherein the immune complex is taken up by the APC by phagocytosis.
65. The anti-human α4β7 antibody of embodiment 64, which induces an HIV-specific immune response.
66. The anti-human α4β7 antibody of embodiment 64 or 65, which induces a vaccination effect against HIV.
67. The anti-human α4β7 antibody of embodiment 64 or 65, wherein the HIV-specific immune response results in viral control of HIV in a HIV-infected individual.
68. The anti-human α4β7 antibody of embodiment 67, wherein the viral control results in reduced viral load.
69. The anti-human α4β7 antibody of embodiment 67, wherein the viral control results in lower viral setpoint.
70. The anti-human α4β7 antibody of embodiment 67, wherein the viral control results in delay in viral rebound after an antiretroviral treatment interruption (ATI).
71. A pharmaceutical composition comprising an antibody of any one of the preceding embodiments.

What is claimed:

1. An anti-human α4β7 monoclonal antibody which comprises (i) a VH chain region comprising three CDRs; and (ii) a VL chain region comprising three CDRs, wherein:

```
                                                (SEQ ID NO: 72)
        VH CDR #1 is GFNIKNTYMH;

(SEQ ID NO: 73)
        VH CDR #2 is RIDPAKGHTEYAPKFLG;

(SEQ ID NO: 74)
        VH CDR #3 is VDV;

(SEQ ID NO: 75)
        VL CDR #1 is HASQDISDNIG;

(SEQ ID NO: 76)
        VL CDR #2 is HGTNLED; and (SEQ ID NO: 77)
        VL CDR #3 is VQYAQFPWT.
```

2. The anti-human α4β7 monoclonal antibody of claim 1, which comprises a VH chain region of:

```
                                                (SEQ ID NO: 70)
EVQLVQSGAEVKKPGSSVKVSCKASGFNIKNTYMHWVRQAPGQGLEWI

GRIDPAKGHTEYAPKFLGRVTITADESTNTAYMELSSLRSEDTAVYYC

YYVDVWGQGTTVTVSS;
``` and a VL chain region of:

```
                                               (SEQ ID NO: 71)
DIQMTQSPSSLSASVGDRVTITCHASQDISDNIGWLQQKPGKSFKLLIY

HGTNLEDGVPSRFSGSGSGTDYTLTISSLQPEDFATYYCVQYAQFPWTF

GGGTKVEIK.
```

3. The anti-human α4β7 monoclonal antibody of claim 2, which is an IgG.

4. The anti-human α4β7 monoclonal antibody of claim 3, comprising a kappa light constant region.

5. The anti-human α4β7 monoclonal antibody of claim 4, which is an IgG$_1$.

6. The anti-human α4β7 monoclonal antibody of claim 5, comprising a variant CH3 domain having amino acid substitutions D356E and L358M.

7. The anti-human α4β7 monoclonal antibody of claim 1, which comprises a heavy chain having an amino acid sequence of SEQ ID NO:92 or SEQ ID NO:93, and a light chain having an amino acid sequence of SEQ ID NO:100.

8. The anti-human α4β7 monoclonal antibody of claim 1, which is an antibody comprising heavy chains each consisting of the amino acid sequence of SEQ ID NO:92, and light chains each consisting of the amino acid sequence of SEQ ID NO:100.

9. The anti-human α4β7 monoclonal antibody of claim 1, which is an antibody comprising heavy chains each consisting of the amino acid sequence of SEQ ID NO:93, and light chains each consisting of the amino acid sequence of SEQ ID NO:100.

\* \* \* \* \*